(12) United States Patent
Jervis

(10) Patent No.: US 6,364,892 B1
(45) Date of Patent: Apr. 2, 2002

(54) BALLON DISSECTOR WITH IMPROVED VISUALIZATION

(75) Inventor: James E. Jervis, Atherton, CA (US)

(73) Assignee: General Surgical Innovations, Inc., Norwalk, CT (US)

( * ) Notice: Subject to any disclaimer, the term of this patent is extended or adjusted under 35 U.S.C. 154(b) by 0 days.

(21) Appl. No.: 09/364,686

(22) Filed: Jul. 30, 1999

Related U.S. Application Data

(60) Continuation-in-part of application No. 09/107,834, filed on Jun. 30, 1998, which is a continuation of application No. 08/570,766, filed on Dec. 12, 1995, now Pat. No. 5,772,680, which is a continuation-in-part of application No. 08/403,012, filed on Mar. 10, 1995, now Pat. No. 5,540,711, which is a continuation-in-part of application No. 08/388,233, filed on Feb. 13, 1995, now Pat. No. 5,730,756, which is a continuation-in-part of application No. 08/267,488, filed on Jun. 29, 1994, now Pat. No. 5,607,443, which is a continuation-in-part of application No. 08/124,283, filed on Sep. 20, 1993, now Pat. No. 5,836,961, which is a continuation-in-part of application No. 08/073,737, filed on Jun. 8, 1993, now abandoned, which is a division of application No. 07/893,988, filed on Jun. 2, 1992.

(51) Int. Cl.⁷ .............................................. A61B 17/00
(52) U.S. Cl. ...................................... 606/190; 600/207
(58) Field of Search ............................ 604/103, 103.03, 604/103.14; 606/190–200; 600/201, 204, 207, 210

(56) References Cited

U.S. PATENT DOCUMENTS

| | | |
|---|---|---|
| 512,456 A | 9/1894 | Sadilkova |
| 1,213,005 A | 1/1917 | Pillsbury |
| 2,936,760 A | 5/1960 | Gants |
| 3,545,443 A | 12/1970 | Ansari et al. |
| 3,774,596 A | 11/1973 | Cook |
| 3,800,788 A | 4/1974 | White |
| 3,882,852 A | 5/1975 | Sinnreich |
| RE29,207 E | 5/1977 | Boldac et al. |
| 4,083,369 A | 4/1978 | Sinnreich |
| 4,217,889 A | 8/1980 | Radovan et al. |
| 4,243,050 A | 1/1981 | Litttleford |
| 4,276,874 A | 7/1981 | Wolvek et al. |
| 4,312,353 A | 1/1982 | Shahbabian |
| 4,411,654 A | 10/1983 | Boarini et al. |
| 4,447,227 A | 5/1984 | Kotsanis |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |

(List continued on next page.)

FOREIGN PATENT DOCUMENTS

| | | |
|---|---|---|
| WO | WO 92/06638 | 4/1992 |
| WO | WO 9532663 | 12/1995 |
| WO | WO 9725094 | 7/1997 |
| WO | WO 9734532 | 9/1997 |

Primary Examiner—Glenn K. Dawson

(57) ABSTRACT

An expansible tunneling apparatus and associated methods for creating an anatomic working space for a surgical procedure. Various embodiments of one and two piece apparatus that permit laparoscopic observation both during tunneling and during subsequent balloon dissection are disclosed. In a disclosed one piece embodiment, a tubular member has a bore extending therethrough and an open distal end. A lip is formed in the distal end of the tubular member to capture the distal tip of a laparoscope that is inserted into the tubular member to permit observation of the procedure both during tunneling to a desired location and during subsequent balloon inflation. An elongated neck of the balloon is secured to the tunneling member. The elongated neck permits the tubular member to be withdrawn slightly from the balloon after inflation to facilitate observation. After the balloon has been advanced to the desired location in the body it is inflated through a balloon inflation lumen to cause the balloon to dissect tissue and create an operating space. Various balloon constructions and a reusable design are also disclosed.

36 Claims, 44 Drawing Sheets

U.S. PATENT DOCUMENTS

| | | |
|---|---|---|
| 4,596,554 A | 6/1986 | Dastgeer |
| 4,644,936 A | 2/1987 | Schiff |
| 4,654,030 A | 3/1987 | Moll et al. |
| 4,685,447 A | 8/1987 | Iversen et al. |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,854,316 A | 8/1989 | Davis |
| 4,869,717 A | 9/1989 | Adair |
| 4,888,000 A | 12/1989 | McQuilkin et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,104,383 A | 4/1992 | Shichman |
| 5,116,318 A | 5/1992 | Hillstead |
| 5,116,357 A | 5/1992 | Eberbach |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Innairuberto et al. |
| 5,232,446 A | 8/1993 | Arney |
| 5,258,026 A | 11/1993 | Johnson et al. |
| 5,269,753 A | 12/1993 | Wilk |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,402,772 A | 4/1995 | Moll et al. |
| 5,407,433 A | 4/1995 | Loomas |
| 5,431,173 A | 7/1995 | Chin et al. |
| 5,468,248 A | 11/1995 | Chin et al. |
| 5,505,698 A | 4/1996 | Booth et al. |
| 5,588,951 A | 12/1996 | Zhu et al. |
| 5,690,668 A | 11/1997 | Fogarty et al. |
| 5,720,762 A | 2/1998 | Bass |
| 5,730,748 A | 3/1998 | Fogarty et al. |
| 5,772,680 A | 6/1998 | Kieturakis et al. |

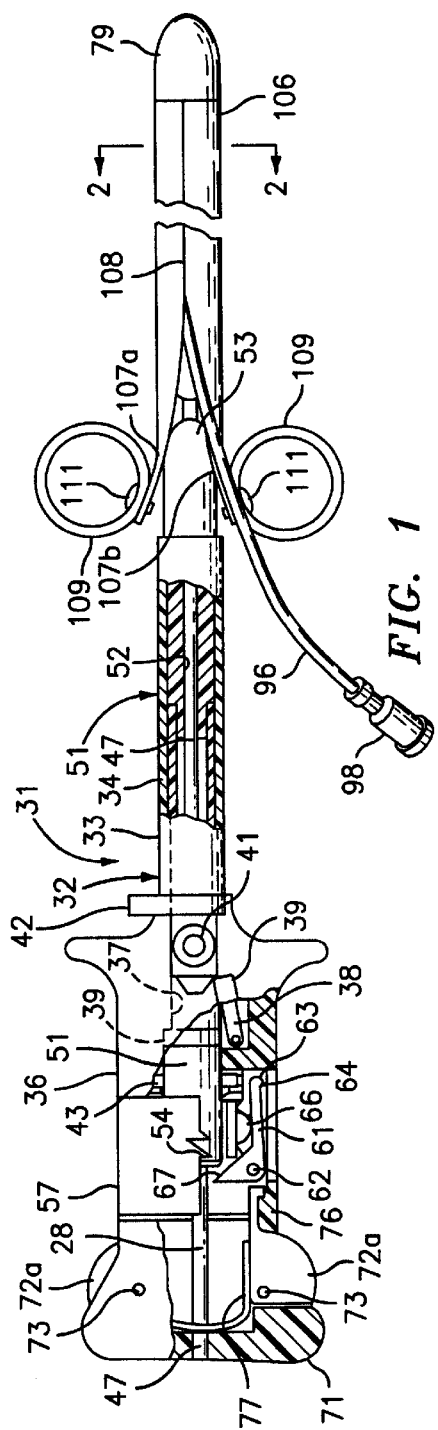
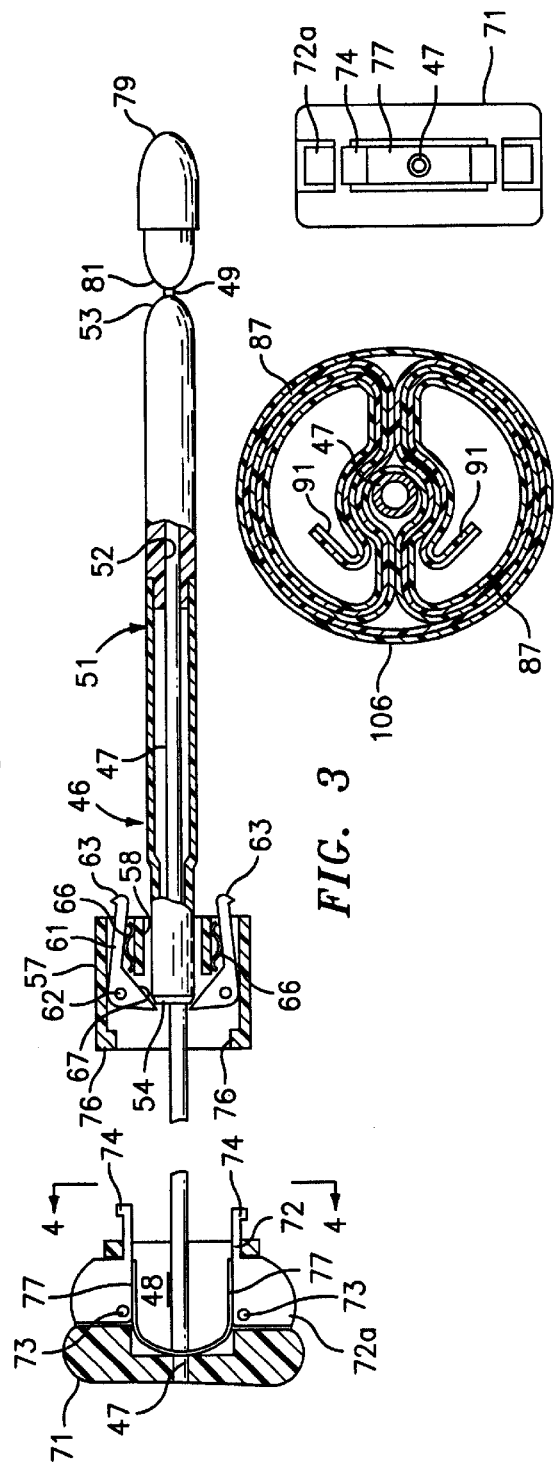
FIG. 1
FIG. 2
FIG. 3
FIG. 4

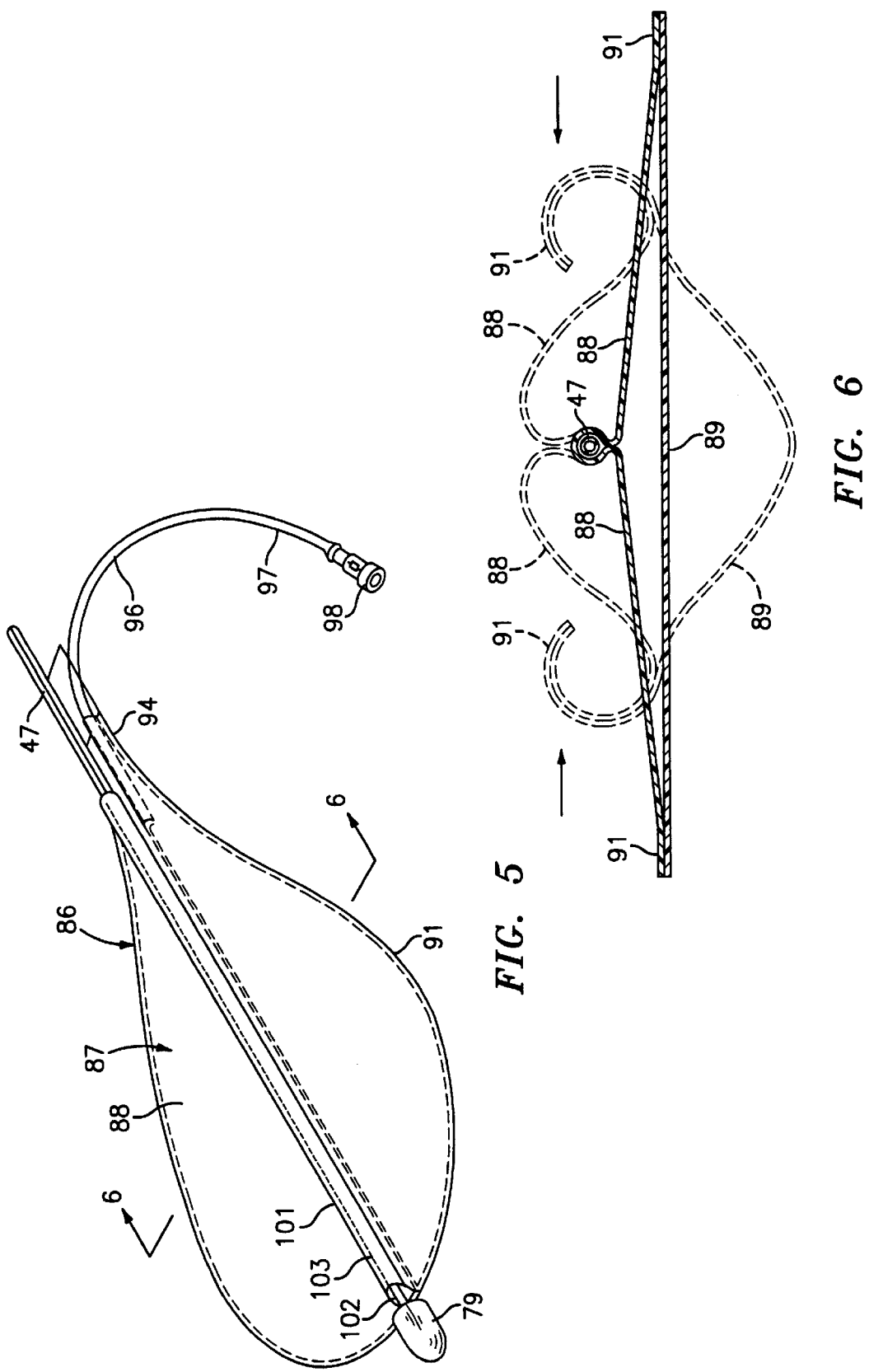

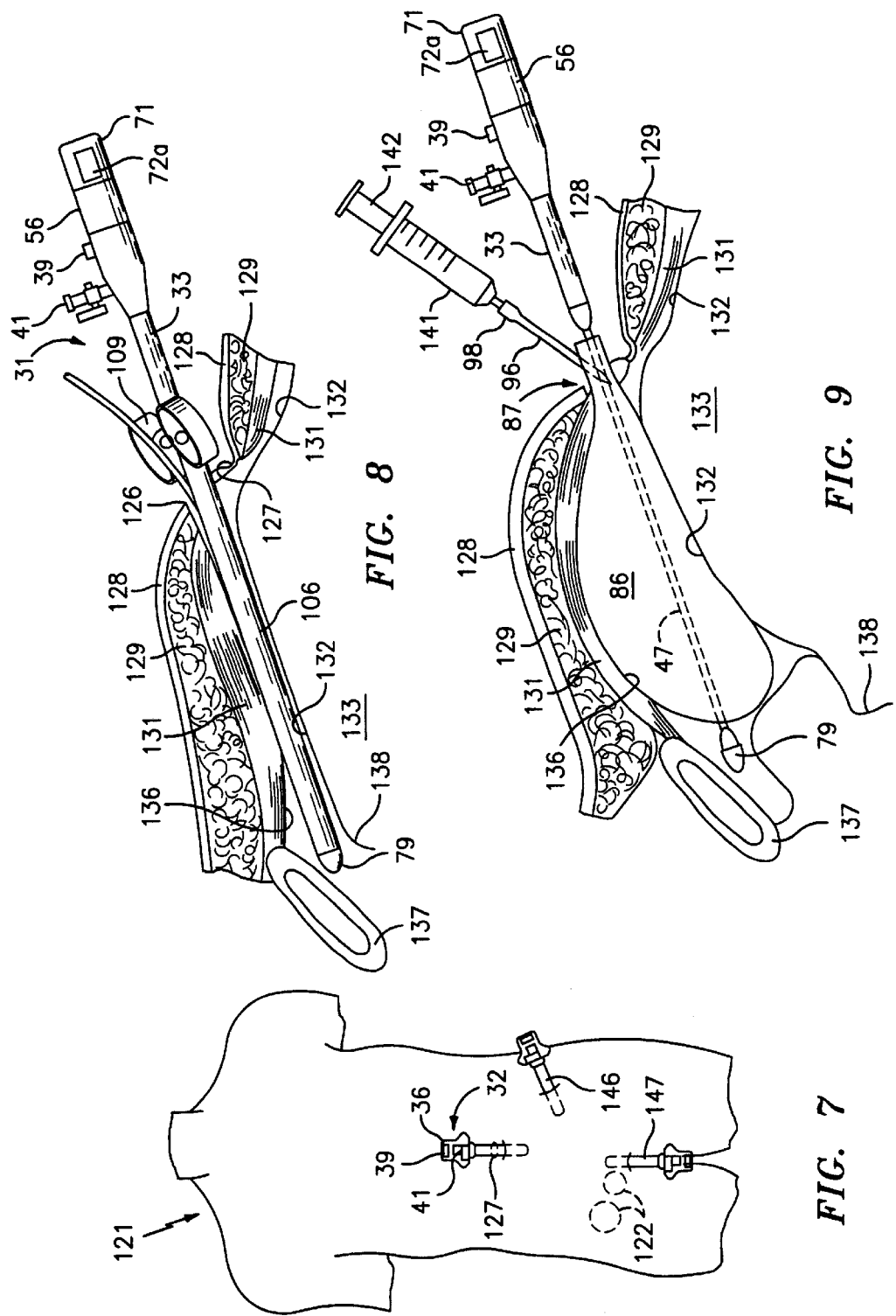

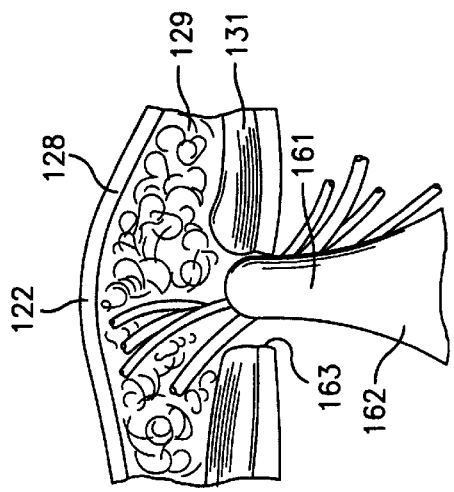
FIG. 15
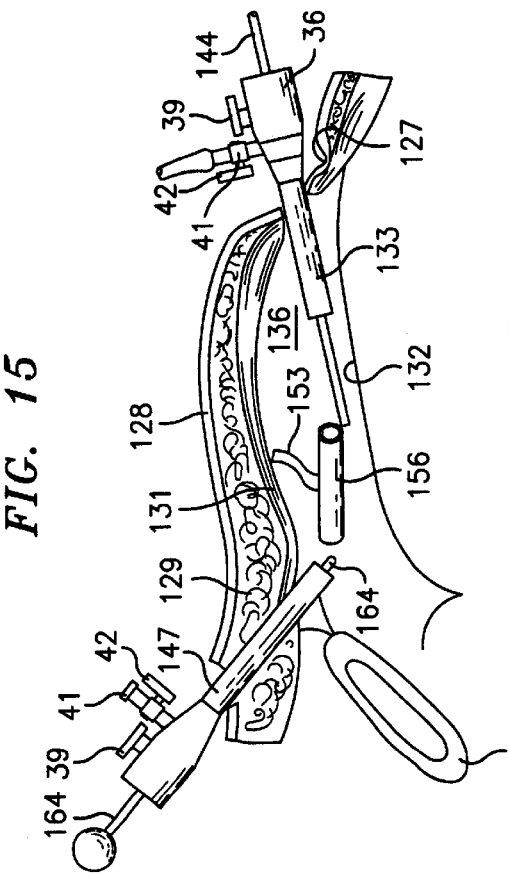
FIG. 16
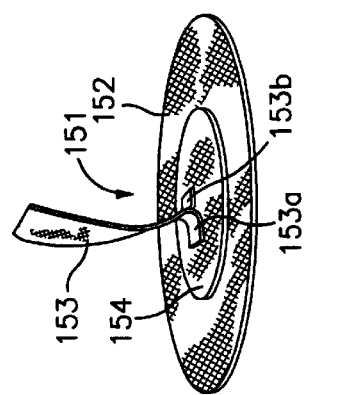
FIG. 12
FIG. 13
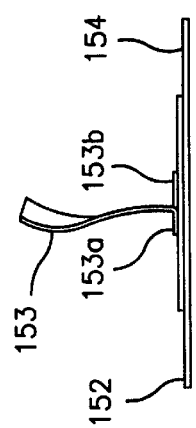
FIG. 14

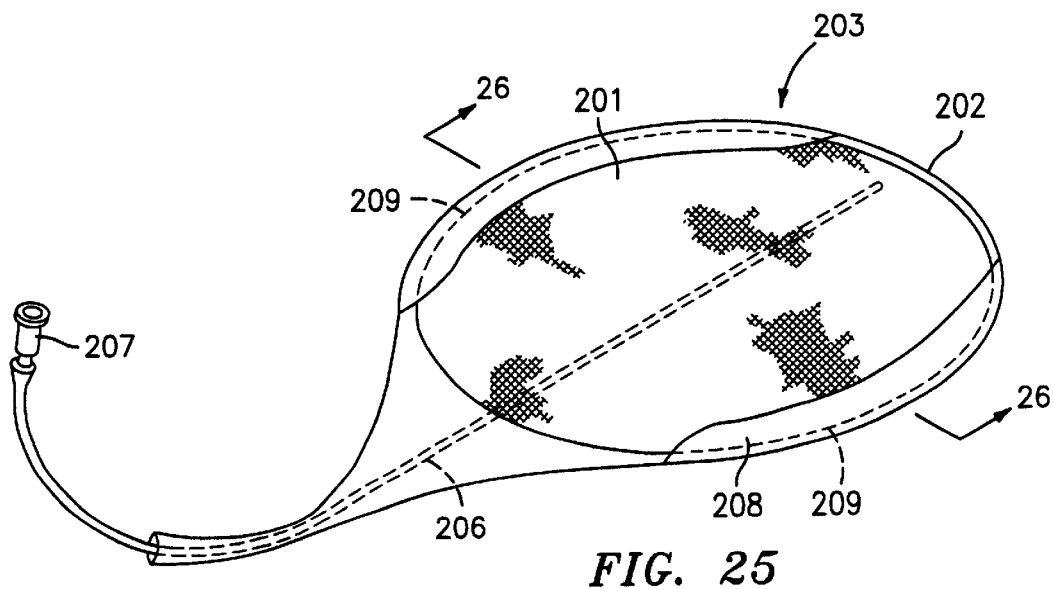
FIG. 25
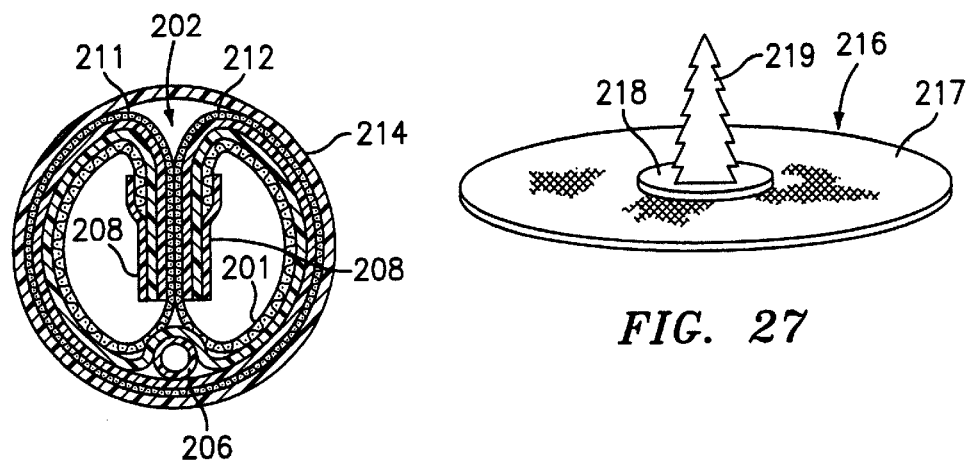
FIG. 26
FIG. 27
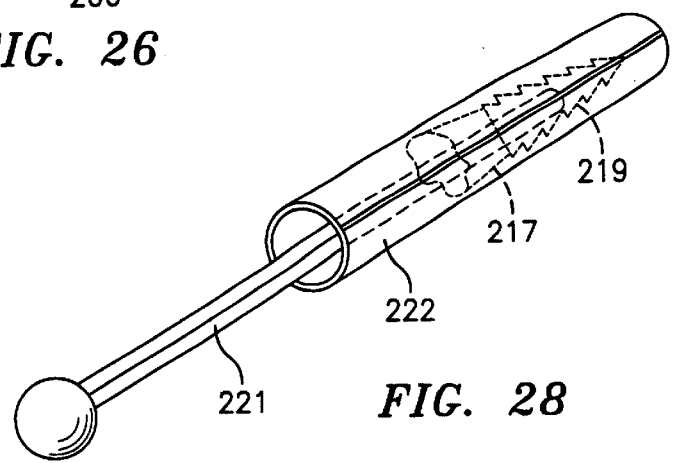
FIG. 28

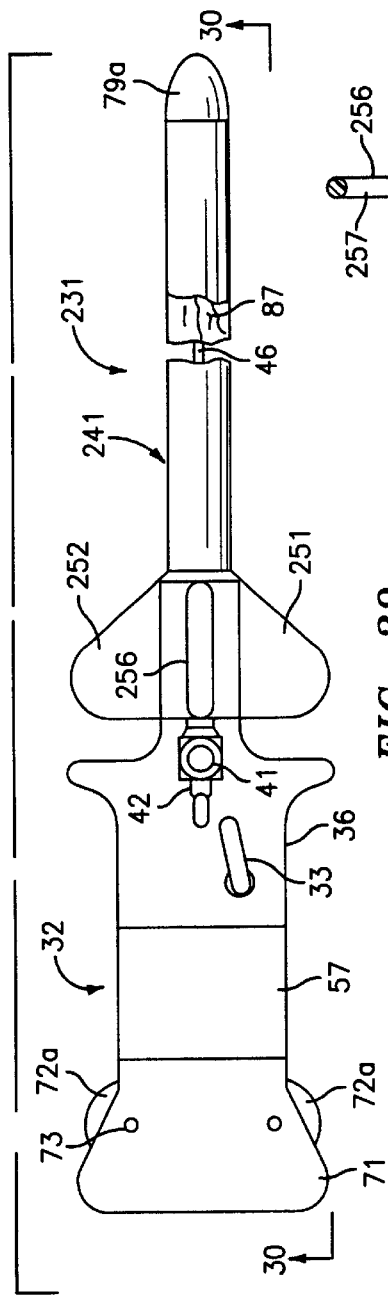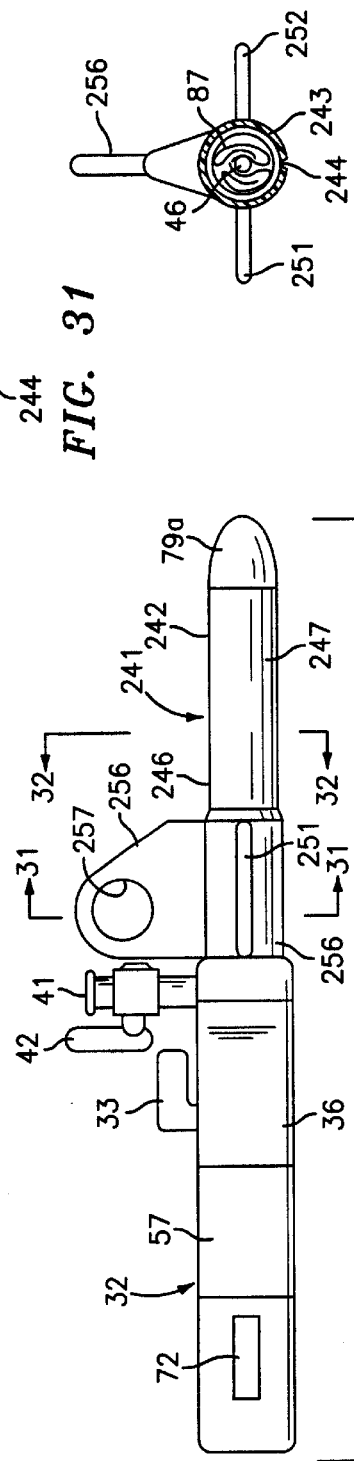
FIG. 29
FIG. 31
FIG. 32
FIG. 30

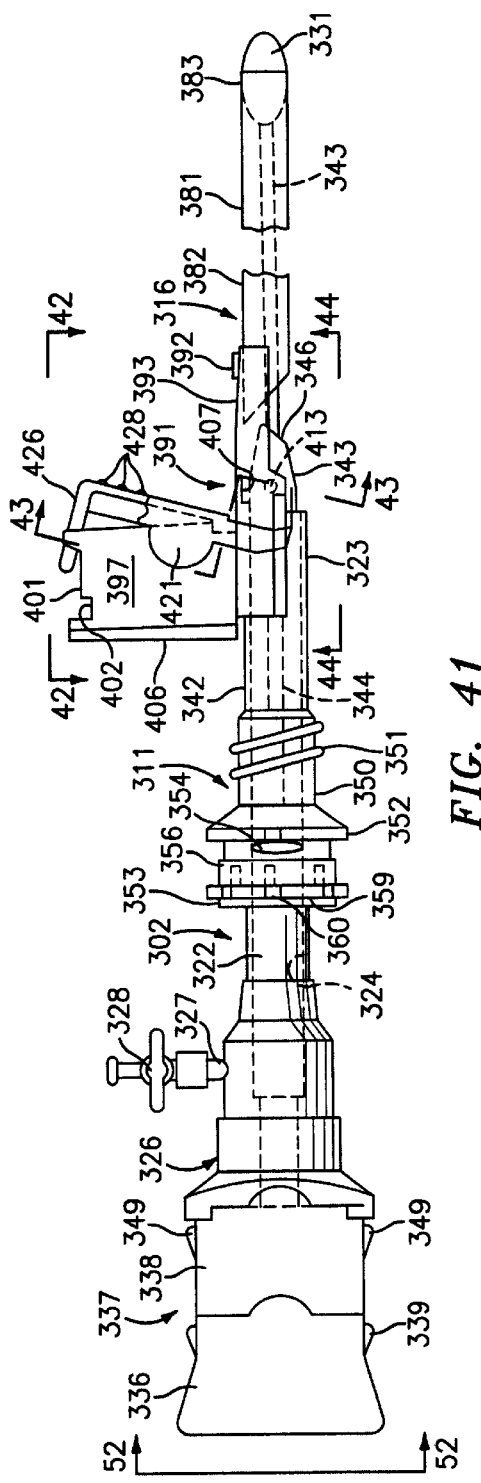
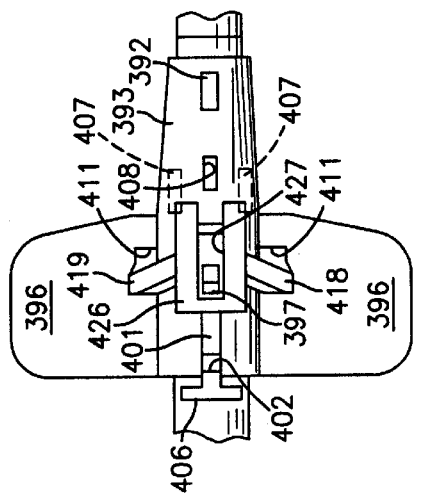
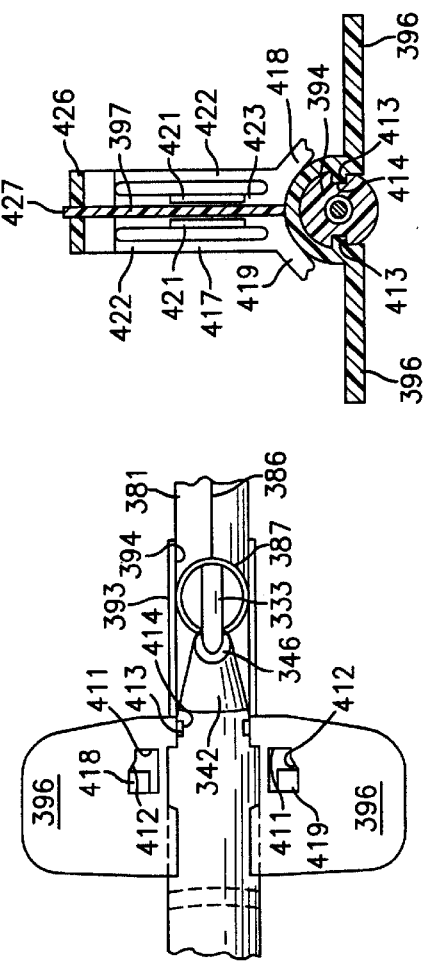
FIG. 41
FIG. 42
FIG. 43
FIG. 44

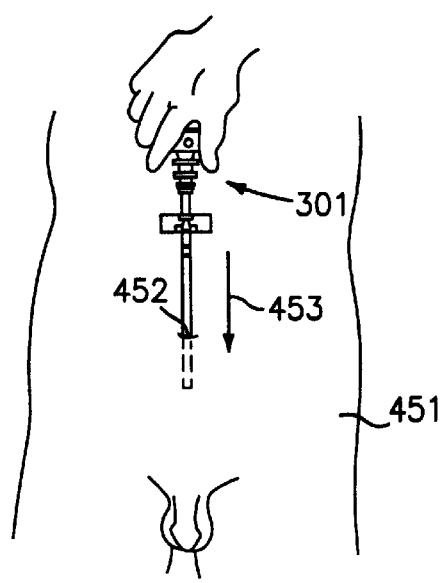
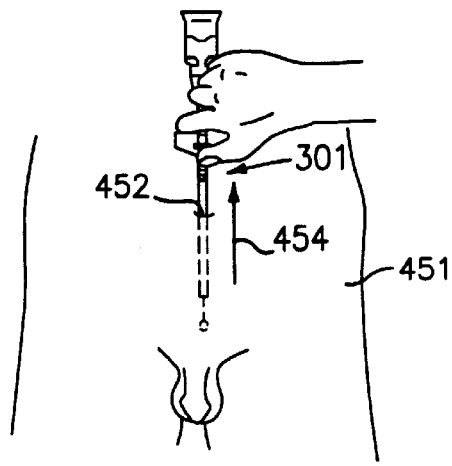
FIG. 49A   FIG. 49B
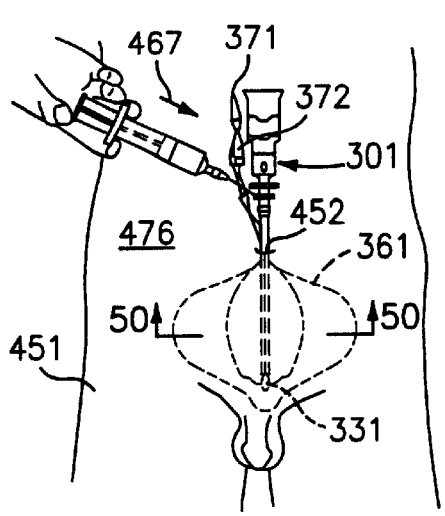
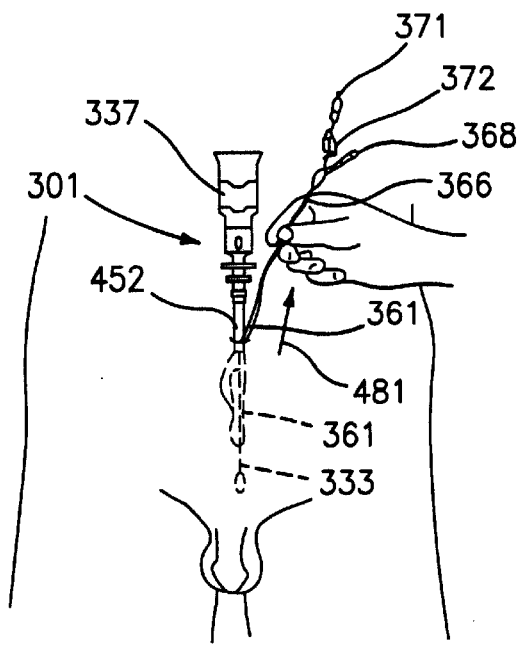
FIG. 49C   FIG. 49D

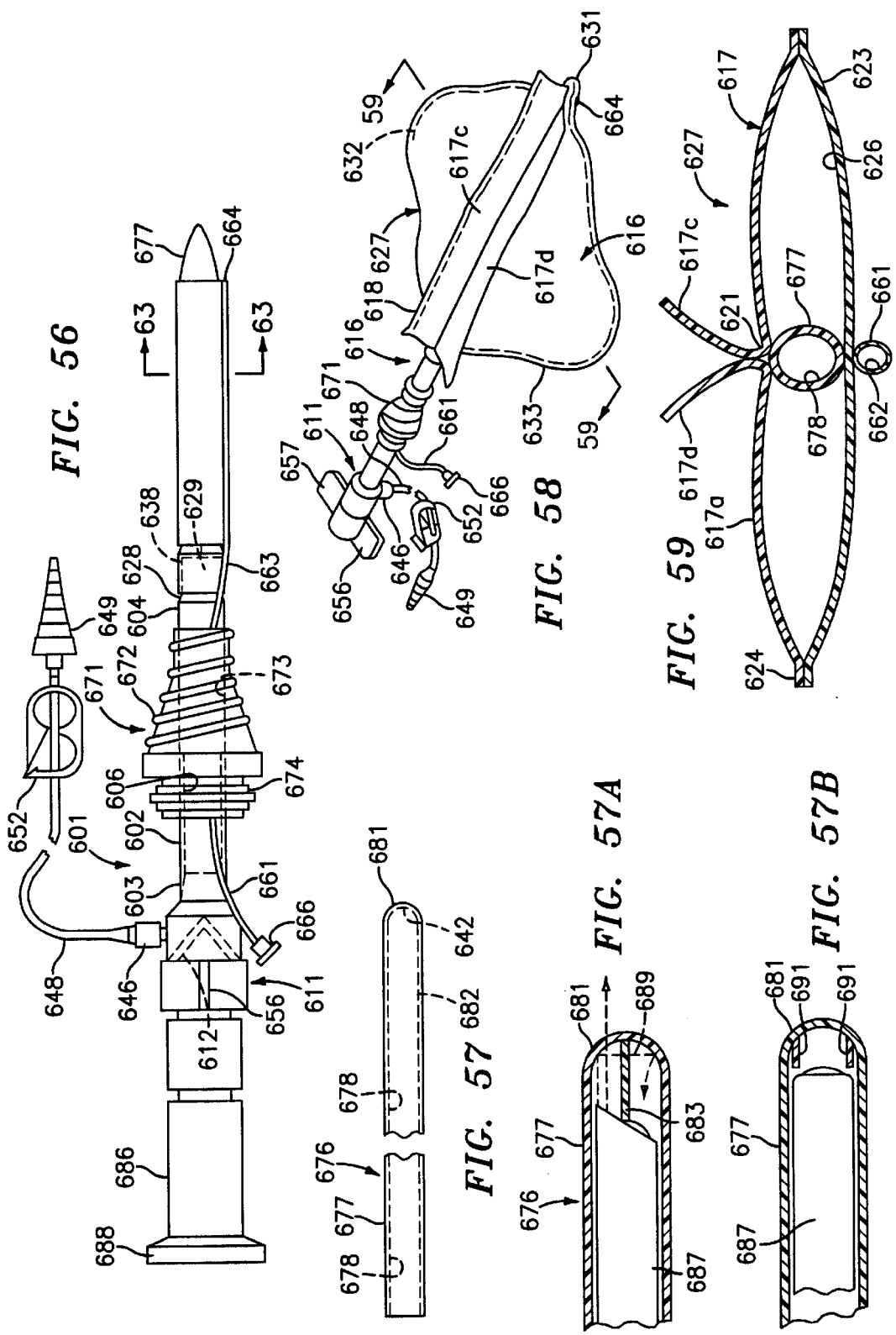

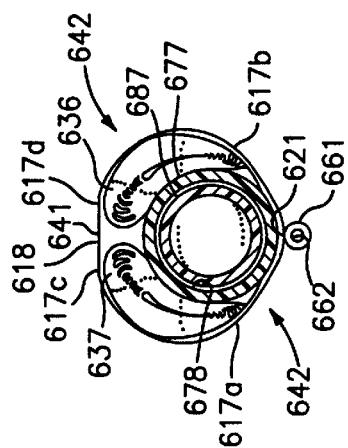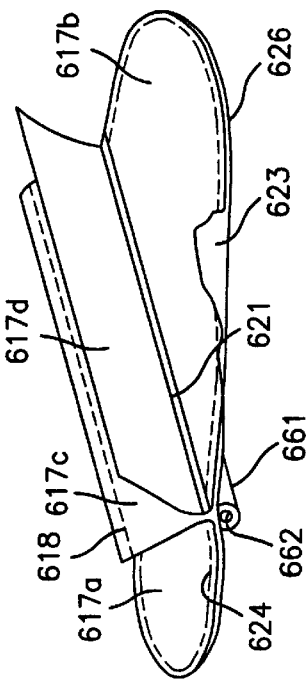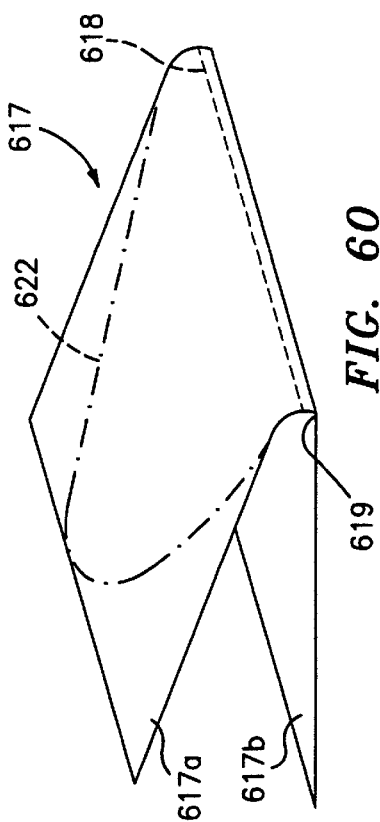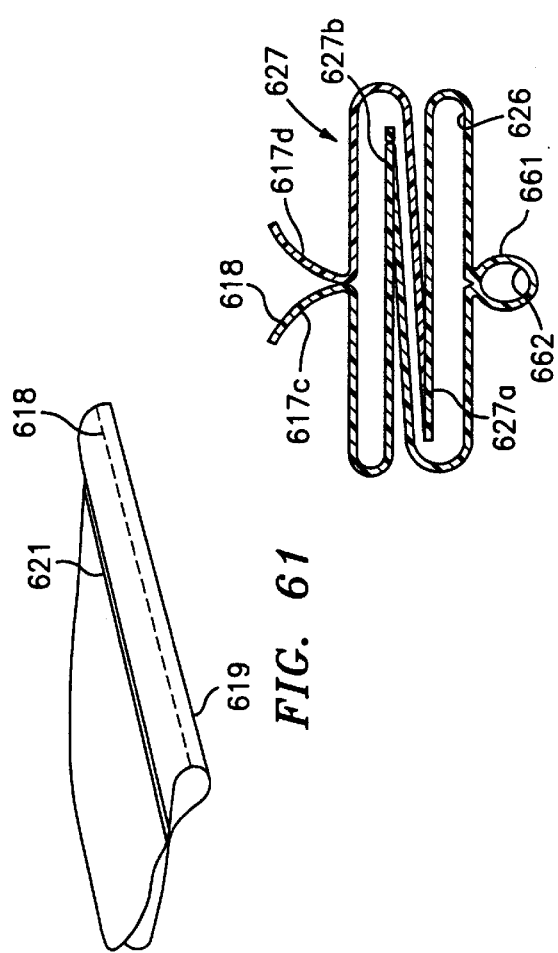

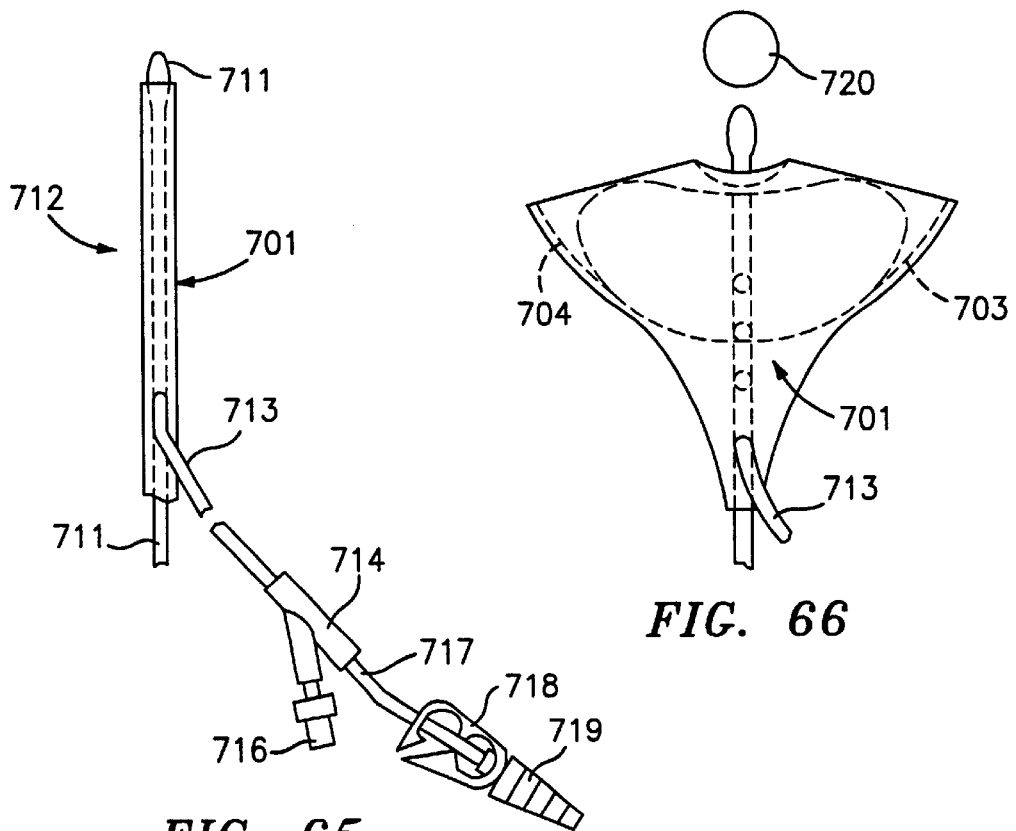
FIG. 66
FIG. 65
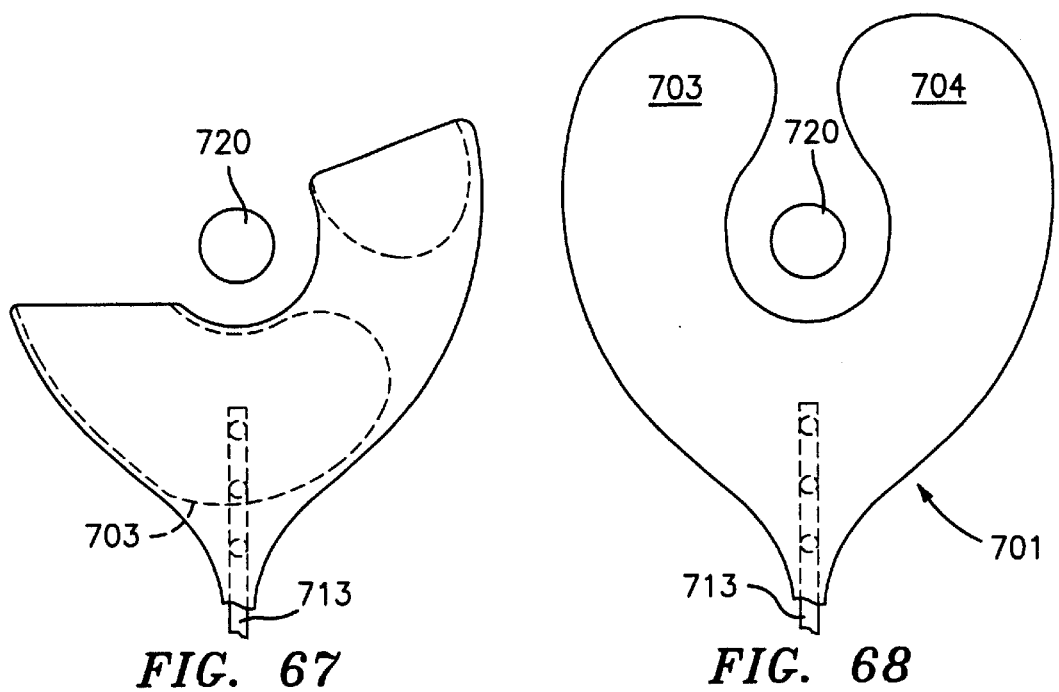
FIG. 67
FIG. 68

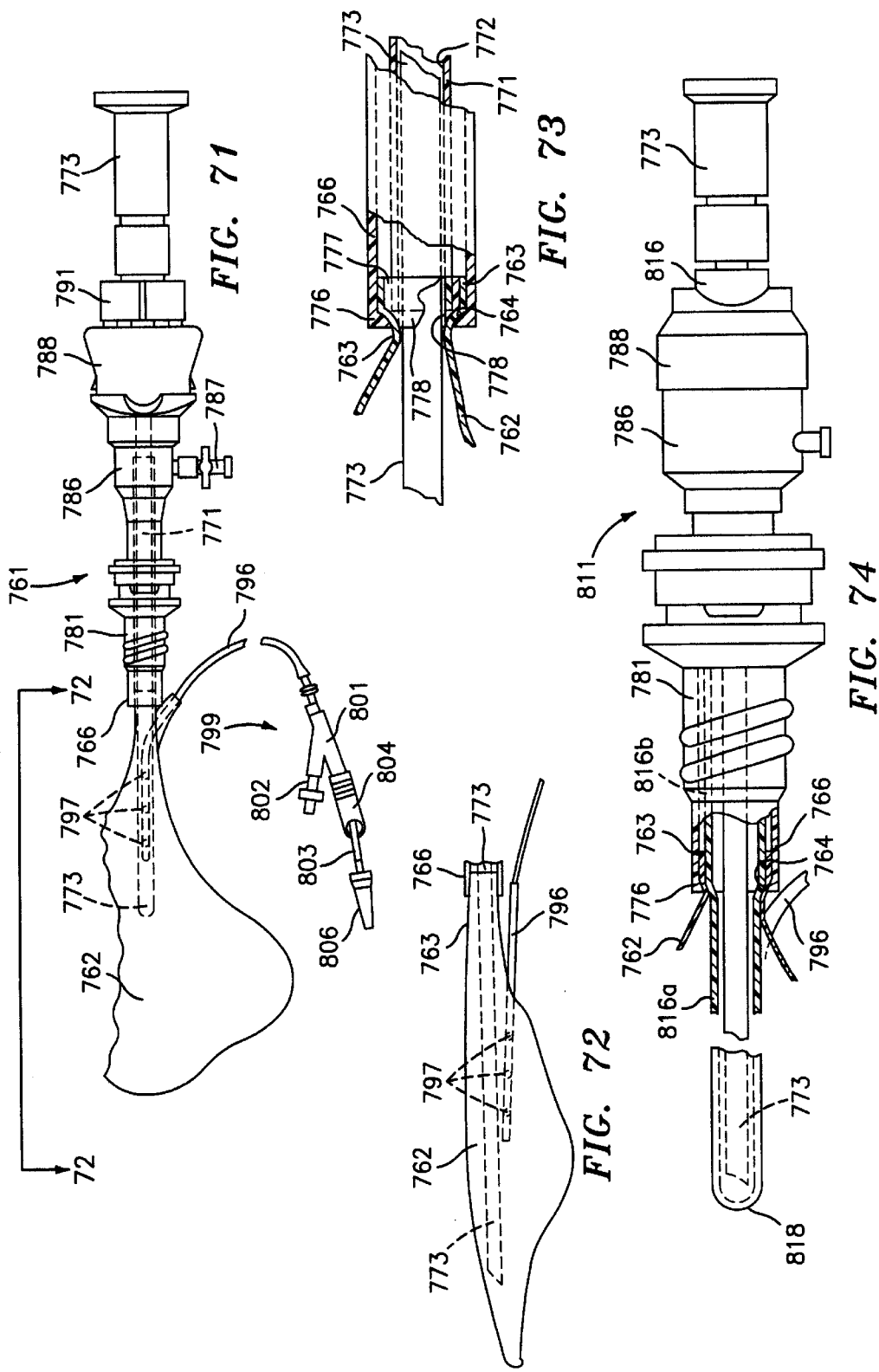

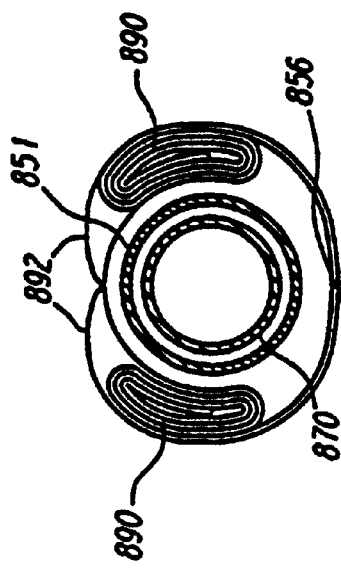
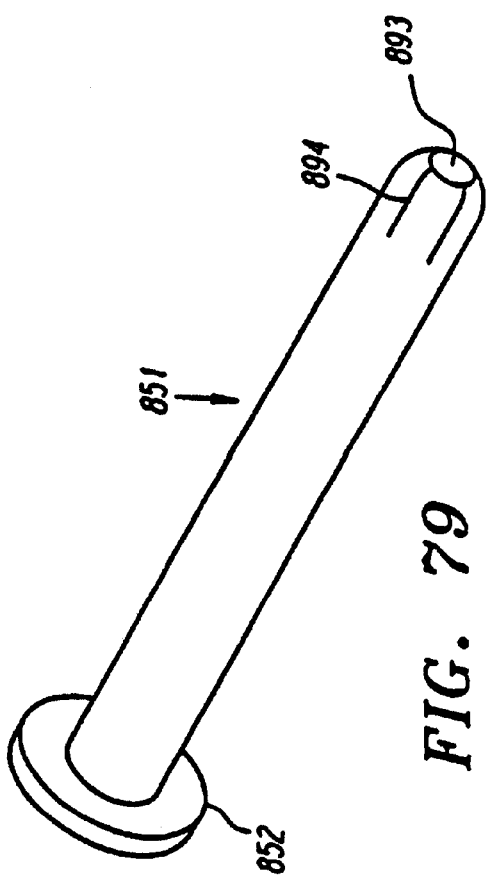
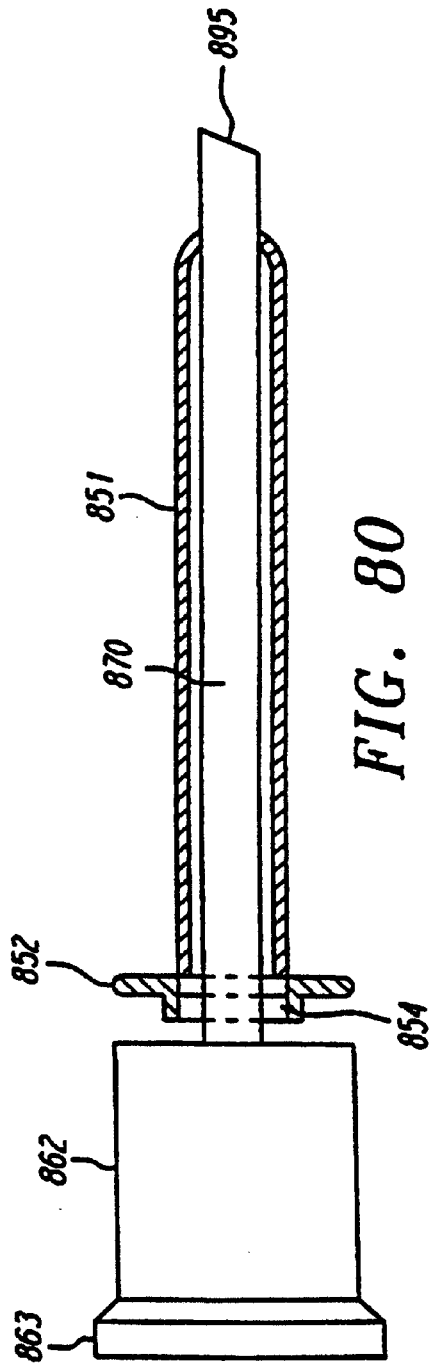

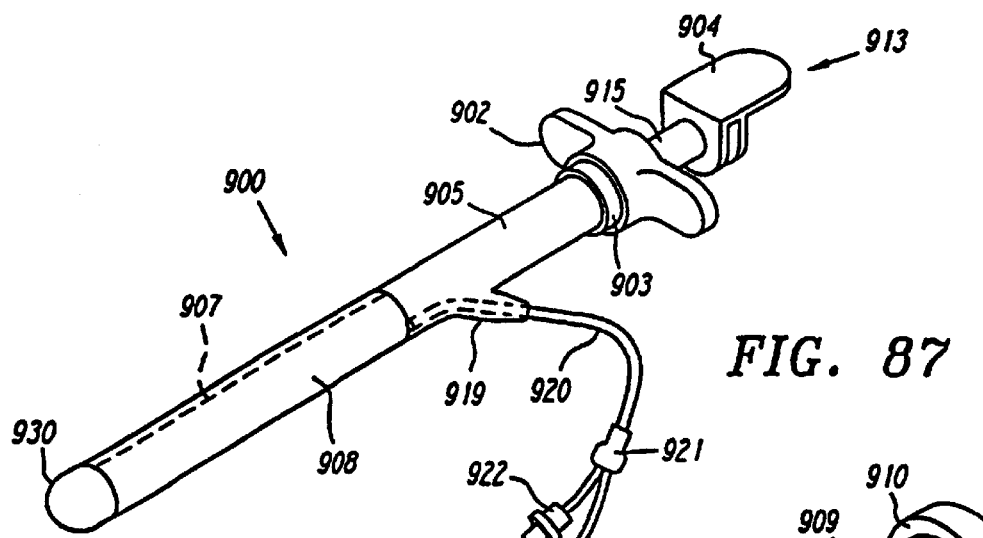
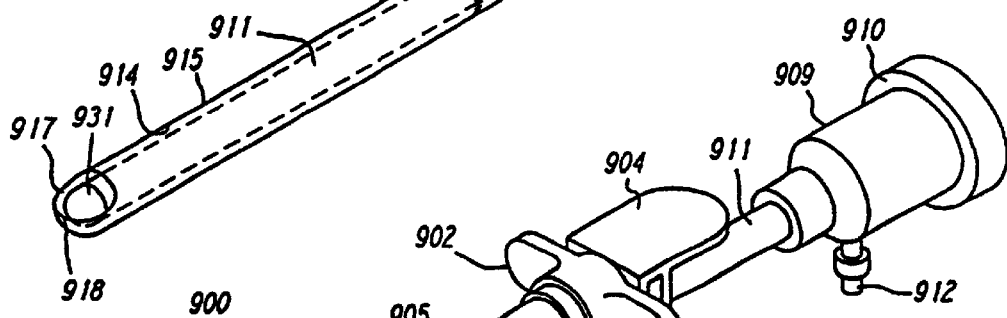
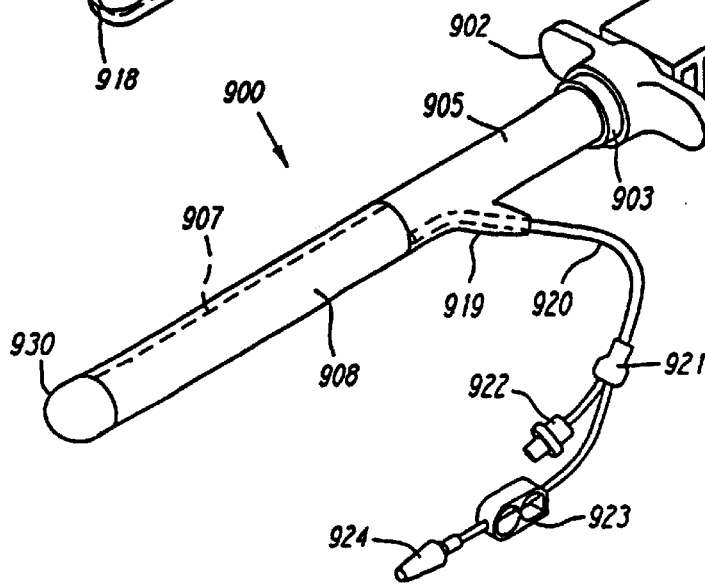
FIG. 87
FIG. 88
FIG. 89

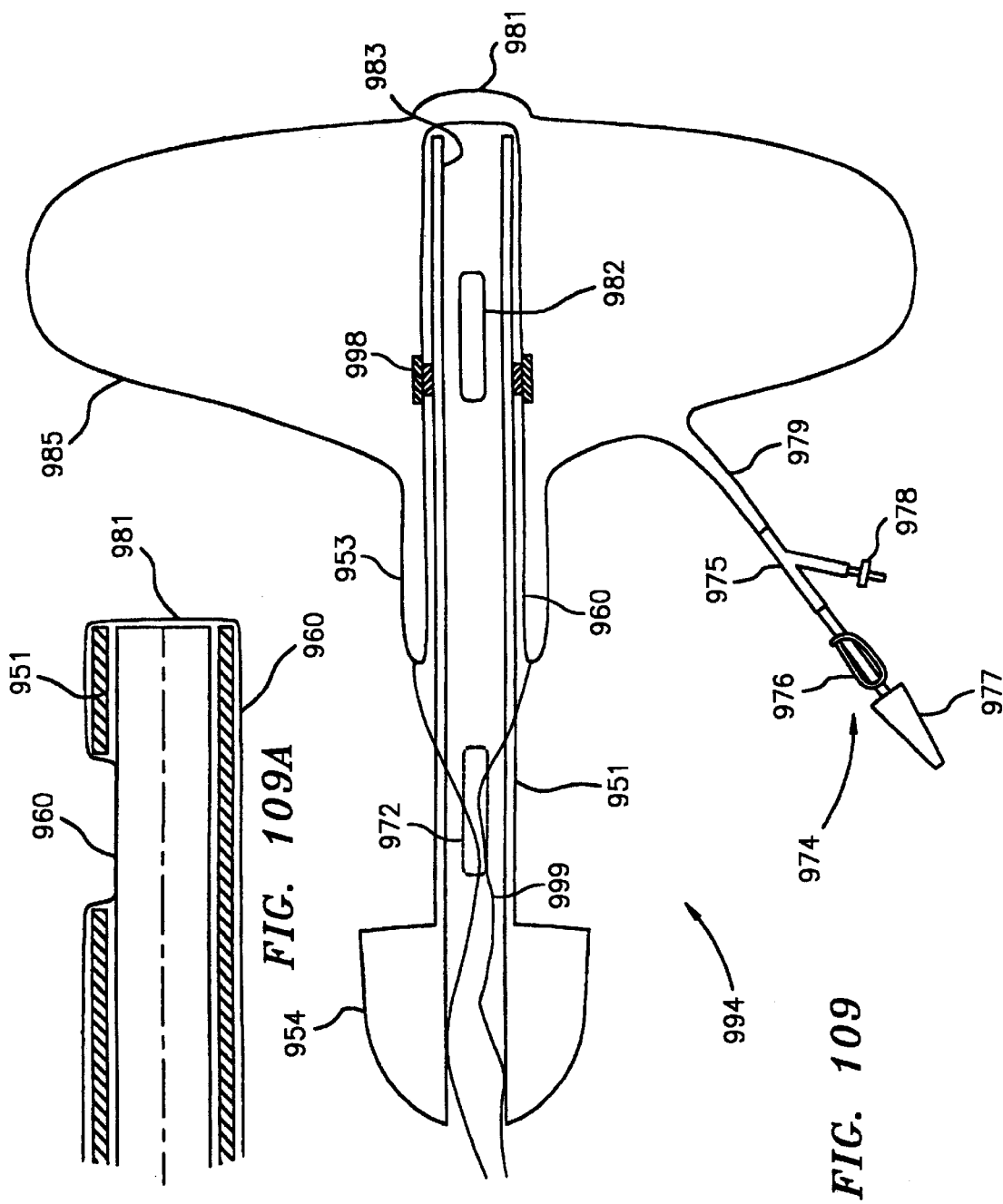

BALLON DISSECTOR WITH IMPROVED VISUALIZATION

CROSS REFERENCE TO RELATED APPLICATIONS

This is a continuation-in-part of copending U.S. application Ser. No. 09/107,834, filed on Jun. 30, 1998, now pending, which is a continuation of application Ser. No. 08/570,766, filed on Dec. 12, 1995, now U.S. Pat. No. 5,772,680, which is a continuation-in-part of application Ser. No. 08/403,012, filed on Mar. 10, 1995, now U.S. Pat. No. 5,540,711, which is a continuation-in-part of application Ser. No. 08/388,233, filed on Feb. 13, 1995, now U.S. Pat. No. 5,730,756, which is a continuation-in-part of application Ser. No. 08/267,488, filed on Jun. 29, 1994, now U.S. Pat. No. 5,607,443,which is a continuation-in-part of application Ser. No. 08/124,283, filed Sep. 20, 1993, now U.S. Pat. No. 5,836,961, which is a continuation-in-part of application Ser. No. 08/073,737, filed on Jun. 8, 1993, now abandoned, which is a division of application Ser. No. 07/893,988, filed on Jun. 2, 1992, now pending. The disclosures of each of these prior applications are hereby incorporated by reference in their entirety.

BACKGROUND OF THE INVENTION

This invention relates generally to an apparatus and method for developing an anatomic space for laparoscopic procedures, and more specifically, to an apparatus and method that provides for laparoscopic visualization both during tunneling dissection to the desired anatomic space as well as during subsequent tissue dissection during balloon inflation once the desired potential space has been identified.

In the past, in developing spaces and potential spaces within a body, blunt dissectors or soft-tipped dissectors have been utilized to create a dissected space which is parallel to the plane in which the dissectors are introduced into the body tissue. This often may be in an undesired plane, which can lead to bleeding which may obscure the field and make it difficult to identify the body structures. In utilizing such apparatus and methods, attempts have been made to develop anatomic spaces in the anterior, posterior or lateral to the peritoneum. The same is true for pleural spaces and other anatomic spaces. Procedures that have been performed in such spaces include varicocele dissection, lymph node dissection, sympathectomy and hernia repair. In the past, the inguinal hernia repair has principally been accomplished by the use of an open procedure which involves an incision in the groin to expose the defect in the inguinal floor, removal of the hernial sac and subsequent suturing the ligaments and fascias together to reinforce the weakness in the abdominal wall. Recently, laparoscopic hernia repairs have been attempted by inserting laparoscopic instruments into the abdominal cavity through the peritoneum and then placing a mesh patch over the hernia defect. Hernia repair using this procedure has a number of disadvantages, principally because the mesh used for the hernia repair is in direct contact with the structures in the abdominal cavity, as for example the intestines, there is a tendency for adhesions to form between these structures. Such adhesions are known to be responsible for certain occasionally serious complications. Such a procedure is also undesirable because typically the patch is stapled to the peritoneum, which is a very thin unstable layer covering the inner abdomen. Thus, the stapled patch can tear away from the peritoneum or shift its position. Other laparoscopic approaches involve cutting away the peritoneum and stapling it closed. This is time consuming, however, and involves the risk that important anatomic structures may be inadvertently cut. In addition, such a procedure is undesirable because it requires the use of a general anesthesia. There is therefore a need for a new and improved apparatus and method for developing an anatomic space and particularly for accomplishing hernia repair by laparoscopy.

SUMMARY OF THE INVENTION

In general, it is an object of the present invention to provide an apparatus and method for developing an anatomic space.

Another object of the invention is to provide an apparatus and method in which such an anatomic space is developed by applying perpendicular forces to create the anatomic space at the weakest plane to create a more natural, less traumatic and bloodless region in which to work.

Another object of the invention is to provide an apparatus and method to obtain surgical exposure in the preperitoneal space.

Another object of the invention is to provide an apparatus and method to create preperitoneal working space utilizing a balloon dissector.

Another object of the present invention is to provide an apparatus and method of the above character for developing an anatomic space for laparoscopic hernia repair through the anatomic space.

Another object of the invention is to provide an apparatus and method for decreasing the time and risk associated with creating a preperitoneal working space.

Another object of the invention is to provide an apparatus and method of the above character for a minimally invasive procedure.

Another object of the invention is to provide an apparatus and method of the above character which can be accomplished without the use of general anesthesia.

Another object of the invention is to provide an apparatus and method of the above character which can be accomplished with a spinal or epidural anesthesia.

Another object of the invention is to provide an apparatus and method of the above character which provides substantially reduced medical costs and a greatly reduced patient recovery time.

Another object of the invention is to provide an apparatus of the above character which is relatively simple and compact.

Another object of the invention is to provide an apparatus and method of the above character which can be readily utilized by surgeons.

Another object of the invention is to provide a patch for use with the apparatus which is firmly secured during the hernia repair.

Another object of the invention is to provide a balloon which has a modified asymmetric manta ray configuration to aid in providing the desired configuration for the extraperitoneal working space for hernia repair.

Another object of the invention is to provide a balloon dissection apparatus which has a balloon cover detachably secured to an obturator so that the balloon dissection device is relatively rigid to permit the balloon dissection apparatus to be grasped by the handle to operate the same during dissection.

Another object of the invention is to provide a balloon dissection apparatus of the above character in which a precise release mechanism is provided for releasing the balloon cover from the obturator so that the surgeon can be assured that the balloon cover has been released before it is removed to release the balloon.

Another object of the invention is to provide a balloon dissection apparatus of the above character in which the guide rod or obturator remains in place to maintain ready access to the extraperitoneal working space.

Another object of the invention is to provide a balloon dissection apparatus of the above character in which certain of the parts which are to be moved relative to other parts are color coded to aid the surgeon in use of the apparatus.

Another object of the apparatus is to provide a tubular member which is provided with a tip having an inclined surface.

Another object of the invention is to provide a balloon dissection apparatus which is provided with a blunt tip which has a diameter which is less than the diameter of the cannula tube.

Another object of the invention is to provide a balloon dissection apparatus of the above character in which at least a part of the same can be sterilized and reused.

Another object of the invention is to provide an apparatus and method of the above character which has been simplified.

Another object of the invention is to provide an apparatus and method of the above character which decreases the number of steps required to complete a dissection process.

Another object of the invention is to provide an apparatus and method which permits a visualization of the insertion of the balloon into the posterior rectus space at the time of insertion.

Another object of the invention is to provide an apparatus of the above character which makes it possible to utilize conventional cannulae.

Another object of the invention is to provide an apparatus of the above character which makes it possible to utilize a laparoscope during the surgical procedure to permit viewing of the dissection as it is occurring.

Another object of the invention is to provide an apparatus of the above character in which laparoscopic observation can be accomplished through the balloon if desired as dissection is taking place.

Another object of the invention is to provide an apparatus of the above character in which a separate removable sheath is not required for encasing the balloon prior to inflation.

Another object of the invention is to provide an inflatable balloon which can be utilized to dissect around obstructions.

Another object of the invention is to provide a balloon utilized for dissection which is provided in laterally inwardly extending folds to aid in dissecting as the balloon is inflated.

Another object of the invention is to provide a laparoscopic apparatus including a tunneling member, channel guide and balloon assembly into which a conventional laparoscope may be inserted for visualization of anatomic structures as the tunneling member and laparoscope are advanced through an incision to the desired location within the body where dissection of tissue layers is desired.

Another object of the invention is to provide a tunneling member and balloon assembly of the above character wherein the tunneling member has an open distal end that permits a laparoscope to be advanced outside the tunneling member into the interior of the balloon during balloon inflation to permit observation of tissue dissection through a single balloon layer.

Another object of the invention is to provide a tunneling member and balloon assembly of the above character which includes a U shaped channel guide that remains within the incision site after the tunneling member and laparoscope are withdrawn to provide reliable access back to the previously created space.

Another object of the invention is to provide an apparatus of the above character in which a separate removable sheath is not required to cover the balloon prior to inflation.

Another object of the invention is to provide an apparatus of the above character which includes an optional endoscope guide which may be inserted into the incision during tunneling dissection to preserve access to the created space for subsequent laparoscopic procedures.

Additional objects and features of the invention will appear from the following description in which the preferred embodiments are set forth in detail in conjunction with the accompanying drawings.

BRIEF DESCRIPTION OF THE DRAWINGS

FIG. 1 is a side elevational view partially in cross-section of a laparoscopic apparatus incorporating the present invention.

FIG. 2 is a cross-sectional view taken along the 2—2 of FIG. 1.

FIG. 3 is a side elevational view partially in cross-section of the tunneling shaft forming a part of the apparatus shown in FIG. 1 after it has been removed from the apparatus shown in FIG. 1.

FIG. 4 is a cross-sectional view taken along the line 4—4 of FIG. 3.

FIG. 5 is an isometric view of the inflatable balloon utilized in the apparatus in FIG. 1 secured to the tunneling rod.

FIG. 6 is a cross-sectional view taken along the line 6—6 of FIG. 5, and showing by dotted lines the manner in which the balloon as it unfolds develops the anatomic space.

FIG. 7 is a partial plan view of a prone human body, showing the lower abdomen showing the manner in which the laparoscopic apparatus of the present invention is utilized for performing a hernia repair through the preperitoneal space.

FIG. 8 is a sagittal view of the lower abdominal cavity of the human being shown in FIG. 7 showing the apparatus of the present invention introduced into the preperitoneal space.

FIG. 9 is a view similar to FIG. 8 but showing the sleeve removed from the apparatus and with the balloon inflated.

FIG. 12 is an isometric view of a patch incorporating the present invention.

FIG. 13 is a side elevational view of the patch shown in FIG. 12.

FIG. 14 is an isometric view showing the patch in FIGS. 12 and 13 in a rolled-up, generally cylindrical configuration.

FIG. 15 is a sagittal view showing the hernia sac of hernia that is to be repaired.

FIG. 16 is a sagittal view showing the introducer through which the rolled-up patch in FIG. 17 has been introduced into the preperitoneal space by an introducer rod.

FIG. 25 is an isometric view of another embodiment of a balloon and patch for use with the apparatus of the present invention.

FIG. 26 is a rolled-up cross-sectional view of the balloon and patch shown in FIG. 25.

FIG. 27 is an isometric view of another embodiment of a patch for use with the apparatus of the present invention.

FIG. 28 is an isometric view of the patch shown in FIG. 27 wrapped in an introducer assembly.

FIG. 29 is a top plan view of another embodiment of a laparoscopic apparatus incorporating the present invention.

FIG. 30 is a side elevational view taken along the line 30—30 of FIG. 29.

FIG. 31 is a cross-sectional view taken along the line 31—31 of FIG. 30.

FIG. 32 is a cross-sectional view taken along the line 32—32 of FIG. 30.

FIG. 41 is a side elevational view of the assembly shown in FIG. 39.

FIG. 42 is a top plan view looking along the line 42—42 of FIG. 41.

FIG. 43 is a view partly in cross section taken along the line 43—43 of FIG. 42.

FIG. 44 is a view looking along the line 44—44 of FIG. 41.

FIGS. 49A–49G are cartoons showing use of the surgical dissector shown in FIG. 1 in a laparoscopic hernia procedure.

FIG. 56 is a side elevational view of another embodiment of a laparoscopic apparatus incorporating the present invention showing the balloon in a collapsed condition and packaged in a roll.

FIG. 57 is a side elevational view of the obturator shaft utilized as a part of the laparoscopic apparatus shown in FIG. 56.

FIG. 57A is an enlarged partial cross-sectional view of the distal extremity of the obturator shaft shown in FIG. 57.

FIG. 57B is a view similar to FIG. 57A for use with a laparoscope having a centrally disposed lens for viewing.

FIG. 58 is an isometric view of the apparatus shown in FIG. 56 with the balloon inflated but in a rolled out condition.

FIG. 59 is a cross-sectional view taken along the line 59—59 of FIG. 58.

FIG. 60 is an isometric view showing the manner in which a sheet of non-elastomeric material is utilized to form the balloon of the present invention shown in the embodiments in FIGS. 58 and 59.

FIG. 61 is an isometric view similar to that shown in FIG. 60 but showing another subsequent step for making the balloon of the present invention.

FIG. 62 is another isometric view similar to FIGS. 60 and 61 showing still another step in making the balloon of the present invention.

FIG. 63 is a cross-sectional view taken along the line 63—63 of FIG. 56.

FIG. 64 is a cross-sectional view of a balloon incorporating the invention showing the balloon provided with laterally and inwardly extending folds.

FIG. 65 is a schematic illustration of a balloon dissection apparatus incorporating the present invention which can be utilized in connection with dissecting around an obstruction.

FIG. 66 is a plan view showing the bifurcated balloon in FIG. 65 partially unrolled.

FIG. 67 is a plan view illustrating the balloon in FIG. 66 having one of its legs everting around an obstruction.

FIG. 68 is a plan view illustrating the balloon in FIG. 66 having both legs of the bifurcated balloon everted to create dissection around the obstruction.

FIG. 71 is a plan view showing another embodiment of a laparoscopic apparatus incorporating the present invention.

FIG. 72 is a side elevational view taken along the lines 72—72 of FIG. 71.

FIG. 73 is an enlarged partial cross-sectional view of a portion of the apparatus shown in FIG. 71.

FIG. 74 is a plan view partially in cross-section showing another embodiment of the laparoscopic apparatus incorporating the present invention.

FIG. 79 is an isometric view of the tunneling member removed from the FIG. 75 laparoscopic apparatus illustrating the open distal end in accordance with the invention.

FIG. 80 is a side elevational view partially in cross-section that illustrates the distal end of a conventional laparoscope extending outside the distal end of the tunneling member according to one aspect of the invention.

FIG. 81 is a cross-sectional view taken along line 81—81 in FIG. 75 that illustrates a rolled up balloon with integral balloon cover according to the invention.

FIG. 87 is an isometric view of another embodiment of the invention that accepts a conventional laparoscope, and permits unobstructed visualization during laparoscopic surgical procedures as described herein.

FIG. 88 is an isometric view of the tunneling member of the FIG. 87 embodiment according to aspects of the present invention, illustrating a laparoscope inserted through the central bore of the member, and illustrating the features associated with the open ended distal portion of the member.

FIG. 89 is an isometric view of the FIG. 87 embodiment that illustrates the insertion of a conventional laparoscope into the apparatus to permit unobstructed laparoscopic viewing.

FIG. 109 is a cross-sectional view of still another tunneling apparatus in accordance with the present invention.

FIG. 109A is an enlarged partial cross-section view of the apparatus of FIG. 109.

DETAILED DESCRIPTION OF THE DRAWINGS

Figure 10:
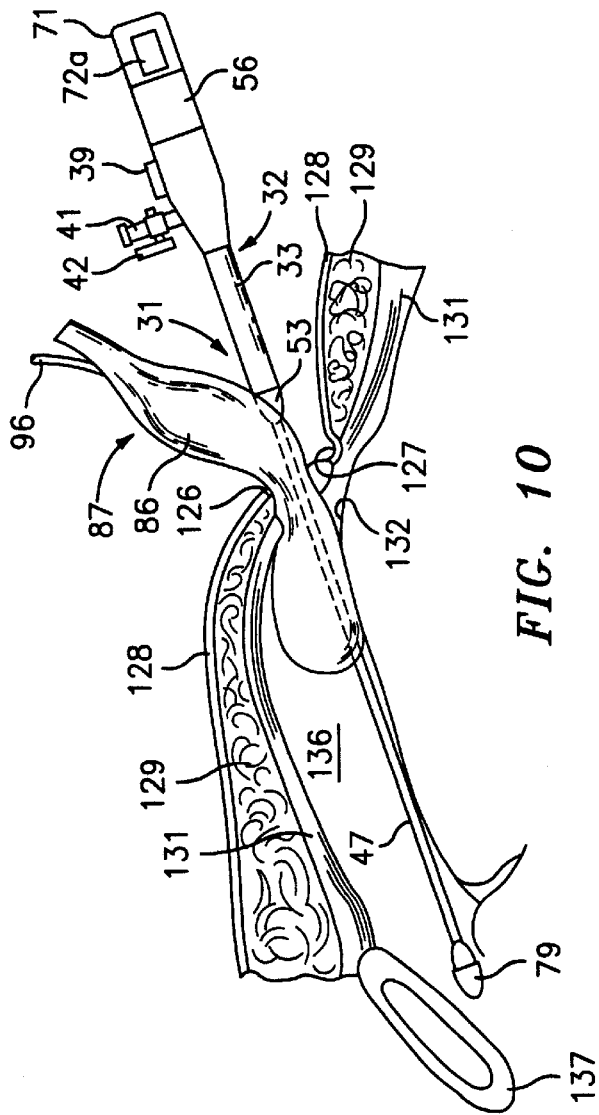
FIG. 10 is a sagittal view similar to FIG. 8 showing the balloon deflated and being removed.

In general, the apparatus of the present invention is used for insertion into a body to create an anatomic space. In one embodiment of the invention, the apparatus is comprised of a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. An inflatable balloon is provided. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

More in particular, as shown in the drawings, the apparatus or device 31 for creating such an anatomic space for use in a laparoscopic procedure (see FIG. 1) includes an introducer sleeve 32 which consists of a tubular member 33 formed of a suitable material such as plastic which is provided with a bore 34 extending throughout the length thereof. A handle section 36 is mounted on one end of the tubular member 33 and is also formed of a suitable material such as plastic. It is provided with a bore 37 which is in communication with the bore 33. A flapper valve 38 is mounted within the handle section 36 and is movable between a position in which it closes off the bore 37 and a position out of the way of the bore 37 by a finger operated actuator 39 mounted on the exterior of the handle section 36. A stopcock 41 is mounted on the handle section 36 and is in communication with the passage 37. A lever 42 is provided for opening and closing the stopcock 41.

A tunneling shaft assembly 46 is slidably mounted in the bores 37 and 34 of the introducer sleeve 32. The tunneling shaft assembly 46 consists of a tunneling shaft or rod 47 formed of a suitable material such as stainless steel, of a suitable length, as for example 18 inches, and a suitable diameter of approximately ⅛ inch. The tunneling rod 47 is provided with proximal and distal extremities 48 and 49.

An introducer member 51 is slidably mounted on the tunneling shaft or rod 47 and is formed of a suitable material such as plastic. The introducer member 51 is substantially hollow as shown and is provided with a bore 52 through which the tunneling shaft 47 extends. The introducer member 51 is provided with a substantially hemispherical tip 53 to form a rounded protrusion or first obturator through which the rod 47 extends. The introducer member 51 has a length such that when it is introduced into the bore 34 of the introducer sleeve 32, it extends out of the distal extremity of the introducer sleeve 32, as shown particularly in FIG. 1. This diameter of the introducer member 51 is sized so that it can be slidably mounted in the bore 34. The other end of the introducer member 51 is provided with a chamfer 54.

A disk-type seal 43 having a central opening is provided in the handle section 36 in alignment with the bore 37, and is adapted to permit the introduction of the introducer member 51 therethrough.

The handle section 36 forms one part of a three-piece handle 56 of the laparoscopic apparatus 31 which is sized so that it is adapted to be grasped by the human hand. As can be seen particularly in FIG. 4, the handle 56 is generally rectangular in cross-section. The handle 56 is provided with an intermediate section 57 which has a bore 58 extending therethrough in registration with the bore 37 and has the same general diameter as the bore 37 so that the introducer member 51 can travel therethrough. The sections of the handle 56 can be characterized as having first, second and third sections, in which section 36 is the first section and intermediate section 57 is the second section. A latch is provided for interconnecting the intermediate section 57 to the first section 36, and consists of a pair of oppositely disposed latches 61 pivotally mounted on the pins 62 in the intermediate section 57. Each of the latches 61 is provided with a latch portion 63 adapted to engage a protrusion 64 provided on the first section 36, and is yieldably urged into engagement therewith by a spring 66. Each of the latches is provided with a cam surface 67 which is adapted to be engaged by the chamfer 54 of the introducer member 51 to cam the latch portion 63 out of engagement with the protrusion 64 to release the intermediate section 57 from the first section 36 for a purpose hereinafter described.

The handle 56 also consists of another section 71, which can also be characterized as the third section, which is secured to the proximal extremity of the tunneling shaft or rod 47. A pair of latches 72 are provided in the section 71 and are pivotally mounted on pins 73. The latches 72 are provided with latch portions 74 adapted to engage projections 76 provided in the intermediate section 57. Means is provided for yieldably retaining the latches 72 in engagement with the projections 76 and consists of a U-shaped spring 77 mounted within the end section 71 and engaging the latches 72. The latches 72 are provided with knurled portions 72a which extend outwardly and which are adapted to be grasped by the fingers of the hand so that the latch portions 74 can be moved out of engagement with the projections 76 against the force of the spring 77.

The tunneling shaft assembly 46 also includes a tunneling member or tip 79 which is mounted on the distal extremity of the tunneling shaft or rod 47. As shown, the tip 79 is substantially olive-shaped and can also be called a second obturator. It is provided with a rounded hemispherical surface on its distal extremity which has a maximum diameter of slightly less than the diameter of the bores 34 and 37 so that it can pass through the introducer sleeve 32. The proximal extremity of the tip 79 is of smaller diameter to provide an annular step 81 in the tip. The proximal extremity of the tip 79 is also hemispherical, as shown. The tunneling member or tip 79 can be formed of a suitable material such as plastic and can be secured to the distal extremity of the tunneling shaft or rod 47 by suitable means such as an adhesive. As hereinafter explained, the tunneling shaft or rod 47 is movable so that the tip 79 can be brought into engagement with the hemispherical end 53 of the introducer member 51 for a purpose hereinafter described.

The laparoscopic apparatus 31 also includes a balloon assembly 86 which is shown in FIGS. 2, 5 and 6. As shown in FIG. 5, the balloon assembly 86 consists of a balloon 87 which, when deflated, has a pear-shaped configuration when viewed in plan. The balloon 87 is preferably formed of a non-elastomeric, medical-grade material of a suitable type such as PVC. Thus, the balloon 87 can be formed of two sheets 88 and 89 of such a material which have their outer margins bonded together by suitable means such as by a heat seal 91 extending around the perimeter of the flat balloon 87. The balloon 87 is provided with a neck 94 into which a flexible tubular member 96 extends, and is secured therein in a suitable airtight fashion such as by an adhesive. The tubular member 96 is provided with a lumen 97 which is in communication with the interior of the balloon 87 and which can be used for inflating the balloon 87 through a Luer-type fitting 98 mounted on the free end of the tubular member 96.

Means is provided for removably securing the balloon 87 to the tunneling rod or shaft 47, and consists of a sleeve 101 formed of the same material as the balloon 87, and which can be formed integral or separate therefrom and adhered thereto by suitable means such as an adhesive. The sleeve 101 extends longitudinally of the balloon 87 and is disposed generally equidistant from the side margins of the same. The sleeve 101 is provided with a passage 102 extending therethrough which is sized to slidably accommodate the tunneling shaft or rod 47. Means is provided for permitting separation of the balloon 87 from the tunneling rod by movement sidewise from the axis of the passage 102 and takes the form of longitudinally spaced apart perforations 103 in the sleeve 101 extending longitudinally the length of the sleeve 101. The perforations 103 are spaced close enough together to form a weakened region so that the balloon can be readily separated from the tunneling rod by separating the plastic sleeve 101 by tearing the plastic between the perforations as hereinafter described.

As shown in FIG. 6, the sleeve 101 is disposed equidistant from the side margins of the balloon 87, permitting the balloon 87 to be inflated as hereinafter described and as also shown by the dotted lines in FIG. 6, to be inflated around the rod 47. When deflated, the side margins of the balloon 87 can be rolled inwardly toward the rod 47 as shown by the broken lines in FIG. 6 to permit the same to be folded into a generally cylindrical configuration as shown in FIG. 2, and to be enclosed within a removable sleeve 106 carried by the tunneling shaft or rod 47. The removable sleeve 106 is formed of a relatively thin-walled tubular member 107 of a suitable material such as Teflon which has a weakened region 108 in its wall extending longitudinally the length thereof. This weakened region 108 can take the form of a slit as shown, or can be a series of perforations or slots formed in the wall, or a combination thereof. The proximal extremity of the tubular member 107 is provided with split-apart or separable end portions 107a and 107b to which are secured finger rings 109 of a suitable material such as plastic and secured thereto by fasteners 111.

Operation and use of the laparoscopic apparatus in performing the method for laparoscopic hernia repair through a preperitoneal space may now be briefly described as follows. Let it be assumed that the laparoscopic apparatus 31 has been assembled as shown in FIG. 1. As shown in FIG. 7, let it be assumed that a human patient 121 is in a prone position and has a hernia 122 in the lower abdominal area which he wishes to have repaired. The patient is prepared in an appropriate manner by administering a suitable anesthesia, as for example a spinal anesthesia, and any other necessary preparation. The surgeon first makes an infraumbilical incision 126 in the skin below the navel or umbilicus 127 and separates the fat 129 and then incises the anterior rectus sheath or fascia 131 in the midline. Care should be taken not to penetrate the peritoneum 132 overlying the abdominal cavity 133 (see FIG. 8).

After the incision 126 has been made in the manner hereinbefore described, the laparoscopic apparatus 31 is then taken by one hand of the surgeon, grasping the handle 56 and utilizing the other hand to facilitate the insertion of the rounded blunt tip 79 into the incision 126. The blunt tip 79 is caused to enter the slit in the fascia 131 and pass anterior to the peritoneum 132, in between the rectus muscles (laterally), and enters the potential preperitoneal space 136. The blunt tip 79 is then utilized as a tunneling device by the surgeon using one hand 56 to advance the blunt end 79 toward the pubic region of the patient 121 while the surgeon places his other hand on the abdomen to feel the apparatus or device 31 as it is being advanced. The advance of the device 31 is continued until the blunt tip 79 is below the symphysis pubis 137 as shown in FIG. 8, and preferably is disposed between the symphysis pubis 137 and the bladder 138.

After the apparatus or device 31 has been properly positioned as shown in FIG. 8, the removable sleeve or sheath 106 is removed by the surgeon using one hand to engage the finger rings 109 which are exterior of the body of the patient and outside of the incision 126. At the same time, the other hand of the surgeon is utilized to stabilize the portion of the device 31 which is within the preperitoneal space. The sheath 106 can be readily withdrawn since it is formed of Teflon and is split or weakened along its length, by pulling it proximally and away from the longitudinal axis of the tubular member 33. As the sheath 106 opens and slips off, it exposes the balloon 87 of the balloon assembly 86. When the sheath 106 is completely removed, a sterile saline solution serving as a balloon inflation medium is introduced into the balloon 87 through the tubular member 96 by connecting a conventional syringe 141 to the Luer fitting 98. The balloon 87 typically can be inflated to a suitable size by introducing 500 cc or less of normal saline solution into the balloon 87 by pressing on the plunger 142. As the balloon 87 is inflated, the balloon 87 progressively unwraps with its side margins rolling outwardly from the center while expanding into a plane to cause progressive separation or dissection of tissue (i.e. 131, 132) along its weakest points by application of forces generally perpendicular to the plane of the balloon 87 to create the preperitoneal or anatomic space. The balloon 87 expands around the tunneling shaft 47 in the manner shown in broken lines in FIG. 6 to achieve the progressive separation until complete inflation is achieved. The surgeon can sense the filling of the balloon 87 by feeling the abdomen of the patient 121 as the balloon 87 is inflated. The balloon 87 serves to open up the preperitoneal space 136 to provide a bloodless space for the procedures hereinafter to be performed. Since the balloon 87 is formed of a non-elastomeric material, it is a volume-limited balloon to prevent over expansion. Different sizes of balloons can be utilized for different patient sizes. With a smaller balloon it is possible to deflate the balloon and then shift the balloon and again reinflate it to obtain the desired bloodless preperitoneal space.

After the desired bloodless anatomic space or pocket 136 is formed, the balloon 87 is deflated by withdrawing the normal saline solution by withdrawal of the plunger 142 of the syringe 141 or via a hospital vacuum aspirator. After the balloon 87 has been deflated, the balloon assembly 86 can be removed by grasping the handle 56 of the laparoscopic apparatus or device 31 with one hand and using the other hand to grasp the tubular member 96 and the proximal extremity of the balloon 87 and to remove the same through the incision 126, as shown in FIG. 10. As the balloon 87 is being removed, it is progressively separated from the tunneling rod or shaft 47 by causing the sleeve 101 to split apart along the longitudinal perforations 103 provided in the sleeve 101. This makes it possible to separate the balloon 87 from the tunneling rod 47 without the necessity of removing the tunneling rod 47 or the introducer sleeve 32.

Figure 11:
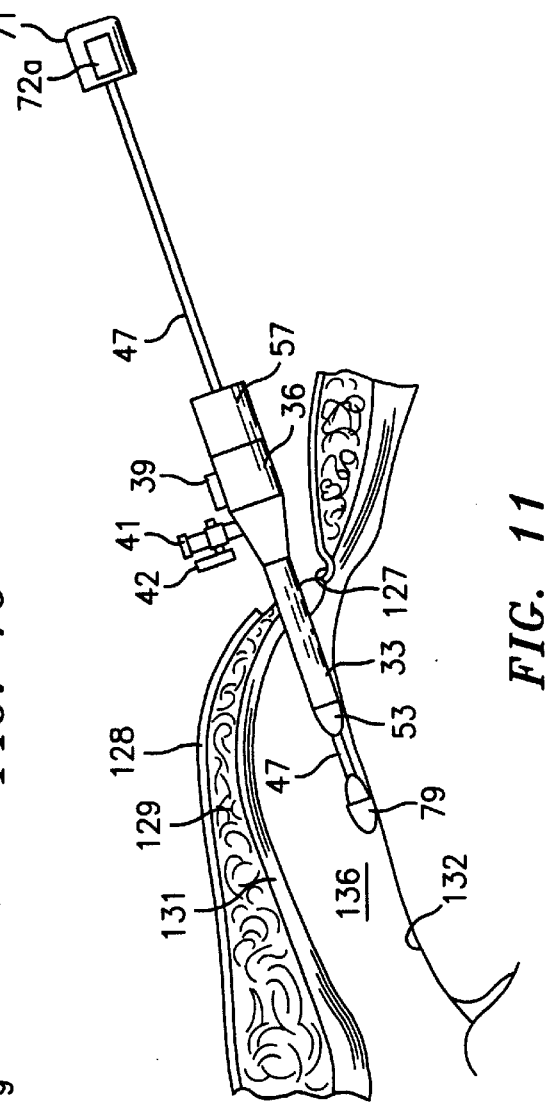
FIG. 11 is a sagittal view similar to FIG. 8 showing removal of the tunneling shaft.

After the balloon assembly 86 has been removed, the introducer device 32 can be advanced distally over the tunneling shaft or rod 47 so it extends well into the preperitoneal space 36 as shown in FIG. 11. The third section 71 of the handle 56 is then released by depressing the latches 72 by engaging the portions 72a to disengage the latch portions 74 from the intermediate section 57 of the handle 56. The third section 71 is then withdrawn proximally as shown in FIG. 11 to bring the olive-shaped tip 79 into engagement with the distal tip 53 of the introducer member 51 to cause both the tip 79 and the introducer member 51 to be withdrawn or retracted. As the introducer member 51 is being withdrawn, its chamfer 54 will strike the cam surfaces 67 of the latches 61 to cause them to disengage from the handle section piece 36 to carry it along with the introducer member 51 and shown in FIG. 2. Thus, it can be seen that the tunneling shaft assembly 46 can be readily removed merely by one motion of the surgeon's hand. Thereafter, a conventional laparoscope 144 (see FIG. 16) can be introduced through the introducer sleeve 32 to permit the surgeon to view the dissected preperitoneal space 136.

The dissected preperitoneal space 136 is then insufflated with carbon dioxide through the stopcock 41 to a pressure ranging from 6 to 8 mm of mercury. Thereafter, two additional trocars 146 and 147 are introduced through the abdominal wall into the dissected preperitoneal space 136 in appropriate locations. Thus, as shown in FIG. 7, trocar 146 is introduced into the left side of the abdomen of the patient 121 below the introducer sleeve 32 and the trocar 147 is introduced into the dissected preperitoneal space 136 immediately above the symphysis pubis 1 37 and directly below the introducer sleeve 32. As can be appreciated, the locations of the trocars 146 and 147 are generally dictated by the location of the hernia 122 to be repaired.

A patch 151 of the present invention to be utilized in the hernia repair procedure is shown in detail in FIGS. 12, 13 and 14. The patch 151 can be characterized as a hernia patch or graft and is made of a suitable plastic mesh such as a Prolene mesh manufactured by Ethicon, Inc. The patch 151 can be of any desired configuration. For example it can be generally circular as shown, and consists of a disk 152 of a suitable diameter, as for example 2 inches. A tail 153 is secured to the disk substantially in the center thereof, in a suitable manner. For example, as shown, the tail 153 can be provided with split portions 153a and 153b which are split apart and offset with respect to each other. The split portions 153a and 153b are secured to a smaller reinforcing disk 154 formed of the same material as disk 152 and secured to the disk 152 by suitable means such as surgical thread (not shown). The tail 153 may be formed of the same material as the disk 152 and 154, or it can be formed of a different material, such as Goretex. It can have a size such that it has a width of approximately ½ inch and a length of approximately 1 ½ inches. As shown particularly in FIG. 14, the side margins of the disk 152 can be rolled inwardly towards the center adjacent the tail 153 to form a cylindrical roll 156 with the tail 153 extending outwardly therefrom. The roll 156 can be maintained in its rolled-up condition by means of sutures 157 disposed adjacent opposite ends of the roll and on opposite sides of the tail 153.

Referring now to FIGS. 15 and 16, conventional laparoscopic instruments, introduced through trocars 146 and 147, are used to repair the hernia 161 by placement of the patch 151. First, the laparoscopic instruments are introduced through the introducer device 32 while being observed through laparoscope 144 to dissect the hernia 161. The hernia neck 162 may be observed as it is entering the internal inguinal ring 163. The repair procedure starts by dissecting the hernia sac 161 from the surrounding tissue (spermatic duct and vessels) (see FIG. 15). The process is facilitated by $CO_2$ pressure impinging on the neck 162 of the hernia sac 161. As soon as this dissection is completed, the roll 156 is pushed into the trocar 147 and advanced through the same by suitable means such as a deployment rod 164 (see FIG. 16) to enter the dissected preperitoneal space 136 as shown in FIG. 16. Alternatively, the roll 156 can be placed in a tubular member (not shown) which can be used to position the roll 156 within the trocar 157. Thereafter, by the deployment rod 164, the roll 156 can be pushed out of the tubular member into the dissected preperitoneal space 136.

Figure 17:
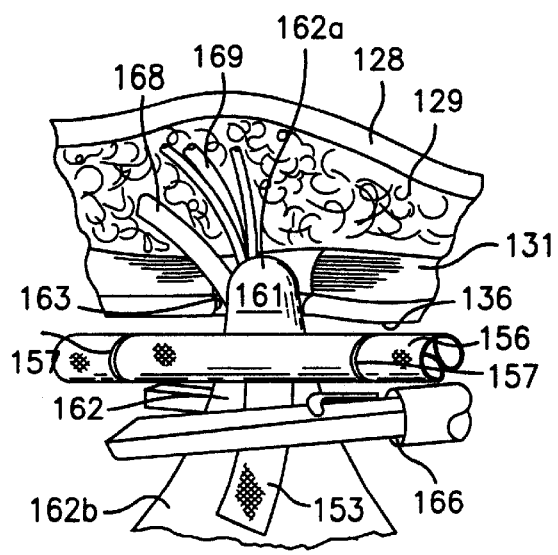
FIG. 17 is a sagittal view similar to FIG. 16 showing the attachment of the patch to the hernia sac.
Figure 18:
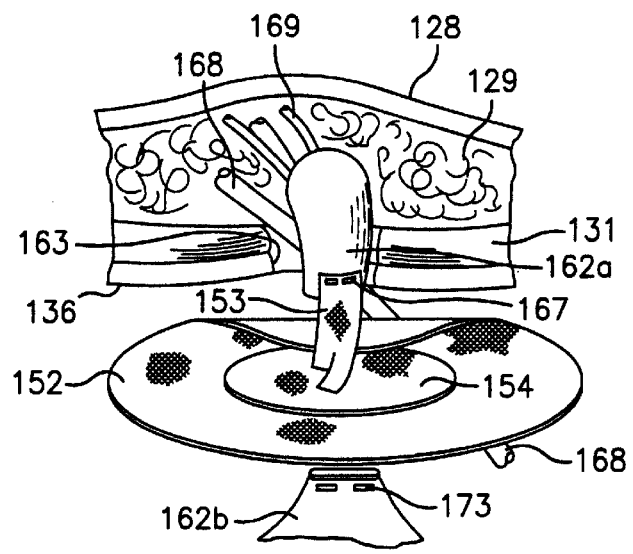
FIG. 18 is a sagittal view similar to FIG. 17 showing the dissection of the hernia sac and the unrolling of the patch.
Figure 19:
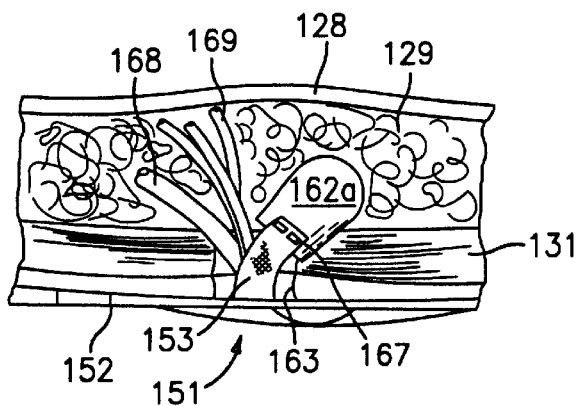
FIG. 19 is a sagittal view showing the patch in place to provide the hernia repair.

The roll 156, after it is in the preperitoneal space 136, is then manipulated so that its tail 153 is disposed alongside the neck 162 of the hernia sac 161 as shown in FIG. 17. With reference to FIG. 17, a conventional stapling device 166 is then introduced through the trocar 146 to staple the tail 153 to the neck 162. The staples 167 serve to divide the neck 162 of the sac 161 into distal and proximal portions 162a and 162b. As soon as this stapling operation is completed, the two portions 162a and 162b are separated from each other because of the pressure of the insufflation gas to cause the tail 153 of the patch 151 to be pulled upwardly into the inguinal ring to pull with it the disk 152. The sutures 157 are cut apart to permit the disk 152 to unroll and to be placed across the inguinal ring 163 which created the main weakness in the abdominal wall permitting the hernia which is being repaired to occur. The proximal portion 162b of the neck 162 is stapled together by staples 1 73 as shown in FIG. 18. The proximal portion 162 is then permitted to fold back into the desired anatomical location within the abdomen.

Thereafter, while observing the procedure under the laparoscope, the dissected preperitoneal space 136 can be deflated by permitting the carbon dioxide gas to escape to the atmosphere through the stopcock 41 in the introducer device 32 by operation of the stopcock lever arm 42. As deflation is taking place, the movement of the patch 151 is observed through the laparoscope 144 to ensure that it does not become misplaced. When the deflation is complete, the patch 151 is in a position over the inguinal ring 163 and serves to provide reinforcement to prevent the occurrence of another hernia in that area. The tail 153 is disposed within the inguinal ring 163 and retains the mesh disk 152 so that it surrounds the inguinal ring 163.

After deflation is complete, the trocars 146 and 147 as well as the introducer device 32 can be removed. Small sutures can then be utilized to close the various small openings which have been made in the abdominal wall so that upon healing there will be minimal noticeable scars after healing. The scar in the navel or umbilicus typically is almost nearly invisible.

It has been found that the use of the laparoscopic apparatus 31 in accomplishing the method as hereinbefore set forth provides a procedure in which the pain after the operation is markedly reduced. This is particularly true since the operation does not involve suturing of any ligaments which typically produces the pain. In addition, the recovery time for the patient is greatly accelerated. In the procedure of the present invention, a patient can return to work within a matter of 3 to 5 days rather than in a number of weeks as in a conventional hernia repair procedure. The procedure also has other advantages. For example, there is a lack of necessity for a general anesthesia. Another principal advantage of the procedure is there is no contact of mesh patch 151 with the intestines of the patient or other intra-abdominal structures, thus greatly reducing the possibility of adhesion formation. In addition, the graft which is formed by the patch 151 is more secure and is positioned in an anatomically correct position. This is because the hernia sac is in exact alignment with the hernia and pulls with it the tail 153 of the graft to ensure that the graft formed by the patch 151 is drawn into the correct position and is maintained in that position to prevent migration. In addition, the graft, by having an additional central disk 154, ensures that additional reinforcement is provided in the proper location in the center where the weakest region in the abdominal wall has occurred. In addition, by such proper centering, the mesh construction of the patch 151 serves to uniformly reinforce the area surrounding the hernia.

Figure 20:
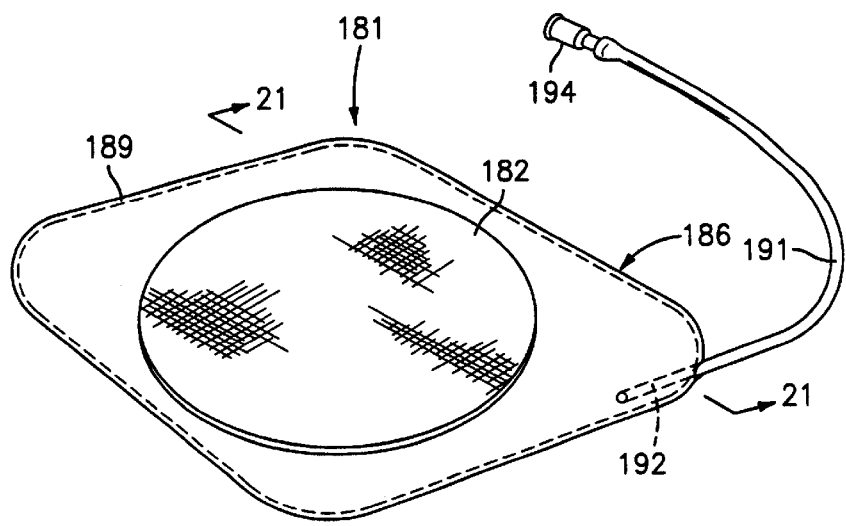
FIG. 20 is an isometric view of another embodiment of a balloon with a patch disposed thereon for use with the apparatus of the present invention.
Figure 21:
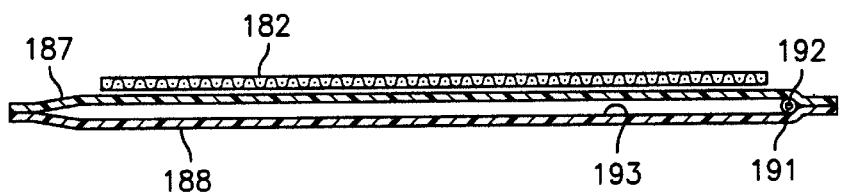
FIG. 21 is a cross-sectional view taken along the line 21—21 of FIG. 20.
Figure 22:
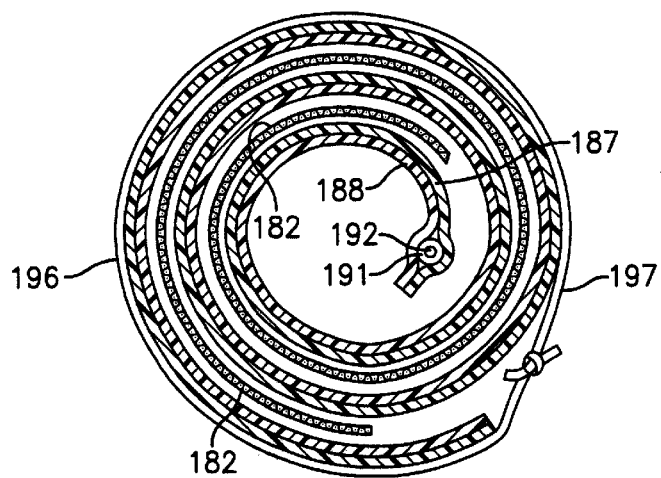
FIG. 22 is an enlarged cross-sectional view taken along the line 22—22 of FIG. 23.

Another embodiment of the present invention is shown in FIGS. 20, 21 and 22 with respect to another embodiment of a balloon assembly 181 and another embodiment of a patch or graft 182. The balloon assembly 181 consists of a balloon 186 formed of two sheets 187 and 188 which are rectangular in shape, as for example square as shown in FIG. 20, which are heat-sealed together at their outer margins as indicated by the broken line 189. A tubular member 191 is provided which has one end sealed into one corner of the balloon 186 as shown in FIG. 20. The tubular member 191 is provided with a lumen 192 which opens up into the interior space 193 of the balloon. The sheets 187, 188 are formed from a non-elastomeric material of the type hereinbefore described. A Luer fitting 194 is connected into the free end of the tubular member 191 and is utilized for introducing a saline solution into the balloon 186 for inflating the same.

The graft or patch 182 can have a desired configuration, as for example circular as shown in FIG. 20. It is formed of a non-absorbable synthetic surgical mesh, as for example from polypropylene manufactured by Ethicon Inc. As shown, the mesh patch 182 overlies the sheet 187.

Figure 23:
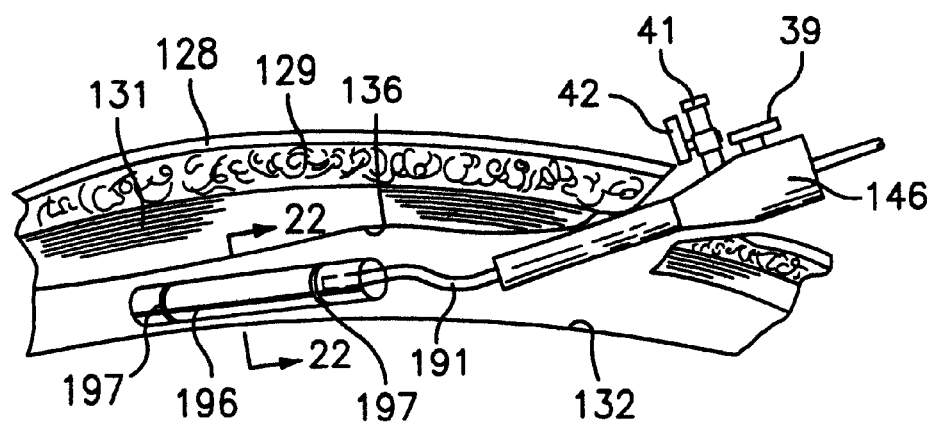
FIG. 23 is a sagittal view showing the manner in which the balloon and patch shown in FIG. 20 are disposed in the preperitoneal space.
Figure 24:
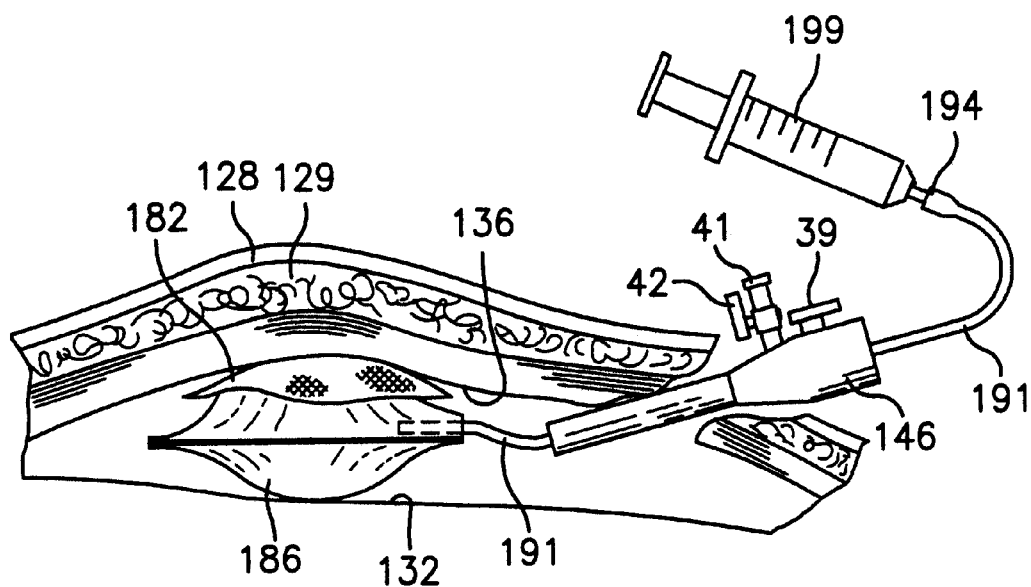
FIG. 24 is a sagittal view showing the placement of the balloon and the patch of FIG. 20, and the inflation of the balloon in the preperitoneal space.

The balloon assembly 181 already made in Ser. No. 324,519 with the patch 182 thereon can be rolled-up into a roll 196 as shown in FIG. 22 in which the patch or graft 182 is disposed within the roll 196. The roll can be maintained in the roll configuration by sutures 197 wrapped about the same. The roll 196 can then be introduced through a side trocar 146 and introduced into the dissected preperitoneal space 136 with the tubular member 191 extending through the trocar 146 and having its Luer fitting 194 disposed outside of the trocar. After the roll 196 has been introduced, the sutures 197 can be removed and the balloon can be inflated by introducing a saline solution through the fitting 194 by use of a syringe 199. Before the saline solution is introduced to inflate the balloon 186, the roll 196 is properly positioned so that when it is inflated and begins to unroll it will unroll in the proper direction so that the graft or patch 182 carried thereby is properly positioned as shown in FIG. 23. After the roll 196 has been completely unrolled, continued inflation of the balloon 186 moves the patch 182 so that it is pressed against the portion of the fascia through which the hernia has occurred as shown in FIG. 24. As soon as the graft 182 has been properly positioned, the balloon 186 is deflated. The trocar 146 is then removed, and thereafter the balloon can be withdrawn through the opening in which the trocar was present. Thereafter, the gas utilized for insufflation can be permitted to discharge through another trocar so that the fascia 131 comes into engagement with the peritoneum 132 with the large-area patch 182 held in place therebetween. Thereafter, the trocars can be removed in the manner hereinbefore described to complete the procedure.

Another embodiment of a balloon assembly for deploying a large-area patch or graft through a trocar is shown in FIG. 25. The large-area graft 201 shown in FIG. 25 is formed of a mesh material of the type hereinbefore described and has a generally oval-shaped configuration conforming to the general shape of the balloon 202 of the balloon assembly 203. The balloon 202 is constructed of a non-elastomeric material in the manner hereinbefore described. A tubular member 206 is provided for inflating the balloon and has a Luer fitting 207 on the free end thereof. Means is provided for retaining the mesh graft 201 on one side of the balloon and consists of plastic flaps 208 provided on opposite sides of the balloon 202, and secured thereto by a suitable means such as a heat seal along the broken line 209. The inner margins of the flaps 208 are free and are adapted to receive the outer margins of the graft 201 as shown particularly in FIG. 25.

The balloon 202 with the mesh graft 201 thereon can be rolled-up into a substantially cylindrical roll 211 by rolling the outer margins of the balloon inwardly on top of the mesh material to provide two rolls 211 and 212 which are brought in adjacent to each other as shown in FIG. 26 with the mesh graft 201 being wrapped up therewith. The two rolls 211 and 212 can then be inserted into a tubular sheath 214. The sheath 214 can then be introduced through a trocar in a manner hereinbefore described and then the rolls 211 and 212 are pushed out of the sheath 214 into the abdominal cavity. The balloon can then be inflated with a saline solution to cause the two rolls 211 and 212 to unroll in opposite directions and then for the balloon to inflate to move the patch 201 carried thereby into engagement with the portion of the fascia having the hernia therein. Thereafter, the balloon can be deflated, the trocar removed, the balloon removed, and the dissected preperitoneal space deflated so that the large mesh graft 201 is disposed between the fascia and the peritoneum and is retained in position therebetween.

Another embodiment of a graft which can be utilized in connection with the present invention is shown in FIG. 27. The patch or graft 216 is constructed in a manner similar to the graft or patch 151 shown in FIGS. 12 and 1 3, with the exception that it is constructed in a manner so that it can be utilized with a direct hernia rather than an indirect inguinal hernia hereinbefore described. The graft 216 is formed of a sheet of circular mesh in the form of a disk 217 with a reinforcing central disk 218 which has a barbed head 219 secured thereto. The barbed head 219 is formed of a biodegradable material such as polyglycolic acid. The mesh graft 216 can be folded over a deployment rod 221 and introduced into a cylindrical sheath 222 (see FIG. 28) which is sized so that it can be introduced through a conventional trocar, then deployed from the sheath 22 by pushing on the deployment rod 221. After the graft 216 has been deployed into the dissected preperitoneal space 136, it can be positioned in an appropriate manner so that the barb 219 is positioned so that it is in alignment with the inguinal ring whereby upon deflation of the preperitoneal space 136, the barb 219 will extend through the inguinal ring to serve to retain the graft 201 firmly in place.

Another embodiment of a laparoscopic apparatus incorporating the present invention is laparoscopic apparatus 231 as shown in FIGS. 29 through 32. The laparoscopic apparatus 231 includes introducer sleeve or device 32 identical to that hereinbefore described. It also includes a tunneling shaft assembly 46 which is provided with a tunneling shaft or rod 47 and a proximal extremity 49 (see FIG. 32). In the previous embodiment of the laparoscopic apparatus, the tunneling shaft assembly is provided with an olive-shaped or bullet-shaped tip 79 which was secured to the distal extremity 49 of the tunneling shaft 47. In the present embodiment of the apparatus shown in FIGS. 29 through 32, the obturator tip 79a is detachably mounted on the distal extremity 49 of the tunneling rod 47. The proximal extremity of the tip 79a is provided with a slot 236 which extends through one side of the proximal extremity into the central portion of the proximal extremity of the tip 79a. The slot 236 is adapted to receive the rounded extremity 237 provided on the distal extremity 49 of the tunneling rod 47 (see FIG. 32). A removable sleeve 241 is provided as a part of a laparoscopic apparatus 231, and is similar in many respects to the removable sleeve or sheath 106 hereinbefore described. The removable sleeve 241 is formed of a suitable material such as Teflon as hereinbefore described and is provided with a tubular member 242 which is provided with a relatively thin wall 243 that has a weakened portion extending longitudinally thereof in the form of a slit 244 (see FIG. 31). The tubular member 242 is provided with a proximal extremity 246 and a distal extremity 247. The proximal extremity 246 has a thicker cross-section than the distal extremity 247, as shown in FIGS. 31 and 32. The proximal extremity 246 is provided with a recess 248 formed in the wall which is diametrically opposite the slit 244 that serves as a relief region to permit the movable sleeve 241 to be split apart when it is removed from the balloon.

The proximal extremity 246 is provided with wing-like members 251 and 252 which extend diametrically therefrom, spaced 90° apart from the slit 244. These outstretched wings 251 and 252 serve to help the physician orient the laparoscopic apparatus 231 as it is being utilized. The proximal extremity 246 is also provided with a handle 256 which is formed integral therewith and which extends radially from the tubular member 242, The handle 256 is provided with a finger hole 257 extending therethrough through which a finger can be inserted to facilitate pulling the removable sleeve 241 off of the balloon as described in connection with the previous embodiment.

Figure 33:
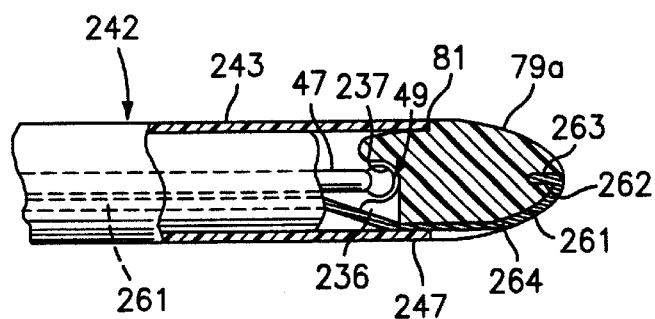
FIG. 33 is an enlarged cross-sectional view of the distal extremity of the laparoscopic apparatus shown in FIG. 29.
Figure 34:
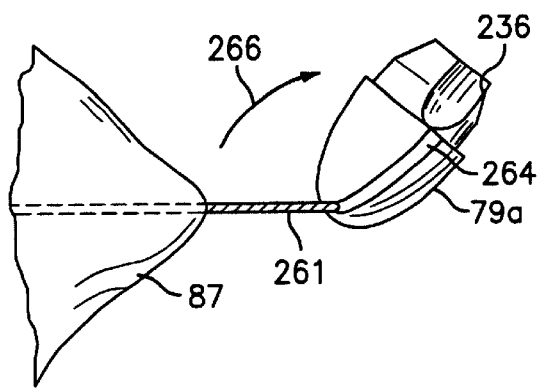
FIG. 34 is a partial plan view showing the balloon after it has been removed from the laparoscopic apparatus with the obturator tip shifting its position.
Figure 35:
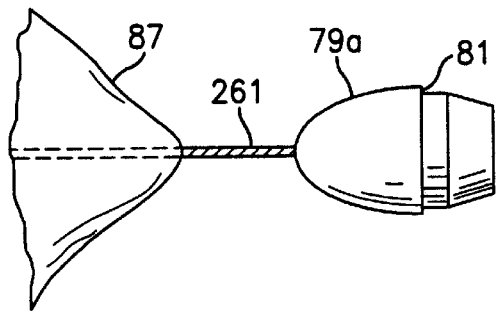
FIG. 35 is a plan view of the balloon shown in FIG. 34 as it is being removed from the body of the patient and bringing along with it the obturator tip.

As shown in FIG. 33, the tip 79a is detachably mounted in the proximal extremity of the removable sleeve 241 so that the tip 79 can serve as a second obturator during introduction of the laparoscopic apparatus 231 as hereinbefore described. Means is provided for securing the detachable tip 79a to prevent it from becoming separated from the laparoscopic apparatus 231 and for permitting its withdrawal after the laparoscopic procedure is being completed. As shown in FIGS. 33 and 34, such means consists of a flexible elongate element 261 in the form of a braided string formed of a suitable fabric such as Nylon, which has one end 262 secured in a slot 263 provided on the distal extremity of the tip 79a by suitable means such as an adhesive (not shown). The flexible elongate element 261 extends from the distal extremity of the tip 79a in a recess 264 opening through the external surfaces of the tip 79a. The proximal extremity of the flexible elongate element 261 can be secured directly to the balloon 87 or, alternatively, it can extend through the perforated sleeve 101 provided in the balloon along the tunneling shaft so that it extends beyond the proximal extremity of the tunneling shaft.

The use of the laparoscopic apparatus 231 in performing a laparoscopic procedure is substantially identical to that hereinbefore described with the exception that when the removable sleeve 241 is removed from the balloon 87, the removable sleeve can be pushed forwardly to detach the tip 79a from the tunneling shaft 47. The removable sleeve 241 then can be pulled rearwardly to separate it from the balloon along the slit 244. As soon as this occurs, the tip 79 becomes free of the sleeve and begins to rotate in the direction of the arrow 266 shown in FIG. 34. When the balloon has been inflated and has performed its functions as hereinbefore described and it is now desired to remove the balloon 87, the balloon 87 can be withdrawn in the manner hereinbefore described, and since the tip 79a is tethered to the balloon 87 itself or flexible elongate element 261 attached thereto extends out proximally of the balloon 87, the tip 79a is withdrawn or can be withdrawn with the balloon 87.

This laparoscopic apparatus 231 with its detachable obturator tip 79a will be useful in certain applications of the present invention. With the previous laparoscopic apparatus hereinbefore described, there is a possibility that when the obturator tip 79 is withdrawn, critical structures, as for example small arteries, may be inadvertently incised between the tip 79 and the distal extremity of the tubular member 33 of the introducer device 32. This possibility is eliminated by having the detachable tip 79a, which is withdrawn when the balloon is withdrawn.

Figure 36:
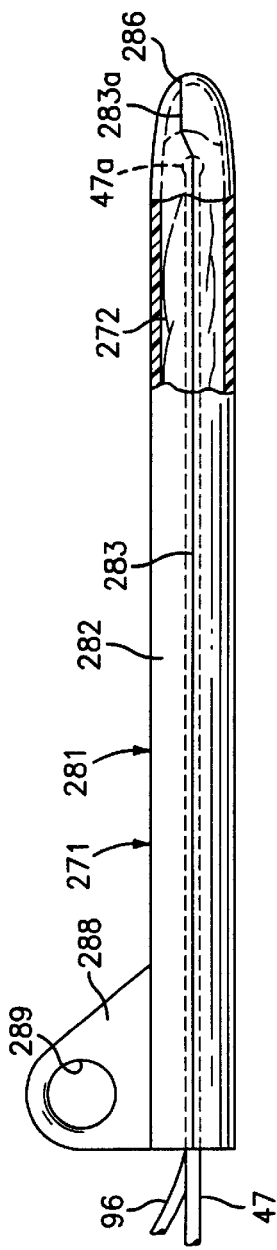
FIG. 36 is a side elevational view of another embodiment of a laparoscopic apparatus incorporating the present invention.
Figure 37:
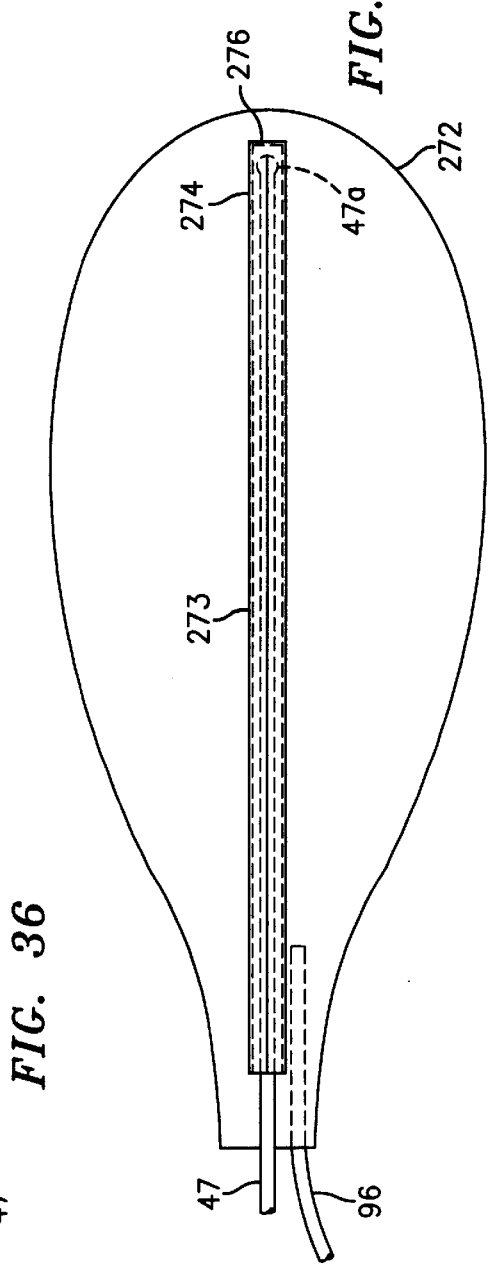
FIG. 37 is a plan view showing the balloon from the apparatus shown in FIG. 36 in an inflated condition and showing the tunneling rod mounted therein being prevented from being advanced beyond the distal extremity of the balloon.
Figure 38:
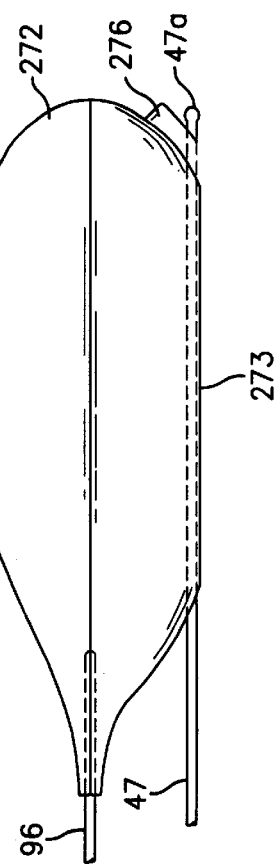
FIG. 38 is a plan view showing the manner in which the balloon is separated from the tunneling rod as it is retracted.
Figure 39:
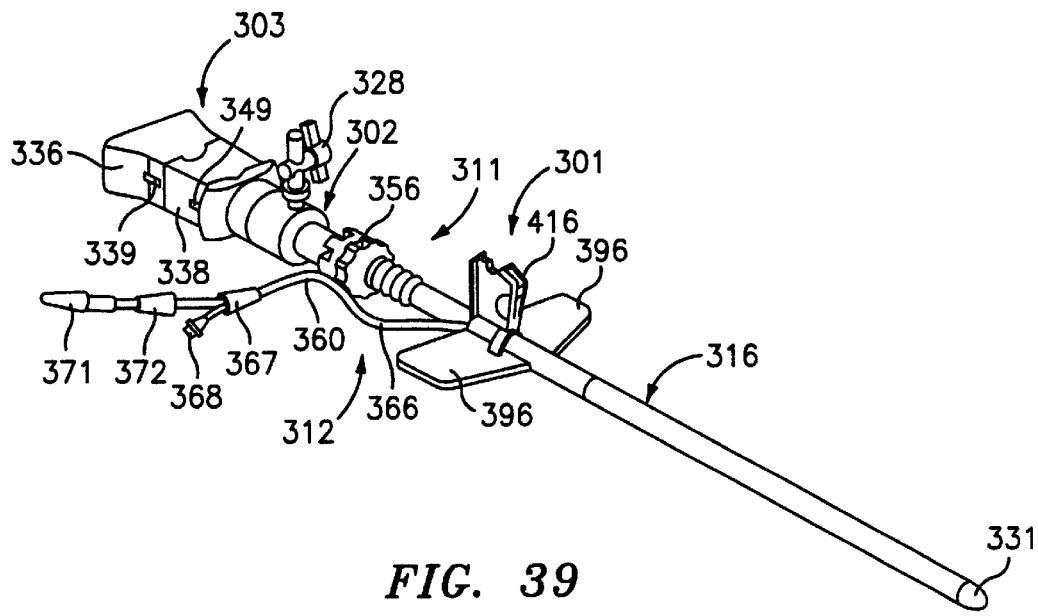
FIG. 39 is an isometric view of a surgical dissector with a cannula incorporating the resent invention in an assembled condition.

Still another embodiment of the laparoscopic apparatus incorporating the present invention is shown in FIGS. 36, 37 and 38, in which the laparoscopic apparatus 271 consists of a balloon 272 of the type hereinbefore described, which is provided with a perforated sleeve 273 through which the tunneling rod 47 extends. The distal extremity 274 of the sleeve is closed by an end piece 276. The balloon 272 is wrapped in the manner hereinbefore described around the tunneling shaft 247. The tunneling shaft or rod 47 is not provided with a tunneling member or second obturator of the type hereinbefore described but its end is rounded as shown by providing a rounded tip 47a.

The wrapped balloon 272 is enclosed within a removable sleeve 281 which is similar to those hereinbefore described. It is provided with a tubular member 282 that has a weakened region in the form of a slit 283 extending longitudinally the length thereof. The removable sleeve 281 differs from those hereinbefore described in that rather than being open at the end as in previous embodiments, it is provided with a closed-end, bullet-shaped or olive-shaped tip 286. The slit 283 is provided with a curved portion 283a which extends through the bullet-shaped tip 286 so that the sleeve can be peeled off of the balloon 272 in the manner hereinbefore described by pulling on the handle 288 having a finger hole 289 therein. During the time that the removable sleeve 281 is being peeled off or separated from the balloon 272, the balloon is held in place by the tunneling rod 47 which engages the end 276 of the perforated sleeve 273. The balloon 272 after it is inflated can be separated from the tunneling rod 47 by pulling on the balloon and causing its distal extremity to lift up and to break apart at the perforations and peel away from the rounded extremities 47a of the tunneling shaft 47 as shown in FIG. 38. Continued pulling on the balloon 272 will cause it to separate from the tunneling rod 47 so that the balloon 272 can be removed as hereinbefore described. Thus, it can be seen that there has been provided an embodiment of the laparoscopic apparatus of the present invention in which the need for an obturator carried by the distal extremity of the tunneling rod 47 has been eliminated by providing the second obturator as a part of the removable sleeve 281. In all other respects, the operation and use of the laparoscopic apparatus 271 is similar to that hereinbefore described.

From the foregoing it can be seen that there has been provided an apparatus and method for developing an anatomic space by the use of a wrapped balloon which, as it is inflated, gradually unwraps to tend to form a plane to cause forces to be created perpendicular to the plane for pulling apart tissue along a natural plane to provide an anatomic space, thereby providing a dissection in the weakest plane creating a more natural, less traumatic and bloodless region in which to perform various medical procedures. Such anatomic spaces can be created in various parts of the human body, for example in the preperitoneal area to provide a space anterior to the peritoneum for hernia repair and for varocele dissection. Spaces can also be developed lateral to the peritoneum and spaces posterior to the peritoneum for performing medical procedures such as a sympathectomy and a lymph node dissection.

As hereinbefore explained, the apparatus and method is particularly appropriate for performing laparoscopic hernia repair, permitting the use of grafts and patches which can be used for direct and indirect hernias with minimal pain to the patient and with the patient being able to return to work within a few days.

Another embodiment of a laparoscopic apparatus 301 incorporating the present invention is shown in FIGS. 39–48. The laparoscopic apparatus 301 can also be described as an assembly in the form of a surgical dissector with a cannula which serves as a hand manipulated surgical instrument that can be used during general surgical laparoscopic procedures to dissect the layers of fascia between the skin and the peritoneum as described in conjunction with the previously disclosed embodiments of the invention. The laparoscopic apparatus 301 consists of a cannula 302 with a tunneling device 303 mounted therein. The tunneling device 303 or guide rod 306 consists of a blunt obturator and an introducer member 307. The laparoscopic apparatus also includes a skin seal assembly 311, a balloon assembly 312 and a balloon cover assembly 316 as shown particularly in FIGS. 39 and 40.

The cannula 302 consists of a cannula tube 321 formed of a rigid plastic having proximal and distal extremities 322 and 323. A flow passage 324 extends from the proximal extremity 322 to the distal extremity 323. A cannula housing or handle 326 is mounted on the proximal extremity by suitable means such by molding it directly thereon. As disclosed in copending application Ser. No. 07/968,201, filed on Oct. 29, 1992, the disclosure of which is hereby incorporated by reference in its entirety, the handle 326 includes first and second valve members (not shown) in which one valve member serves as a duck-bill valve and the other valve member serves as a circular instrument or tool seal. The housing is provided with a Luer-type fitting 327 which is in communication with the interior of the housing outside of the duck-bill valve and is in communication with the passage 324 in the cannula tube 321. As described in copending application Ser. No. 07/968,201, filed on Oct. 29, 1992, the cannula 302 is adapted to receive the tunneling device or blunt obturator device 303 which is generally of the type described hereinbefore in the present application. This device 303 consists of the blunt obturator 306 having a blunt tip 331 which is generally olive-shaped as shown (see FIG. 41) and is formed of a suitable material such as plastic. The olive-shaped tip 331 is molded on the distal extremity 332 of a rod or a shaft 333 formed of a suitable material such as stainless steel. The blunt tip 331 is sized so that its outside diameter is slightly less than the inside diameter of the cannula tube 321. The proximal extremity 334 of the rod or shaft 333 has mounted thereon a handle part 336 of a handle assembly 337 which includes a second handle part 338. The handle parts 336 and 338 are adapted to mate with each other and are detachably connected in a manner described in copending application Ser. No. 07/968, 201 filed Oct. 21, 1992, by the use of latch (not shown) adapted to be actuated by spring-operated latch members 339 disposed on opposite sides of the handle part 336 and adapted to be engaged by the fingers of the hand holding the handle assembly 337. The second handle part 338 forms a part of the introducer device 307 and is mounted on the proximal extremity 341 of an introducer member 342 formed of a suitable material such as plastic. The introducer member 342 is provided with a distal extremity 343 and has a bore 344 extending from the proximal extremity to the distal extremity through an end surface 346 (see FIG. 41) which is inclined at a suitable angle, as for example approximately 45° proximally from the horizontal axis for the bore 344. The bore 344 is sized so it can slidably receive the shaft 333.

The handle part 338 is provided with latch means (not shown) which is adapted to releasably connect the handle part 338 to the cannula housing 326 and includes latch members 349 disposed on opposite sides of the handle part 338 adapted to be engaged by the fingers of the hand holding the handle assembly 337 to permit the handle part 338 to be separated from the cannula housing 326.

The skin seal assembly 311 generally can be of the type described in copending application Ser. No. 08/124,333 filed Sep. 20, 1993, and as described therein consists of a screw body 350 formed of a suitable material such as plastic having a helical thread 351 and a scalloped flange 352. A resilient insert 353 is disposed in the screw body 351 and is formed of a suitable resilient material such as silicone. The insert 353 is provided with a bore 354 extending therethrough. A collet 357 having slots 358 therein surrounds the insert 353 and is engaged by a collar 356 movable axially of the screw body 351 and is adapted to move the collet to compress the insert 353 to move the insert between a retaining position for the cannula tube 321 extending through the bore 354 to retain the cannula 302 in a desired longitudinal position with respect to the skin seal assembly 311 and a releasing position in which the cannula 302 can be slidably moved longitudinally inwardly or outwardly with respect to the skin seal 311. The collar 356 is provided with an annular shoulder 359 having circumferentially spaced-apart slots 360 therein which are used for a purpose hereinafter described. As explained in copending application Ser. No. 08/124,333 filed Sep. 20, 1993, means is provided to restrain rotation of the collar 356 with respect to the collet 357 and includes longitudinally extending keys 355 spaced 180° apart.

Figure 40:
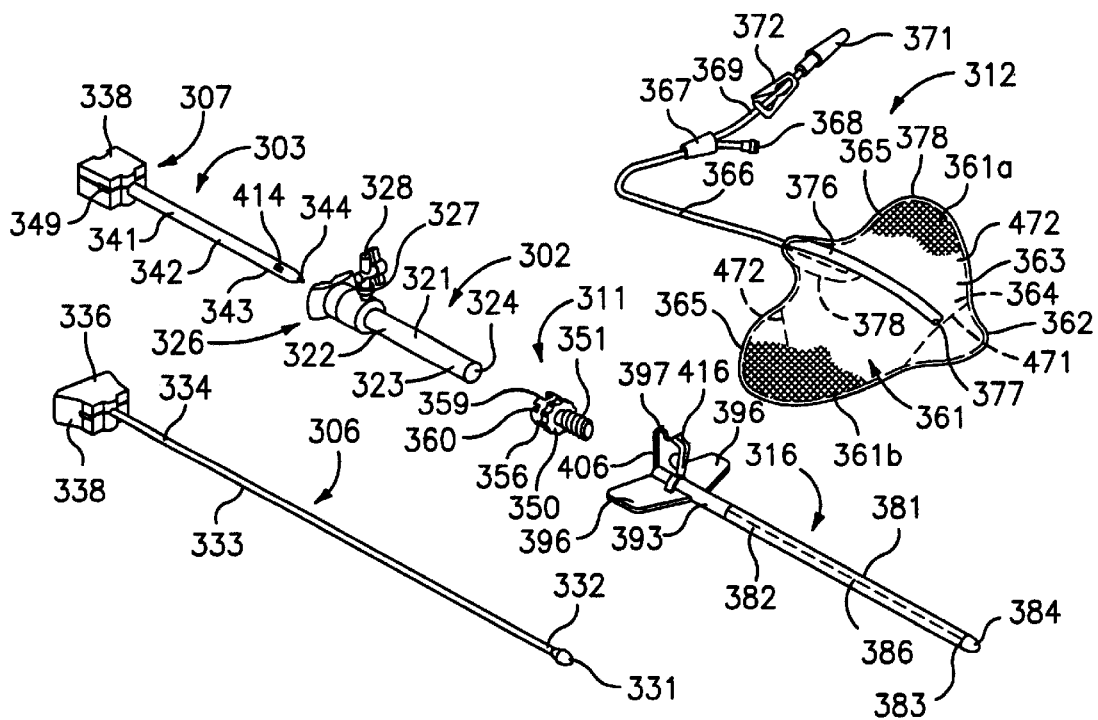
FIG. 40 is an isometric exploded view of the components of the surgical dissector with cannula shown in FIG. 39.
Figure 45:
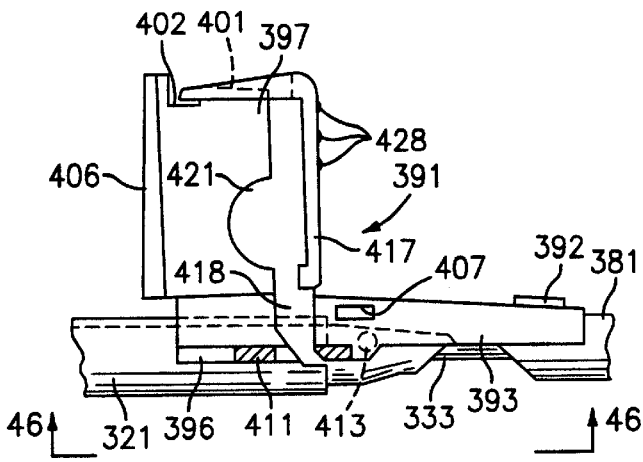
FIG. 45 is a partial side elevational view of the assembly shown in FIG. 1 with the clamping mechanism moved to a release position.
Figure 46:
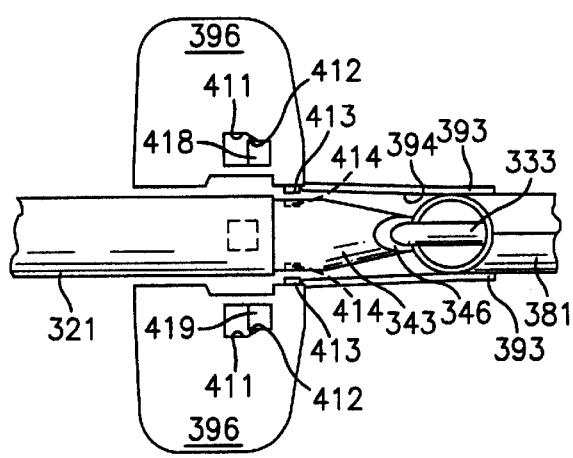
FIG. 46 is a view taken along the line 46—46 of FIG. 45.

The balloon assembly 312 consists of a balloon 361 formed of a non-elastomeric, medical grade plastic material of a suitable type such as polyurethane. The balloon 361 can be characterized as having an asymmetric manta ray configuration when viewed in plan and is provided with a forwardly extending rounded protuberance 362 which has a width substantially less than that of the balloon 361. The balloon 361 consists of two sheets of material which can be identified as a first or upper sheet 363 and a second or lower sheet 364 which have been die cut to the desired configuration with their edges bonded together in a suitable manner such as by means of a heat seal to form a balloon which has a generally flat configuration when deflated as shown in FIG. 40. The upper or outer surface of the first or upper sheet 363 has been roughened in areas 365 as shown in FIG. 40 on the outwardly extending lobe portions 361a and 361b for a purpose hereinafter described. The roughening can be accomplished in any suitable manner such as by embossing the plastic material with a pattern having raised portions therein.

Means is provided for inflating the balloon with a suitable medium, as for example a liquid such as a saline solution and consists of a flexible tube 366 that extends into the balloon between the two sheets 363 and 364 and forms a fluid-tight seal therewith. The interior of the balloon can be inflated and deflated by introduction of the fluid through the tube 366. The tube 366 is connected to a Y-adapter 367 which has one leg of the Y connected to a one-way valve 368 having a Luer fitting and the other leg connected to a tube 369 which is connected to a tapered fitting 371. A conventional pinch off clamp 372 is mounted on the tube 369. The tube 366 is adapted to be releasably retained in the slots 360 of the shoulder 359.

Means is provided for removably securing the balloon 361 to the tunneling rod or shaft 306 and consists of an elongate tubular member or sleeve 376 which extends along the length of the balloon 361 and is disposed on one side of the balloon 361 which can be called the top side generally centrally of the balloon 361. The tubular member 376 is provided with a passage 377 therein through which the tunneling or guide rod or shaft 333 extends. As hereinbefore explained, this tubular member or sleeve 376 can be formed as a separate member which is bonded to the top sheet 363 or alternatively can be formed integral with the top sheet 363 with two heat seals being provided above and below to form the sleeve 376 with the passage 377 therein. The tubular member 376 can be provided with spaced-apart elongate slits or perforations (not shown) extending along a line 378 in the tubular member 376 to facilitate separation of the balloon from the tunneling rod 333 as hereinafter described. With a such a construction it can be seen that the tunneling rod or blunt dissector or obturator 306 overlies the balloon 361 for advantageous features hereinafter described.

The balloon cover assembly 316 consists of a semi-rigid tube 381 formed of a suitable material such as plastic and is provided with proximal and distal extremities 382 and 383. It is provided with a bore 384 (see FIG. 42) which extends from the proximal extremity 382 to the distal extremity 383. The tube 381 is provided with a weakened region in the form of a partial slit 386 extending from the distal extremity 383 to the proximal extremity 382 of the tube 381 on the bottom side of the tube 381 as viewed in FIG. 40 (also see FIG. 42). The tube 381 is provided with a proximal end wall 387 which extends at a suitable angle, as for example 45° proximally with respect to the axis of the bore 384.

Figure 47:
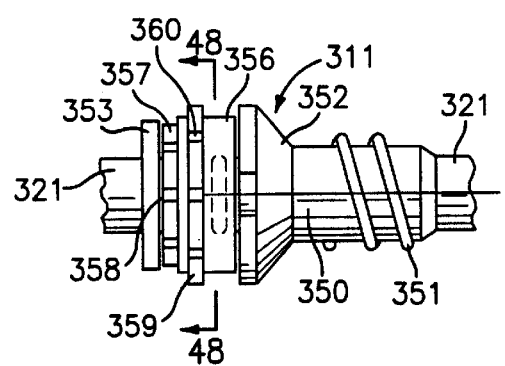
FIG. 47 is a partial side elevational view of an assembly shown in FIG. 41 with the retaining ring moved to a locked position.
Figure 48:
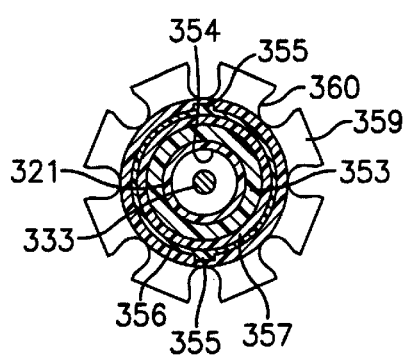
FIG. 48 is a cross-sectional view taken along the line 48—48 of FIG. 47.

The balloon cover assembly 316 also includes a handle 391 which as shown can be formed as a separate part and is secured to the proximal extremity 382 of the tube 381 by a metal clip 392. The handle 391 is provided with a tapered body 393 formed of a suitable material such as plastic which as shown in FIGS. 42 and 47 is open on the bottom side to make accessible a longitudinally extending recess 394 which is semi-circular in cross-section. A pair of sideways extending wings 396 are formed integral with the body 393 and lie in a plane which is substantially coincident with the axis of the semi-circular recess 394. As shown, the wings 396 are disposed at the proximal extremity of the body 393.

An upwardly extending fin 397 is formed on the body 393 substantially equidistant from the wings 396 in a direction generally perpendicular to the plane in which the wings 396 lie. The fin 397 is relatively narrow and is provided with an upper surface 378 having notches 401 and 402 therein. A vertically extending wall 406 is formed as a part of the fin 397 and extends generally in a direction which is perpendicular to the plane of the wings 396. The wall 406 extends in a direction at right angles to the fin 397 and has a gradually increasing thickness from the top to the bottom ends of the wall (see FIG. 46). The body 393 is provided with a pair of spaced-apart holes 407 spaced approximately 90° apart and 45° from each side of the fin 397. An elongate slot 408 is formed in the body 393 and is generally in alignment with the fin 397. A pair of camming slots 411 are provided on opposite sides of the body 393 in the wings 396 adjacent the distal extremities of the wings adjacent the body. The camming slots 411 are provided with inclined camming surfaces 412.

The body 393 is provided with a pair of diametrically disposed protrusions 413 which extend into the recess 394 and which are adapted to seat in a pair of diametrically opposed holes 414 provided in the distal extremity of the introducer member 342.

The balloon cover assembly 316 also includes a clamping member 416 which is provided with a central body 417 and a pair of downwardly extending legs 418 and 419 (see FIG. 43) which extend downwardly into the camming slots 411. As shown, the central body 417 is disposed just distal of the fin 397 and is provided with semi-circular guides 421 formed integral with the central body 417 and disposed on opposite sides of the fin 397 in a fulcrum region which is just slightly above the point of commencement of the legs 418 and 419. The central body 417 is provided with longitudinally extending reinforcing ribs 422 (see FIGS. 43 and 45). It is also provided with a proximally extending latch portion 426 which extends generally at right angles to the central body 417. The latch portion 426 is provided with a centrally disposed slot 427 extending substantially the entire length thereof which receives the upper extremity of the fin 397 so that when the clamping member 416 is snapped into placed over the body 393, the latch portion 426 is disposed in the notch 401 and cannot clear the uppermost portion of the fin 397. The clamping member 416 as hereinafter described is adapted to be moved between positions in which it is disposed within the notch 401 or alternatively in the notch 402. Laterally extending rounded raised portions 428 are provided on the central body 417 are adapted to be engaged by a finger of the hand when moving the clamping member 416 from the notch 401 to the notch 402.

Figure 49E:
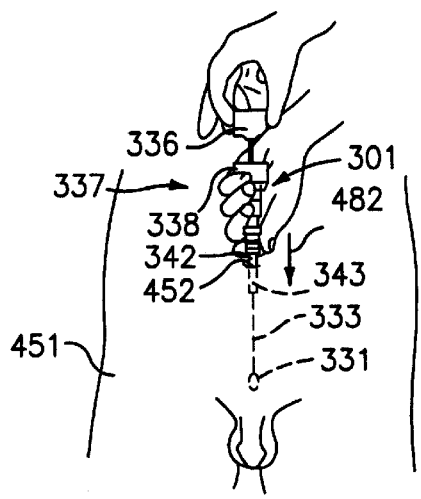

Operation and use of the surgical balloon dissection apparatus 301 in performing the method for developing an anatomic space for laparoscopic hernia repair in connection with the apparatus shown in FIGS. 39–48 may now be briefly described as follows in conjunction with the cartoons which are shown in FIGS. 49a through FIG. 49g. The surgeon in connection with the present method identifies the appropriate fascia layer to be dissected, either by direct visualization of the tissue and/or by manual palpation. Let it be assumed that it is desired to perform a hernia repair on a patient 451 and that it is desired to create an extraperitoneal working space for performing the surgical repair. The surgeon makes a small incision 452 in the skin of the patient in the umbilicus or slightly lateral of the umbilicus. A retractor (not shown) can then be utilized to open up the incision and to move it laterally to either side to locate the rectus muscles that run longitudinally of the body of the patient on both sides of the umbilicus or navel. As soon as the rectus sheath has been located, the incision is made in the rectus sheath through the incision previously made midway between the two sets of the rectus muscles. The surgeon then grasps the laparoscopic or balloon dissection apparatus 301 by using a hand, as for example his right hand as shown in FIG. 49A to grasp the handle assembly 337 to introduce the blunt end 331 into the incision to engage the anterior wall of the posterior rectus sheath. The balloon dissector 301 is then advanced longitudinally of the patient's body generally parallel to the two sets of rectus muscles as shown by the arrow 453 by using the rectus sheath as a guide to pass the blunt tip 331 to cause separation of tissue and to pass over the arcuate line and transversalis fascia to the level of the symphysis pubis. This can be readily accomplished with the balloon dissector 301 because the balloon cover assembly 316 is latched to and generally rigidly connected to the distal extremity of the introducer member 342 of the introducer device 307 by having the protrusions 413 provided on the tubular cover 381 seated within the holes 414 provided on the distal extremity of the introducer member 342. This provides a rigid assembly of the balloon dissector 301 so it can be operated by the surgeon grasping the handle assembly 337 without the need to have the physician grasp by the other hand an intermediate part of the balloon dissector to cause a desired manipulation and steering of the blunt tip 331 as the dissection of the tissue is accomplished as it is advanced.

The travel of the blunt tip 331 to the level of the symphysis pubis can be readily ascertained by the surgeon who can use his hand to palpate the abdominal region of the patient and thereby feel the blunt tip 331 as it is advanced until the blunt tip 331 strikes the symphysis pubis. This can be readily ascertained by the right hand holding the handle assembly 337 feeling the impact of the tip 331 striking the symphysis pubis 468 (see FIG. 50) which impact is communicated through the rigid structure of the balloon dissector to the handle assembly 337 where it can be felt by the hand of the surgeon. The balloon dissector 301 is then advanced a small additional amount so that the blunt tip 331 drops below the symphysis pubis 468.

Figure 50:
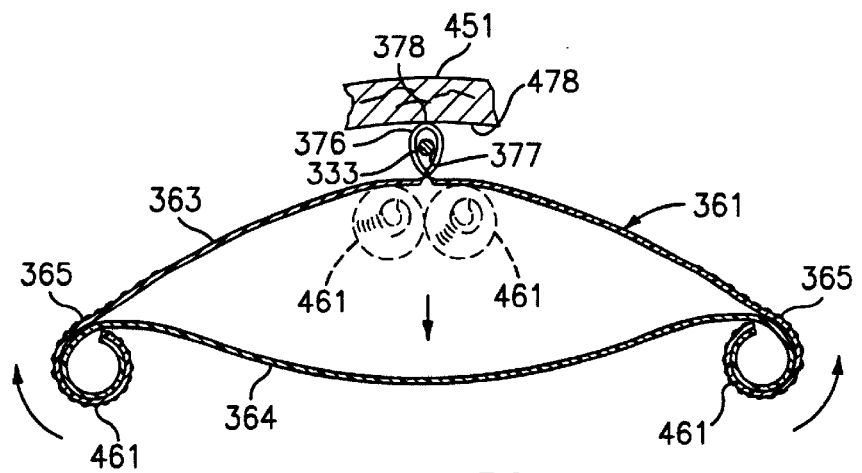
FIG. 50 is a cross-sectional view taken along the line 50—50 of FIG. 49C.

Thereafter, the balloon cover handle 391 is engaged by the same right hand of the physician as shown in FIG. 49B and the thumb is used to engage the transverse rounded protrusions 428 by moving the upper extremity of the clamping or latching member 416 proximally to cause the latch portion 426 to move into engagement with the notch 402 carried by the fin 397. As this is occurring, the legs 418 and 419 carried by the central body 417 are moved from the position shown in FIG. 42 to the position shown in FIG. 47 and in doing so engaging the camming surfaces 412 whereby the portions of the wings 396 secured to the body 393 are cammed outwardly so that the protrusions 413 are moved out of engagement with the holes 414. The direction of movement of the latch or clamping member 416 is indicated by the arrow 454 in FIG. 49B. As soon as the handle 391 has been released, the handle 391 is moved proximally with two fingers of the hand grasping the wings 396 to pull them upwardly and proximally to cause the balloon cover assembly 316 to be removed. The balloon 361 is held in place by the tunneling shaft or rod 336 and exits through the slit 386 provided at the bottom of the tubular cover 381 which serves as a tear away sheath. The balloon inflation tube 366 is retained in one of the slots 360 in the shoulders 359 so that it does not become entangled in the wings 396 as the balloon cover assembly 316 is removed. This exposes the balloon 361 which has its side margins rolled inwardly in rolls 461 with one being rolled in a counterclockwise direction and the other being rolled in a clockwise direction so that they underlie the tunneling rod 333 as shown in FIG. 50. Also to provide optimum dissection as hereinafter described before the rolling up occurs the forwardly extending protuberance 362 can be folded inwardly along a fold line 471 and the sidewardly extending lobe portions also can be folded inwardly along fold lines 472. To inflate the balloon the pinch off clamp 372 is closed and a conventional 60 cc syringe 476 containing a saline solution is connected to the one-way valve 368. The syringe 466 is then operated as shown by the arrow 477 to introduce the saline solution from the syringe 476 into the tubular member 366 and into the interior of the balloon 361 to gradually inflate the same. The one-way check valve 368 ensures that saline solution cannot exit therefrom when the syringe 466 is removed. The syringe 476 after it has been emptied can be removed and refilled with a saline solution which is introduced into the balloon in the same manner to cause the side margins of the balloon 461 to unwrap in opposite directions as shown in FIG. 50 on opposite sides of the tunneling rod 333 until they become completely unwrapped. Typically, it may take as many as approximately ten syringes of saline solution to cause the balloon 361 to completely unwrap and the move into an inflated condition as shown in FIG. 50. As the balloon is being filled and unwrapping, it continues to separate or dissect tissue overlying the peritoneum to provide an extraperitoneal working space between the transversalis fascia and the rectus muscles.

As hereinbefore described, the balloon 361 in plan has an asymmetric manta ray-like configuration to provide the desired optimum extraperitoneal working space for the hernia repair. The forwardly extending protrusion 362 provided on the balloon 361 as it is inflated dissects distally from the distal extremity of the blunt tip 331 of the guide rod 333 serves to provide good dissection of tissue in the area of Cooper's ligaments and also to dissect laterally around the inguinal rings. By utilizing an asymmetric manta ray-like construction, it is possible to provide a balloon 361 with its wide side margins or lobe portions 361a and 361b which when inflated to cause forward movement of the balloon 361 to dissect downwardly around the inguinal rings and to wedge the balloon 361 in place. The forwardly extending protrusion 362 as it is inflated dissects like a small balloon down to the Cooper's ligament. In this way, it is possible to obtain an extraperitoneal working space 478 which exposes all the desired anatomy at one time before moving off to the hernia sac and to do the final dissection for the hernia repair. By providing such a large extraperitoneal working space it is unnecessary to manually advance the dissection. The balloon has also been shaped to properly match the anatomy in which the procedure is to be formed so as to reduce to a minimum the amount of manual dissection which may be needed. Since the balloon has a particular shape and is formed of a non-elastomeric material, the dissection will occur in the desired locations which would not necessarily be the case if the balloon were formed of an elastomeric material which generally would have a tendency to follow the path of least resistance. Additional assurance is provided for ensuring that dissection will occur in the desired locations with the non-elastomeric balloon of the present invention because the balloon is held in place by the tunneling rod 333 underlying the symphysis pubis 468 as shown in FIG. 50. Also by providing roughened areas 365 these areas frictionally engage overlying tissue so that the lobe portions 361a and 361b can serve as anchors to prevent displacement of the balloon 361 after the balloon 361 as it is being inflated.

After the amount of desired tissue dissection has taken place by inflation of the balloon 361 to provide the extraperitoneal working space, the balloon 361 is deflated by connecting the evacuation fitting 371 into an evacuation port (not shown) of an operating room suction system. The pinch clamp 372 is released to open the tube 369 to permit the saline solution which had been introduced into the balloons 361 to be sucked out to completely deflate the balloon from the inflated condition as shown in FIG. 49C.

After the balloon has been deflated, the tubular member 366 can be grasped by the fingers of the hand as shown and the deflated balloon 361 pulled out through the incision 452 in the direction as shown by the arrow 481 in FIG. 49D. If necessary, the handle assembly 337 can be held by the other hand. The balloon 361 as it is being pulled off has its sleeve 376 separates from the tunneling or guide rod 331 by breaking through the linear perforations lying along the line 378. The guide rod 331 remains in place to preserve an easy entry into the extraperitoneal space which has been created. The balloon 361 can then be discarded.

After the balloon 361 has been removed, the left hand is used to grasp the lower second handle part 38 with the left hand while the right hand engages the upper or first handle part 336 of the handle assembly 337. The fingers of the right hand then engage the latch members 339 on opposite sides by the fingers of the hand to release the first part 336 from the second part 338 and to permit the left hand to move the second part 338 in the direction of the arrow 482 shown in FIG. 49E. The second part 338 carries with it the cannula 302 attached thereto and the introducer device 307 which extends therethrough with the skin seal assembly 311 mounted on the cannula tube 321. This advancement over the guide rod 333 is continued until the distal extremity 343 of the introducer member 342 has been advanced into the desired position. As soon as this has been accomplished, the skin seal assembly 311 is slidably advanced on the cannula tube 321 until the skin seal approaches the incision 452. The screw body 351 is then rotated by the fingers of the hand engaging the flange 352 and/or to the shoulder 359 to screw it into the incision 452 and to form a gas tight skin seal with the skin of the patient. As soon as a good skin seal has been established, the introducer device 307 is clamped in a fixed position with respect to the skin seal assembly 311 by pushing generally downwardly on the collar 356 to engage the collet 357 to form a friction grip between the elastomeric insert 353 and the cannula tube 321.

Figure 49F:
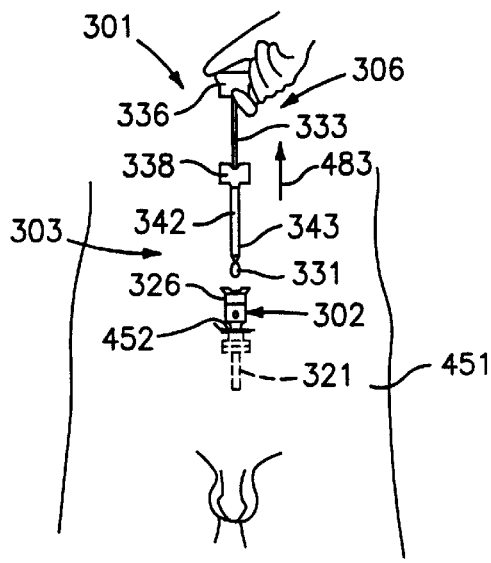
Figure 49G:
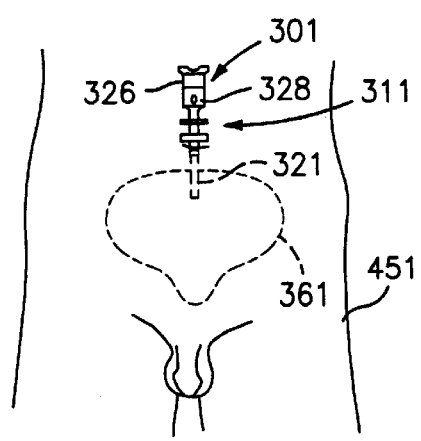

After the cannula 302 is in a fixed in position, the blunt obturator 306 can be removed along with the tunneling device or blunt obturator device 303. This is accomplished merely by continuing to pull upwardly on the handle part 336 with the hand in the direction indicated by the arrow 483 as shown in FIG. 49F. As this pulling motion continues, the blunt tip 331 will engage the distal extremity 343 of the introducer member 342 causing a withdrawal force to be applied to the second handle part 338 to cause it to automatically release from the housing 326. This permits the blunt obturator device 303 to be removed through the cannula tube 321. This is possible because the blunt tip 331 has a diameter which can pass through the interior of the cannula tube 321 and through the valving provided in the housing 326. In withdrawing the guide rod 333 carrying the obturator tip 331, it can be seen that it continues to be guided by the introducer member 342 and thus will remain centered with respect to the cannula tube 321 to avoid any pinching action at the distal end 323 of the cannula tube 321. As soon as the obturator tip 331 strikes the introducer member 342, the handle part 338 is automatically disengaged from the cannula handle 326. The latch parts 349 are substantially buried within the second handle part 338 so they are relatively inaccessible to the surgeon ensuring that he will operate the latch parts 339 carried by the first handle 336 which helps to ensure that the surgeon remove the handle parts 336 and 338 in two stages.

After this has been accomplished a source of gas such as carbon dioxide is connected to the stop cock valve 328. The stop cock valve 328 is opened to permit the carbon dioxide to inflate the dissected extraperitoneal working space such as indicated by the dotted lines 476 shown in FIG. 49G. The cannula 302 can then be utilized for introducing instruments of various types into the dissected extraperitoneal working space. The inflation gas cannot escape because of the valving provided in the handle 326 of the cannula 302.

Additional cannulae can be introduced in various positions in the abdomen of the patient through which additional surgical instruments can be introduced for performing the surgical procedure to be performed in the extraperitoneal working space. The remainder of the hernia repair procedure to be accomplished in the extraperitoneal working space is substantially the same as hereinbefore described and therefore will not be described in detail. By way of example, let it be assumed that a hernia sac has been formed in the patient, as for example by passing down into the scrotum to form a typical indirect hernia. The hernia sac can be pulled out and ligated in a manner hereinbefore described. Thereafter, a piece of mesh as hereinbefore described can be introduced through another site and rolled out over the region through which the sac had previously passed. The mesh can then be stapled in place, as for example along the Cooper's ligament. After the hernia repair has been completed, the extraperitoneal working space can be deflated by opening the stop cock valve 328 and bleeding the $CO_2$ contained therein to atmosphere to permit the abdominal wall to return to its normal position to help retain the mesh which has been placed in the desired position.

In connection with the formation of the extraperitoneal working space with the apparatus of the present invention, it has been found that it is desirable to have the guide rod 333 be in position in which it overlies the balloon 361 because this helps to ensure that the balloon dissection will occur in appropriate areas because the blunt tip 331 underlying the symphysis pubis is retained in the desired position even during the time that the balloon is unrolling during inflation. Positioning the guide rod 333 in this manner, ensures that the balloon 361 will roll out in the opposite directions from the rod and also to help to push the balloon downwardly during inflation.

In order to make the apparatus more user friendly, the parts which are to be moved for operation with respect to other parts have been color coded, as for example they can be colored black with the remaining parts being of another color, such as grey or white. Thus, the clamping or latch member 416 is of a black color because it must be removed to unlatch the balloon cover assembly 316. Similarly, the collar 356 of the skin seal assembly 311 is of a black color because it must be moved to clamp the cannula 302 in a desired position. Similarly, the latch parts 339 and 349 are of black color because they also must be moved to separate the handle parts.

The wings 396 are provided on the balloon cover 316 in addition to serving as means to facilitate grasping of the balloon cover assembly 316 when it is desired to remove the same, as serve to visually indicate the plane in which the balloon 361 of the balloon dissection apparatus 301 causes dissection. Generally this dissection plane is in a plane which is parallel to the plane in which the wings 396 lie.

As hereinbefore explained, the introducer member 342 is provided with an obturator end surface or tip which is inclined at an angle in a direction away from the normal direction of insertion to inhibit any tendency that the tip might hang up on tissue as it is being advanced through the tissue during dissection.

The sizing of the blunt obturator tip 331 so it is smaller than the inner diameter of the cannula tube 321 helps to ensure that tissue will not become entrapped or pinched between the tip 331 and the cannula tube 321. In addition, as hereinbefore described, the obturator tip 331 is tapered in both directions into a smaller dimension from the center to also minimize the possibility of any tissue being entrapped between the tip 331 and the cannula tube 321 and thereby ensuring that a shearing action will not occur.

In conjunction with the foregoing disclosure, it has been assumed that the balloon dissection apparatus hereinbefore described typically would be disposed of after each use. In the event it is desired to economize and it is desired to reutilize at least certain portions of the balloon dissection apparatus after a use in a laparoscopic procedure, another embodiment of a balloon dilatation apparatus 501 incorporating the present invention is shown in FIGS. 51–55. As shown therein it consists of a handle assembly 502 similar to the handle assembly 337 hereinbefore described which includes a handle part 503 similar to the handle part 336. Other parts of the balloon dissection apparatus 501 are not shown because they can be identical to those hereinbefore described. The handle part 503 is provided with two sections 506 and 507 which can be fastened together in a suitable manner such as by ultrasonic bonding or an adhesive. Latch members 511 and 512 are provided on opposite sides of the handle part 503 and are provided with finger portions 513 that are adapted to be engaged by fingers of the hand which extend outwardly through recesses 514 in the sections 506 and 507. The latch members 511 and 512 are each provided with a latch 516 which is yieldably urged in an outward direction by a yieldable spring member 517 engaging a downwardly depending lip 518 provided within the sections 506 and 507. The latch members 511 and 512 are pivotally mounted between the sections 506 and 507 by pivot pins 519 formed integrally on the latch members 511 and 512 and extending into bosses 521 provided in the sections 506 and 107 which are formed of a suitable material such as plastic.

First and second inserts 526 and 527 formed of a suitable material such as plastic are mounted in the sections 506 and 507. First and second latch members 531 and 532 formed of a suitable material such as metal are provided which are seated in recesses 533 and 534 provided in the insets 526 and 527. The latch members 531 and 532 are generally U-shaped and are yieldably urged into engagement with each other to form an elongate slot 536 extending therethrough. Upstanding legs 538 formed integral with the inserts 526 and 527 are provided in rectangular spaces 539 in the inserts 526 and 527 so that the upper extremities of the legs 538 can be flexed by movement of the latch members 531 and 532 as shown by dotted lines in FIG. 54.

A guide rod 541 is provided which is similar to the guide rod 333 with the exception that its distal extremity 542 is also provided with an annular recess 533. The distal extremity 542 is provided with a chamfer 544 and a pair of opposed flats 546 which extend through the chamfer 544. The guide rod 541 extends through a hole 551 provided by semicircular recesses formed in the sections 506 and 507 and by a hole 552 formed by semicircular recesses in the inserts 526 and 527. A larger hole 553 formed by semicircular recesses in the inserts 526 and 527 of a larger diameter than the hole 552 is provided which receives a push-button 556 and extends through a hole 557 also formed by semicircular recesses provided in the sections 506 and 507. A dish-shaped or concave recess 558 is provided in the sections 506 and 507 and facilitates engaging the push-button 556 by a finger of the hand.

Figure 51:
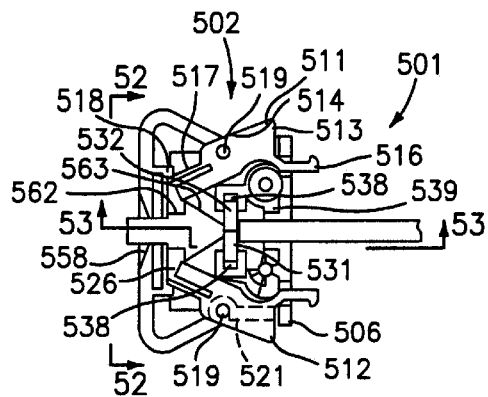
FIG. 51 is a cross-sectional view taken along the line 51—51 of FIG. 52 showing another embodiment of a balloon dissection apparatus incorporating the present invention.
Figure 52:
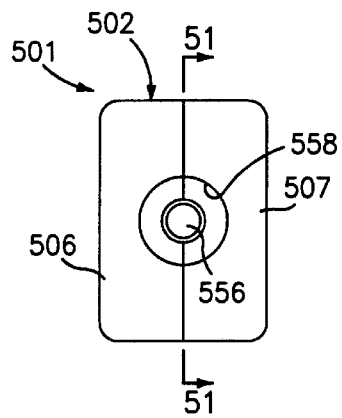
FIG. 52 is an end elevational view taken along the line 52—52 of FIG. 51.
Figure 53:
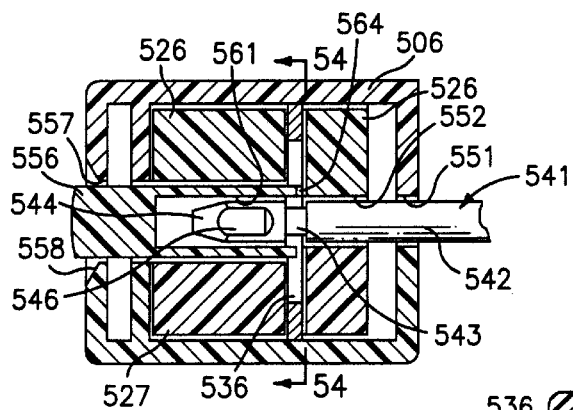
FIG. 53 is an enlarged cross-sectional view taken along the line 53—53 of FIG. 51.
Figure 54:
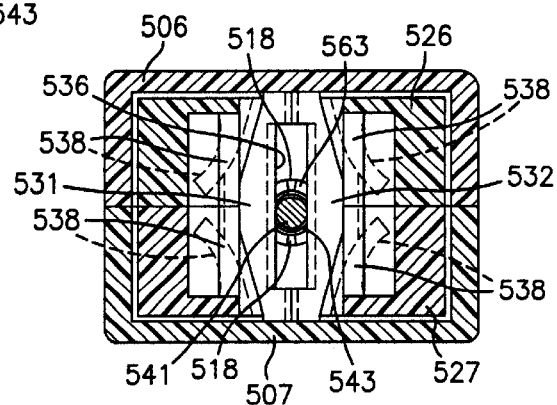
FIG. 54 is an enlarged cross-sectional view taken along the line 54—54 of FIG. 53.
Figure 55:
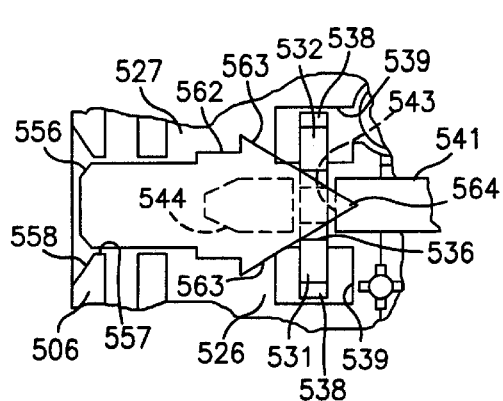
FIG. 55 is an enlarged cross-sectional view of a portion of the view shown in FIG. 51 showing the latch members moved to permit removal of the guide rod.

The pushbutton 556 is provided with a bore 561 which is sized so that it can receive the distal extremity 542 of the guide rod 541. The pushbutton is provided with sideways extending skirts 562 extending 180° with respect to each other and which are provided with distally and inwardly extending camming surfaces 563 which terminate at a tip 564 that is generally V-shaped as shown in FIG. 51. The tip 564 is formed so that it is adapted to enter into the slot 536 formed by the U-shaped members 531 and 532. Thus, when the pushbutton 556 is depressed, the tip 564 will enter the slot 536 in a progressive manner to urge them apart so that the camming surfaces 563 carried thereby engage the U-shaped latch members 531 and 532 in regions just above and below the guide rod 541 so that the guide rod 541 is released by the U-shaped latch members 531 and 532 permitting it to be pulled out of the handle part 503. Release of the guide rod 541 makes it possible to separate the guide rod 541 from the remainder of the balloon dissection apparatus 501 so that the handle assembly 502 and the other parts carried thereby can be separated from the guide rod. Thereafter, the guide rod 541, the balloon 361 and the balloon cover assembly 316 can be disposed of. The other parts of the apparatus can be reutilized after appropriate sterilization. In order to ensure that the other parts survive sterilization, it may be desirable to form the plastic reusable parts of a suitable plastic such as a polysulfone.

Still another embodiment of the laparoscopic apparatus incorporating the present invention is shown in FIGS. 56–62. The laparoscopic apparatus 600 consists of an introducer device 601. The introducer device consists of a elongate tubular member or cannula 602 formed of a suitable transparent medical grade plastic which is provided with proximal and distal extremities 603 and 604 with a bore 606 extending from the proximal extremity 603 to the distal extremity 604. A valve housing 611 is mounted on the proximal extremity 603 of the tubular member 602 and is provided with a valve 612, which may be of the type disclosed in copending application Ser. No. 08/124,283 filed Sep. 20, 1993, for example. The valve housing 611 and the valve 612 provided therein can accommodate relatively large diameter devices which are adapted to be introduced through the bore 606 of the tubular member 602 and form a seal with respect thereto.

An inflatable balloon 616 is provided which is formed of a sheet 617 (see FIG. 69) of a non-elastomeric plastic material of a medical grade such as PET-E. The sheet 617 is provided with a weakened region 618 extending transversely of the sheet, as for example by providing spaced-apart perforations in the sheet 617 (see FIG. 60). The sheet 617 as shown in FIG. 60 is folded over onto itself to provide two portions 617a and 617b with a fold line 619 being formed parallel to but spaced from the perforations 618 by a suitable distance, as for example one-quarter of an inch. A linear heat seal 621 extends across the sheet 617 and bonds the two portions 617a and 617b to each other along a line parallel to but spaced apart from the fold line 619 and also from the perforations 618 by a suitable distance, as for example three-quarters of an inch. This three-quarter inch dimension is dependent upon the size of the balloon to be formed as hereinafter described. The sheet 617 is cut adjacent its outer margins along the dotted line 622 to provide the balloon with the desired conformation as for example the manta ray type shape hereinbefore described having a rounded distal extremity.

After the heat seal 621 has been formed, the sheet 617 can be slit along the fold line 619 by suitable means such as a knife to provide two additional portions 617c and 617d formed from the sheet 617. Thus, by use of the heat seal 621 there are provided two portions 617a and 617b which can be in a plane and two additional portions 617c and 617d that extend transversely and outwardly of the plane formed by portions 617a and 617b (see FIG. 62). Also, these portions 617a–617d can be described as forming an X with the portions 617a and 617b forming the top side of the inflatable balloon assembly 616.

Thereafter, the portions 617a and 617b are unfolded so that they lie in a plane. They are then placed over another precut sheet 623 (see FIG. 62) of the same non-elastomeric material as the sheet 617 and a suitable seal, as for example a heat seal 624 formed around the entire outer perimeters of the sheet 623 to bond it to the outer perimeter of the portions 617a and 617b to form a fluid-tight enclosure to provide a space 626 within the balloon 627. In order to make it possible to inflate the balloon 627 with an inflation medium, as for example with a saline solution, one end of a central portion of the balloon 627 adjacent the portions 617c and 617d is mounted in an annular recess 628 provided on the distal extremity 604 of the tubular member 602 (see FIG. 56) is bonded thereto in such a manner such as by an adhesive tape 629 to form a fluid-tight connection between the distal extremity 604 of the tubular member 602 and the space 626 within the balloon 627. Alternatively, a tube clamp of the type hereinafter described can be used. The balloon 627 is provided with a rounded protuberance 631 to provide the desired configuration for the dissected anatomic space to be created by the balloon 627 and also to aid in the positioning of the balloon 627 during placement of the balloon in tissue in the body.

After the heat seal 624 has been completed, the outer side margins 632 and 633 of the balloon 627 are rolled inwardly and downwardly in opposite directions towards the heat seal 621 to form two rolls 636 and 637 which are immediately adjacent to each other and generally underlie the heat seal 621. The two flaps or portions 617c and 617d are then brought downwardly as shown in FIG. 63 so that they enclose the rolls 636 and 637 and are bonded together in a suitable manner such as by a heat seal 641 extending transversely of the portions 617c and 617d to form an enclosure or cover 642 for the compact rolls 636 and 637. The perforations 618 are within the confines of the cover or enclosure 642 formed for the rolls 636 and 637 within the heat seal 641 so that the cover or enclosure 642 for the rolls can be made operable or in other words slit along the weakened region along the perforations 618 to release the rolls 636 and 637 as hereinafter described. From the construction hereinbefore described it can be seen that the balloon 627 forms a part of the inflatable balloon assembly 616 and is mounted on the distal extremity of the tubular member 602.

Means is provided for inflating the balloon 627 and consists of a Luer-type fitting 646 which is provided on the housing 611 and opens into the interior of the housing 611 below the valve 612 in the housing 611 so that it is in communication with the bore 606 and with the interior space 626 within the balloon 627. The fitting 646 is connected by flexible tubing 648 to a male fitting 649 which can be connected to a suitable fluid source, as for example a syringe (not shown) containing a saline solution to be utilized for filling the balloon. A tubing clamp 652 of a conventional type is provided on the tubing 648.

A pair of diametrically extending wings 656 and 657 (see FIG. 58) are formed integral with the housing 611 and lie in a plane which is parallel to the planes in which the two halves of the balloon 627 lie. As hereinafter described, these wings 656 and 658 serve as means for ascertaining the orientation of the balloon 627 during dissection as hereinafter described. The wings 656 and 657 are sized so that they are adapted to be engaged by the fingers of the human hand.

Means is provided for introducing an insufflation gas into the anatomic space as it is being dissected and during the time the laparoscopic apparatus 600 is being utilized. This means consists of a tubular member 661 which is provided with a lumen 662 (see FIG. 63) extending between the proximal and distal extremities 663 and 664 of the tubular member 661. The tubular member 661 can be secured to the balloon 627 by suitable means such as an adhesive and has its distal extremity 664 extending into the region of the rounded protuberance 631. The proximal extremity 661 is secured to a Luer-type fitting 666 and is adapted to be connected to a source of insufflation gas.

A skin seal 671 having a helical thread 672 formed thereon has a cone shaped configuration in which the cone increases in diameter from the distal extremity towards the proximal extremity. The skin seal 671 is of the type disclosed in copending application Ser. No. 08/124,333 filed Sep. 20, 1993 and has a slip-friction fit on the exterior surface of the tubular member 602. The skin seal 671 has an axially adjustable collar 674 which can be moved into clamping engagement with the tubular member 602. The skin seal 671 is provided with a large bore 673 so that it can accommodate various sized cannulae ranging in size from 10–15 millimeters in diameter. The skin seal 671 is also provided with a conventional retaining mechanism for retaining a cannula inserted therethrough at the desired depth.

The skin seal 671 has a longer length than is typical because in addition to serving as a skin seal, it is utilized to preserve access to the dissected space. In other words, it serves as a guide for directing other cannulae into the dissected space.

The laparoscopic apparatus 600 also includes a tunneling shaft assembly 676 (see FIG. 57) which consists of a tubular member 677 having a bore 678 extending therethrough. The tubular member 677 is formed of a transparent medical grade plastic and is provided with an outer diameter which is adapted to fit within the skin seal 671. It can have a suitable length such as 15–30 centimeters.

The tunneling shaft assembly 676 also consists of a closed blunt rounded tip 681 formed integral with the tubular member 677. The tip 681 is also formed of the same transparent medical grade plastic as the tubular member 677. The tip 681 is provided with a conical recess 682 of a depth so that the wall thickness is the same as that of the tubular member 677. It should be appreciated that if desired, the tip 681 can be formed as a separate part from the tubular member 677 and secured thereto by suitable means such as an adhesive. The conical recess 682 is sized so that it can receive the distal extremity of a laparoscope as hereinafter described.

Operation of the laparoscopic apparatus 600 shown in FIGS. 56–63 may now be briefly described as follows. Let it be assumed that the laparoscopic apparatus 600 is ready to be utilized by a physician in a laparoscopic procedure to perform a hernia repair. Typically, the introducer device 602 with the balloon assembly 616 would be shipped by the manufacturer along with the skin seal 671 and the tunneling shaft assembly 676. The tunneling shaft assembly 676 has a bore 678 that can readily accommodate a conventional 10 millimeter laparoscope 686. The conventional laparoscope 686 is provided with a shaft 687, an eyepiece 688 and a fitting 689 for introducing light. Such a laparoscope 686 is inserted into the bore 678 down into the tip 682 in the tip 681 of the tunneling shaft assembly 676. A baffle 683 (see FIG. 57A) is mounted in the bore 682 of the tip 681 and extends laterally and axially thereof. The baffle 683 is formed of a suitable material such as plastic and is secured to the tunneling shaft assembly 676 in a suitable manner such as by an adhesive (not shown). The baffle 683 is preferably formed of a suitable opaque material such as a black plastic. Alternatively, it can be provided with a reflective surface away from the lens of the laparoscope. Thus the baffle serves to keep reflective light away from the lens of the laparoscope to improve the viewing capabilities of the laparoscope without interference from unwanted reflections, as represented by the ray 689, to provide a glare-free view by the laparoscope. The baffle 683 is provided where the viewing lens for the laparoscope 687 is disposed in one semicircular quadrant. Where the viewing lens for the laparoscope is in the center, a cylindrical proximally extending opaque baffle 691 (see FIG. 57B) is mounted in the tip 681 and circumscribes the lens to screen out unwanted reflections in the field of view for the laparoscope to provide a glare-free view by the laparoscope.

The tunneling shaft assembly 676 is then taken and its tip 681 introduced through the valve housing 611 and into the bore 606 of the introducer device 602 and thence into the balloon assembly 616 mounted thereon until the tip 681 is in disposed in the rounded protuberance 631 of the balloon 627 with the tunneling shaft assembly 676 disposed in the balloon 637. The tubular member 677 of the tunneling shaft assembly 676 provides the desired rigidity for the balloon 637 so that it can be introduced into an incision made in the appropriate location, as for example in the umbilicus as described in conjunction with the previous embodiments.

The tunneling shaft assembly 676 with the balloon carried thereby is then advanced into the tissue in the manner hereinbefore described in connection with previous embodiments with the progress being observed through the laparoscope 686. The laparoscope 686 makes it possible to view the progress of the tip 681 and the various tissues being encountered, since the tip 681 and the balloon 627 are transparent.

Immediately prior to inflation of the balloon 627, the wings 656 and 657 are oriented so they lie in a plane which corresponds to the plane in which it is desired to have the balloon 627 carry out the dissection. Thus it can be seen that the wings 656 and 657 help to ensure that the dissection occurs in the appropriate plane.

As soon as the tip 681 of the tunneling shaft assembly 676 is located in the desired position, a saline solution can be introduced through the fitting 649 and into the bore 606 directly into the space 626 in the balloon 627 to cause inflation of the balloon. As the balloon 627 begins to inflate, the balloon 627 breaks the cover 642 by causing separation along the perforations 618. This permits the rolls 636 and 637 of the balloon 627 to evert outwardly and gradually unroll and progressively inflate in two opposite lateral directions in the same plane to cause dissection of the tissue in a natural plane as hereinbefore described in connection with the previous embodiments. During the time this dissection is taking place, the dissection can be viewed through the laparoscope 686 to visualize anatomic landmarks. The visualization through the laparoscope 686 is quite effective because the index or refraction of the saline solution is near to that of the balloon material so there is very little reflection compared to a situation in which a visualization is attempted to be accomplished when the dissection balloon is filled with air.

Also during the time the balloon is inflated, it is possible to insert the additional accessory trocars to be utilized during the laparoscopic procedure into the dissected space to visualize their entrance into the dissected space and to aid in proper positioning of the trocars.

After inflation of the balloon 327 and the desired dissection has been accomplished, the skin seal 671 can be slid down on the tubular member 602 into the incision and screwed into the incision to form a substantially gas-tight seal therewith.

In connection with the present apparatus during the time that dissection is being accomplished, it is possible to pass an insufflation gas into the space as it is being dissected. This can be accomplished by introducing a suitable gas, as for example $CO_2$ through the tubular member 661 through the fitting 666. This will provide some inflated dissected space outside the balloon in the vicinity of the tip 681 to aid in visualization of the anatomic space being created.

Let it now be assumed that the desired dissection has been accomplished and it is desired to remove the balloon assembly 616. The skin seal 671 can be inserted before or after inflation of the balloon 627. The skin seal 671 can be inserted by exerting a sliding and rotating motion to the skin seal 671 on the tubular member 602 to cause the distal extremity of the skin seal 671 to progressively enter the incision until a substantially fluid-tight seal is formed between the skin of the patient at the incision and the skin seal 671. Thereafter the introducer 601 can be grasped by holding the skin seal 671 stationary in one hand and the housing 611 of the introducer 601 with the other hand and pulling the introducer 602 outwardly from the skin seal and pulling with it the laparoscope 686 if it has not been previously removed, the tunneling shaft assembly 676 followed by the balloon assembly 616 secured to the end of the introducer device 601.

Thus, it can be seen that the introducer device 601 and the balloon assembly 616 can be removed through the enlarged bore 673 provided in the skin seal 671. As soon as this has been accomplished, a conventional trocar cannula can be introduced into the skin seal and clamped into the skin seal at the desired depth by operation of the collar 674 in the manner described in copending application Ser. No. 08/124, 333 filed Sep. 20, 1993. Thereafter, insufflation of the anatomic space can be accomplished by introducing a gas through the trocar and thereafter the laparoscopic procedure can be completed in the manner hereinbefore described in connection with the previous embodiments.

In connection with the foregoing, it can be seen that by making minor changes in the construction it is possible to save a great number of parts of the balloon dissection apparatus for reuse after sterilization. Only the parts which are most difficult to clean are disposed of after a one-time use.

From the foregoing it can be seen that there has been provided an apparatus and method which is particularly suitable for developing an anatomic space such as an extraperitoneal working space between the abdominal wall and the peritoneum by dissecting tissue with the use of a non-elastomeric balloon. The balloon dissection apparatus has many features facilitating its use in developing such an anatomic space and for particularly developing an extraperitoneal working space for hernia repair.

In connection with the present embodiment of the invention it can be seen that visualization is possible through a laparoscope during the entire dissection procedure. The laparoscopic procedure has also been simplified that it is unnecessary to remove a balloon cover as in the previous embodiments. In the present embodiment of the invention, the balloon can be introduced without a balloon cover and can be inflated almost immediately. It also can be readily removed after the desired dissection has been completed by pulling the balloon out through the skin seal and thereafter inserting the trocar cannula. The present invention makes it possible to preserve access to the dissected space without the need of retaining a obturator in location as with the previous embodiments.

In FIG. 64, there is shown a cross-sectional view of the balloon 627 laterally disposed inwardly extending folded portions 627a and 627b. Thus, in effect the balloon 627 is double-folded inwardly in a lateral direction before it is wrapped up and both sides formed into rolls and in the manner hereinbefore described and as shown particularly in FIG. 63. In addition, the rounded protuberance 631 can also be folded inwardly in a similar manner before the balloon is rolled-up and sealed between the portion 617c and 617d by the heat seal 641. This balloon 627 is folded in the manner shown in FIG. 64 and then wrapped as shown in FIG. 63 and can be utilized in the same manner as the embodiment hereinbefore described. Upon inflation of the space 26 within the balloon, the balloon begins to inflate in an up and down direction rather than laterally until sufficient pressure is created within the balloon to cause the inverted bifolds 627a and 627b to begin to evert outwardly to aid in forcing the balloon to unroll. This everting action of the balloon facilitates unrolling of the balloon and aids in dissection of tissue. This everting motion also avoids dragging the balloon across the tissue as it fills. When folded in the manner shown in FIG. 64, the balloon unfurls from within and progressively lays itself out on the dissected tissue as it inflates. Similarly, the rounded protuberance 631 will evert and also unfold in a similar manner to create dissection in a forward direction.

It should be appreciated that with the lateral bifolds provided in the balloon 627 the tubular member 677 can be inside or outside the balloon and still be provided with the broad bi-folds in the balloon 627.

In connection with the present invention it has been found that in certain surgical procedures there is a need to dissect around an obstruction as for example a hernia. For this purpose, a horseshoe-shaped or bifurcated balloon 701 is provided as shown in FIGS. 65–68. The balloon 701 is substantially Y-shaped as shown in FIG. 68 and is provided with a bifurcation 702 which leads into two legs 703 and 704 to provide a U-shaped space 706 therebetween. The balloon 701 can be constructed in the manner hereinbefore described for the previous balloons used in accordance with the present invention.

The legs 703 and 704 can be inverted into the bifurcation 702 as shown in FIG. 66 and then can be rolled into two rolls rolled in from opposite sides onto an olive-tipped guide rod 711 shown in FIG. 65 and held in place by a separate balloon cover (not shown) or by the use of flaps forming a sleeve such as shown in FIG. 59 to provide an assembly 712. It has been found that in connection with the present invention to achieve the best dissection capabilities for the balloon and expansion of the balloon, the balloon 701 is secured to the guide rod or tunneling rod 711 so that the guide rod underlies the balloons. The side margins are rolled inwardly into two rolls so that the two rolls face downwardly toward the tunneling guide rod 711. They are then brought into close proximity with each other to form a single roll and secured to the tunneling guide rod 711 as hereinbefore described. A tubular member 713 providing a balloon inflation lumen opening into the interior of the balloon 701 is sealed into the balloon 701. A Y adapter 714 is secured to the tubular member 713 and carries a male fitting 716 and another tubular member 717 on which there is mounted a tubing clamp 718 and another male fitting 719.

Figure 69:
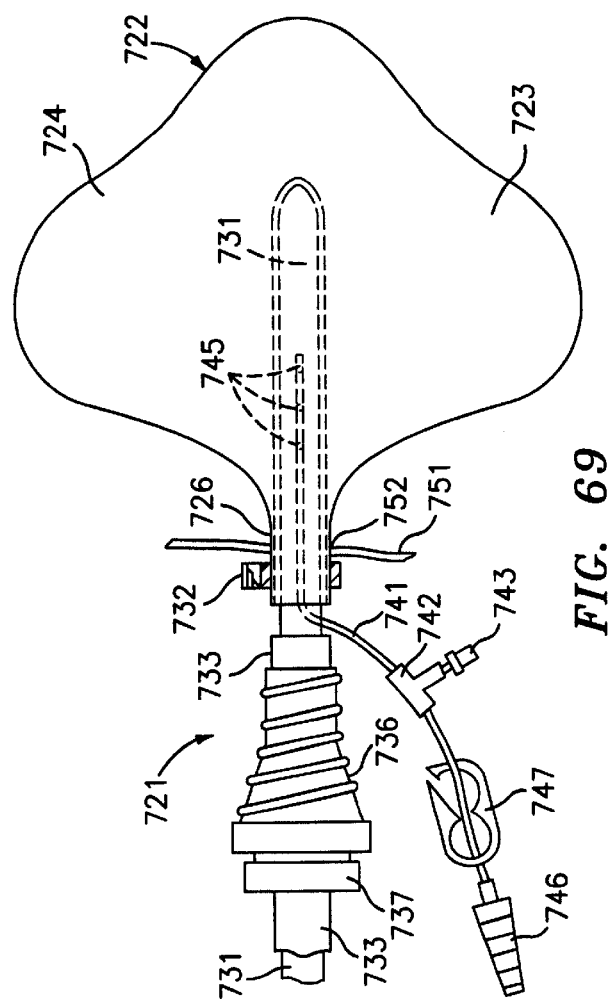
FIG. 69 is a plan view of another embodiment of a laparoscopic apparatus incorporating the present invention.

Let it be assumed that it is desired to dissect around an obstruction 720 which by way of example can be ventral hernia or other obstruction that cannot be readily dissected. Let it also be assumed that the assembly 712 shown in FIG. 65 has been introduced into dissected space in the manner hereinbefore described with or without the laparoscope and an obstruction 720 is encountered and it is desired to dissect around the obstruction 720. This can be accomplished by removing the cover or sleeve (not shown) that was used for enclosing the balloon and securing it to the guide rod 711. As soon as the balloon 701 is released, it can be inflated through the tubular member 713 to unroll sideways or laterally in a plane just proximal of the obstruction 720. The balloon 701, because of the manner in which it was rolled-up, will unroll downwardly and outwardly away from the tunneling guide rod 711 to create the desired dissection. Continued inflation of the balloon will cause one or both the legs 703 and 704 to progressively evert and advance around the obstruction 720. Thus, as shown in FIG. 67, the arm 704 everts and passes around one side of the obstruction 720 while accomplishing dissection as it goes, whereas the other arm 703 can thereafter or simultaneously evert to cause dissection around the other side of the obstruction 720 until both of the legs 703 and 704 are completely inflated to create a dissection extending around the obstruction 720. The balloon 701 can then be deflated and removed through the skin seal in the manner hereinbefore described. Insufflation and other surgical procedures in connection with the present invention can thereafter be performed.

Where it is desired to utilize a smaller cannula and skin seal, a construction and method such as that shown in FIG. 69 can be utilized. The laparoscopic apparatus 21 shown in FIG. 69 for use for such a purpose consists of a manta ray-shaped balloon 722 of the type hereinbefore described which is provided with sides or wings 723 and 724. The balloon 772 is provided with a neck 726 through which a tubular member 731 of the type hereinbefore described is serving as a scope cover. The neck of the balloon is secured to the tubular member 731 by suitable means such as a hose clamp 732 of a conventional type. The tube clamp can be formed of a suitable material such as plastic and can be of the type manufactured by Tyton Corporation, 7930 North Faulkner Road, Milwaukee, Wis. 53223. The tubular member 731 extends through a skin seal 736 of the type hereinbefore described which is provided with an axially movable ring or collar 737. In order to be able to insert the laparoscopic apparatus 721 into an incision, the wings or sides 723 and 724 can be rolled inwardly and secured to the distal extremity of the tubular member 731 by suitable means such as a balloon cover (not shown) of the type hereinbefore described or, alternatively, by providing two additional flaps on the balloon of the type hereinbefore described which can be utilized for securing the rolled balloon to the tubular member.

A tubular member 741 is sealed within the balloon 722 and carries a balloon inflation lumen (not shown) which is in communication with the interior of the balloon 722 through its open end and through a plurality of longitudinally spaced apart holes 745 in communication with the balloon inflation lumen. Tubular member 741 carries a Y fitting 742 that carries a male adapter 743. Tubing 74 is connected to the Y adapter 742 and has mounted thereon another male fitting 746 and a hose clamp 747, all of the type hereinbefore described.

Operation and use of the laparoscopic apparatus 721 as shown in FIG. 69 may now be briefly described as follows. As in the previous embodiments, the distal extremity of the apparatus 721 can be inserted through a cannula or a trocar sleeve 733. As hereinbefore explained, the distal extremity of the apparatus can be advanced by the use of the tubular member 731 as an obturator to advance the balloon to the desired space. As hereinbefore explained, this procedure can be viewed through a laparoscope (not shown) inserted into the tubular member 731 permitting viewing through the distal extremity of the transparent tubular member 731 and the transparent balloon 722. After the desired amount of dissection has been accomplished to induce the balloon 722 into the desired location, the balloon cover if utilized can be removed. Thereafter, the balloon 722 can be inflated by introducing a saline solution through the male fitting 743 and through the tubular member 741 to cause it to unroll in two opposite directions to cause additional dissection of the tissue to create an anatomic space below the skin of the patient. The balloon is retained on the tubular member or scope cover 731 by the clamp 732 during the time that inflation of the balloon is taking place.

After the desired amount of dissection has taken place by inflation of the balloon 722, the balloon 722 can be deflated by opening up the clamp 747 and permitting the fluid, as for example the saline solution, to exit through the male adapter 746. As soon as the balloon 722 has been deflated, the clamp 732 can be removed by pressing sideways on the clamp 732.

The cannula 733 can then be advanced on the scope cover 731 to push the proximal extremity 726 of the balloon 722 through the incision and so that the cannula 733 extends through the incision. The skin seal 736 is advanced on the cannula into the incision to push off of the distal extremity of the cannula 733. Then, while holding the cannula 733 and the skin seal 736 in place, the tubular member or scope cover 731 can be retracted and is completely removed from the balloon 722. As soon as the scope cover 731 has been removed, the deflated balloon 722 can be withdrawn through the incision 752 by pulling on the tubular member 741. As soon as the balloon 722 has been removed, the skin seal 736 can be rotated to complete insertion of the skin seal to form a fluid-tight seal between the skin 751 and the skin seal 736. Thereafter, the anatomic space which has been formed by dissection of tissue by the use of the balloon 722 can be insufflated in the manner hereinbefore described and the desired surgical procedures performed.

Figure 70:
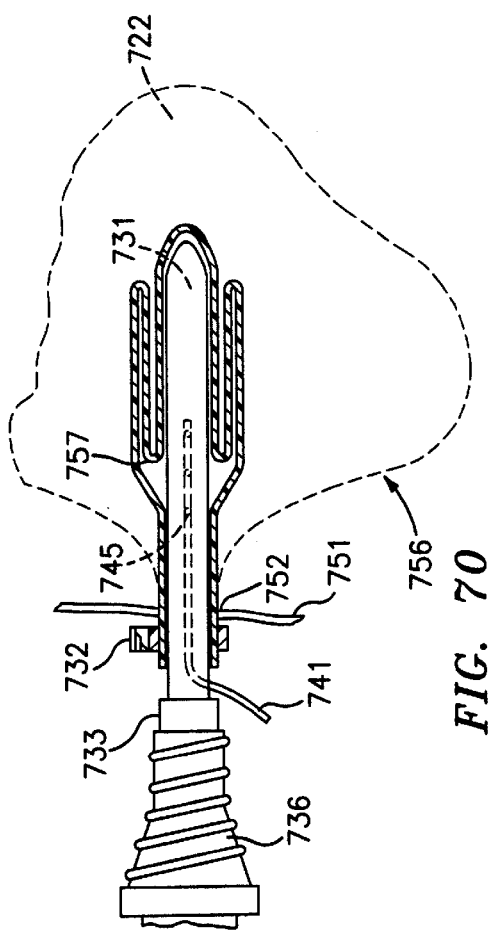
FIG. 70 is another plan view showing another embodiment of a laparoscopic apparatus incorporating the present invention.

Another embodiment of a laparoscopic apparatus 756 incorporating the present invention is shown in FIG. 70, which is substantially identical to that shown in FIG. 69 with the exception that the balloon 722 at the distal extremity of the balloon has been folded inwardly onto itself onto the distal extremity of the scope cover 731 as shown by the fold 757. Operation and use of this embodiment is substantially identical to that hereinbefore described in connection with the embodiment shown in FIG. 69. Upon introduction of an inflating fluid through the tubular member 741, the balloon will expand by everting outwardly to move the fold 757 in the balloon after which the balloon will unroll sidewise in a manner similar to the balloon 722 as hereinbefore described in FIG. 69 to assume the dotted-line shape shown in FIG. 70. Thereafter, the balloon 722 can be deflated and removed in the manner hereinbefore described in connection with FIG. 69.

A laparoscopic apparatus 761 incorporating another embodiment of the invention is shown in FIGS. 71 through 73 and as shown therein consists of a balloon 762 which as shown can have a manta ray shape of the type hereinbefore described. It is provided with a narrowed down neck 763 which is adapted to engage an annular taper 764 (see FIG. 73) carried by the distal extremity of a cannula 766. The cannula 766 can be substantially identical to the cannulae hereinbefore described with the exception that it is provided with an inwardly extending annular taper 764 which can be engaged by the neck of the balloon. The neck of the balloon is held in a fluid tight seal with respect to the taper 764 by a tubular member 771 which is provided with a bore 772 extending therethrough and which is sized so that it is adapted to receive a conventional laparoscope 773 of the type hereinbefore described. The tubular member 771 is provided with an outer tapered distal extremity 776 (see FIG. 74) which is adapted to mate with the inner annular taper 764 provided on the cannula 766 and to retain the neck 763 of the balloon in a position so as to form a fluid-tight seal to retain the balloon on the cannula 766 during and after inflation as hereinafter described. Alternatively, this tapered distal extremity can be formed in a suitable manner such as by a collar 777 (see FIG. 73) formed separately or as an integral part of the tubular member 771 and having a slightly greater outer diameter than the outer diameter of the tubular member 771 and is spaced a short distance from the distal extremity of the tubular member 771. This space has disposed therein an resilient epoxy-like material 778 having an inwardly and forwardly extending taper of decreasing diameter in a direction towards the distal extremity of the tubular member 771. This material 778 has a taper which is similar to the taper provided on the inwardly extending annular taper 764 on the cannula 776 so that when the tubular member 771 is pushed inwardly in a distal direction, the tubular member will engage the neck 763 of the balloon and frictionally hold it in place and at the same time frictionally retain the tubular member 771 therein.

In the event there is difficulty in seating the neck of the balloon within the taper 774, the distal extremity of the laparoscope 773 can be inserted through the bore 772 of the tubular member 771 and extended a slight distance into the balloon 762 beyond the neck of the balloon. The neck 763 of the balloon 762 can then be wrapped about the laparoscope and the neck of the balloon with the laparoscope can be pushed inwardly with the tubular member 771 being retracted out of the way from the taper 764. As soon as the neck 763 is seated over the inner taper 764, the tubular member 771 can be pushed distally to frictionally engage the neck of the balloon to firmly clamp it in place to form a sealing engagement between the balloon 762 and the cannula 766. Thereafter if desired, the laparoscope 773 can be retracted.

There are many portions of the apparatus 761 which are very similar to that hereinbefore described. Thus, a skin seal 784 is slidably mounted on the cannula 766 and carries an axially movable collar 782 of the type hereinbefore described for frictionally retaining the skin seal 784 in a predetermined axial position on the cannula 771. A valve housing 786 is mounted on the proximal extremity of the cannula 771 and carries an inlet port 787. A handle 788 of the type hereinbefore described is detachably mounted on the valve housing 786 and carries with it the tubular member 771. Another valve housing 791 is mounted on the handle 788 and is provided with a valve (not shown) to form a fluid tight seal with respect to the outer surface of the tubular member 771. The laparoscope 773 extends through the tubular member 771 which extends through the valve housing 771 and also through the valve housing 786.

In the laparoscopic apparatus 771, an additional port is provided in the balloon 762 for inflating the balloon and consists of a tubular member 796 which extends into the balloon and is sealed in the balloon. It is provided with an open end and a plurality of spaced-apart holes 797 which open into the bore in the tubular member 796 and can be utilized for inflating the interior of the balloon 722 in a manner hereinbefore described. A fitting assembly 799 is mounted on the tubular member 796 and consists of a wye 801 mounted on tubular member 796. The wye 801 has one leg of the Y connected to an adapter 802 and has the other leg of the Y connected to a tube 803 having a tubing clamp 804 mounted thereon and connected to another male connector 806 of the type hereinbefore described.

Operation and use of the laparoscopic apparatus shown in FIGS. 71–73 may now be briefly described as follows. Let it be assumed that the apparatus has been shipped in the manner shown in FIGS. 71–73 with the neck 763 of the balloon retained against the taper 764 by the tubular member 771. As hereinbefore described, the balloon 762 can be wrapped up into a roll and enclosed within a removable balloon cover (not shown) or alternatively it can be enclosed by an integral balloon cover of the type hereinbefore described so that the balloon roll with the balloon cover can serve as an obturator. If necessary, the balloon roll and cover combination can be aided by the distal extremity of the laparoscope 773 extending to the distal extremity of the balloon 762 to cause the balloon roll and cover to pass through the incision and do sufficient dissection of tissue so that the balloon is disposed below the skin of the patient.

The balloon cover, if one is present, can then be removed and the balloon 762 inflated by introducing a saline solution through the adapter 102 by use of a syringe or other suitable means. As soon as the balloon is inflated and has been unrolled to create the dissection as hereinbefore described, the balloon can be deflated by permitting the saline solution to pass through male adapter 806 upon opening of the tubing clamp 804. The cannula 766 can then be pushed through the incision into the anatomic working space which has been created by the balloon 762. The laparoscope 773 can then be removed. Thereafter the handle 788 can be released to bring with it the tubular member 771 with the tapered distal extremity 776 to release the neck 763 of the balloon 762. Thereafter the fitting assembly 799 can be grasped and the balloon 762 can be withdrawn through the incision outside the cannula 766. After the balloon has been retracted, the skin seal 781 can be advanced into the incision to form a fluid tight seal with respect to the skin of the patient.

From the foregoing, it can be seen that with the laparoscopic apparatus 761 shown, the laparoscope 773 can be utilized during insertion of the balloon into the incision and during the time that the balloon is being inflated to dissect tissue. However, it should be appreciated that if it is unnecessary to view this procedure, the laparoscope 773 can be eliminated, because in most instances the wrapped up balloon has sufficient rigidity to serve as an obturator to permit the balloon to be pushed through the incision and to create adequate dissection below the skin of the patient to permit entry of the balloon after which the balloon can be inflated as hereinbefore described.

The laparoscopic apparatus 761 and the method for utilizing the same has the advantage that the balloon 762 can be retracted without the necessity of pushing the same forwardly or distally of the cannula 766 before removal.

Still another laparoscopic apparatus 811 incorporating another embodiment of the present invention is shown in FIG. 74 which in many respects is similar to the laparoscopic apparatus 761 shown in FIGS. 71–73. Thus, it also includes the balloon 762 which is provided with a neck 763 seated against the inwardly extending taper 764 of the cannula 766. The cannula 766 is provided with the valve housing 786 and the handle 788. The valve housing 791 can be omitted because of the closed end on the tubular member 816.

The tubular member 816 has a smaller diameter portion 816a at the distal extremity and a larger diameter portion 816b at the proximal extremity with an annular taper 817 adjoining the two portions 816a and 816b and which is adapted to mate with the inwardly extending annular taper 764 provided on the cannula 766 so that the neck 763 of the balloon 762 can be sealingly engaged therebetween in the same manner as with the tubular member 771 to permit inflation of the balloon in the same manner as hereinbefore described for the apparatus 761 shown in FIGS. 71–73. However, since the tubular member 816 has a closed rounded end, the inflation medium provided in the balloon cannot escape through the tubular member 816 and for that reason there is no need for the additional sealing valve 791 provided in the embodiment of the laparoscopic apparatus 761. The tubular member 816 serves as a scope cover as in a number of the previous embodiments of laparoscopic apparatus incorporating the present invention. It can be formed of a transparent material so that viewing can be accomplished through the same and through the balloon 762 in the manner hereinbefore described.

Operation and use of the laparoscopic apparatus 811 is very similar to that hereinbefore described in conjunction with the apparatus 761 shown in FIGS. 71–73. The proximal extremity or neck 763 can be introduced on to the tapered surface 764 by wrapping it on to the tubular member 816 and drawing the neck 763 into the cannula 766 and then advancing the cannula 766 distally so that the annular taper 817 engages the neck of the balloon 762 and urges it into sealing engagement with the inwardly extending taper 764.

With the balloon 762 rolled-up in the manner hereinbefore described, the balloon 762 can be introduced with the use of the tubular member 816 as an introducer through the incision in the skin of the patient and thereafter it can be utilized to dissect tissue to place the balloon in the dissected tissue so that thereafter it can be inflated in the manner hereinbefore described. After the balloon has been deflated after completion of the dissection, the balloon can be removed by pushing the cannula 766 into the incision and then releasing the neck of the balloon 762 by removing the tubular member 816. Thereafter, the balloon 762 can be removed by pulling on the fitting assembly 799 to remove the balloon 762 through the incision outside the cannula 766. After the balloon 762 has been removed, the skin seal 781 can be advanced on the cannula into the incision to form a fluid tight seal with the skin of the patient. Thereafter, insufflation can be undertaken followed by the desired surgical procedures as hereinbefore described.

In connection with the embodiments of the invention shown in FIGS. 69 and 74, it should be appreciated that the balloon 722 can have its proximal extremity pushed forwardly through the incision 752 so that it can be removed outside of the skin seal rather than retracting it through the skin seal as in previous embodiments to make possible the use of a smaller cannula and skin seal. This can be accomplished in a number of ways, as for example by utilizing the cannula to push the proximal extremity of the balloon through the incision or, alternatively, to utilize the skin seal to push the proximal extremity through the incision. Alternatively, the scope cover 731 can be pushed in a distal direction to engage the distal extremity of the balloon to in effect pull the balloon forwardly through the incision 752. Also, alternatively, if desired, the balloon can be again partially inflated after the collar 732 has been released to permit the proximal extremity of the balloon to be pulled inwardly through the incision 752.

Yet another embodiment of the laparoscopic apparatus of the invention that may be used in conjunction with a conventional laparoscope to provide laparoscopic visualization during laparoscopic procedures as described herein is illustrated in FIGS. 75–82. Laparoscopic apparatus 849 differs from previous embodiments of the invention that provide for laparoscopic visualization during tunneling and dissection in several ways as will be explained below. Initially, it is to be noted that unlike previous embodiments, the apparatus 849 does not include a cannula and skin seal assembly as part of the obturator/balloon assembly 850. In this embodiment, the cannula and skin seal are supplied as separate units.

Figure 75:
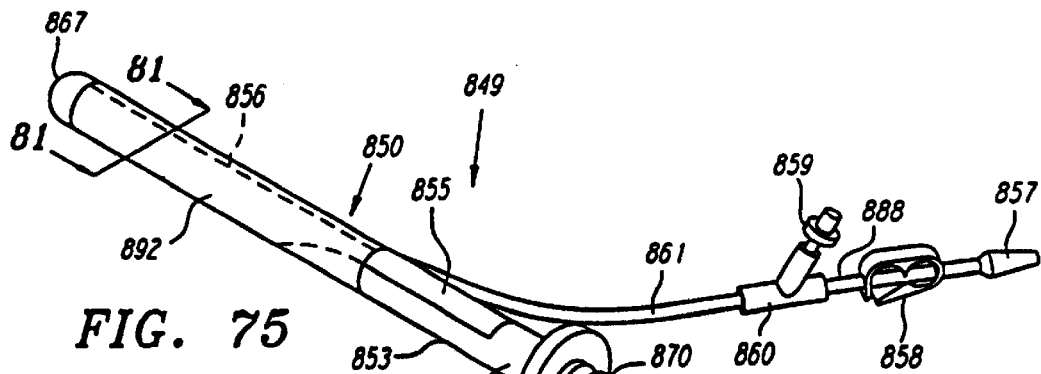
FIG. 75 is an isometric view illustrating another embodiment of a laparoscopic apparatus incorporating the present invention.
Figure 78A:
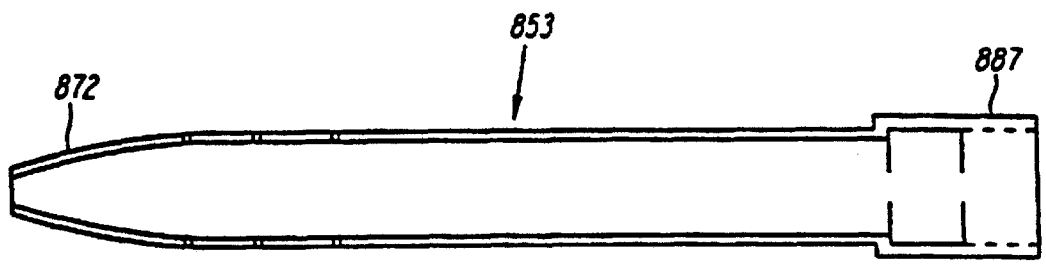
FIGS. 78A–C are plan, side elevational and end views, respectively, of a channel guide according to the invention.
Figure 78B:
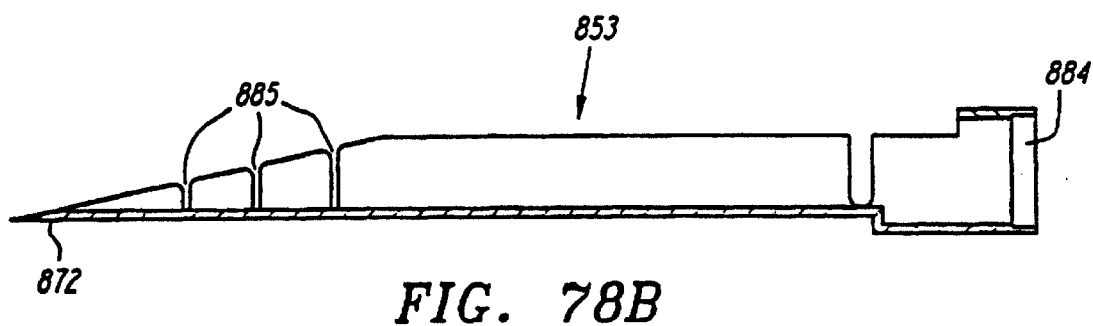
Figure 78C:
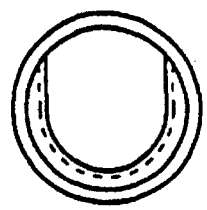

In FIG. 75, the laparoscopic apparatus 849 is shown assembled and loaded over the shaft 870 of a conventional laparoscope 862. The laparoscope has an eyepiece 863 and a fiber optic light port 897 to permit visualization of images at its distal end. In a presently preferred embodiment, the apparatus 849 has an elongated U-shaped channel guide 853 (see FIGS. 78A–C) into which a preferably transparent and substantially rigid tunneling member 851 (see FIGS. 79 and 80) formed of a suitable material, such as polycarbonate, is preferably inserted through an instrument seal (884 in FIG. 82). The tunneling member 851 serves a dual purpose. First, it functions as a scope cover into which laparoscope 862 may be inserted for visualization during tunneling and subsequent dissection. Second, together with the balloon 855 and preferably an integral balloon cover 892, it functions as a blunt tipped obturator. The U-shaped channel guide 853 is substantially rigid and is preferably formed of a suitable medical grade of plastic. As illustrated in FIG. 78B vertical slots 885 may be cut in the distal end 872 of the channel guide 853 should some flexibility of the distal end 872 be deemed necessary or desirable.

Figure 77:
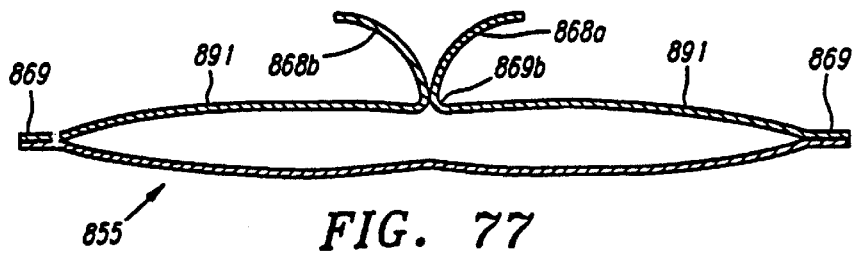
FIG. 77 is a cross-sectional view taken along line 77—77 in FIG. 76 illustrating the cross section of a balloon with an integral balloon cover according to aspects of the invention.

Turning briefly to FIGS. 77 and 81, the presently preferred transparent non-elastomeric balloon 855 may be formed from die cut sheets of an appropriate medical grade non-elastomeric plastic material, for example, and is sealed together along welds 869 such as by heat sealing. The balloon 855 is preferably provided with flaps 868a and 868b (FIG. 77) which are joined together, as shown at 869b. The right and left balloon wings 891 may be rolled-up, as shown in FIG. 81, so as to form balloon rolls 890. The flaps 869a and 869b may then be wrapped around the balloon rolls 890 and sealed together to form an integral balloon cover 892 in the manner previously described with regard to previous integral balloon cover embodiments. Thus, the balloon rolls 890 are disposed against the outer periphery of tunneling member 851 and held in position by the integral balloon cover 892 as shown in FIG. 81. The laparoscope shaft 870 can also be seen disposed within the tunneling member 851 in FIG. 81. As best seen in FIG. 75, the balloon cover 892 also covers part of the distal portion 872 of the channel guide 853 and the balloon rolls 890 that are disposed therein, along with portions of the length of the tunneling member 851. The integral balloon cover 892 thus serves to assemble the balloon 855, tunneling member 851 and the channel guide 853 into an integral package. The balloon cover 892 preferably encases all but the distal tip of the rolled-up balloon, including those portions of the balloon rolls 890 that lie disposed within the channel guide 853 to either side of the tunneling member 851. The distal tip of the balloon 855 is preferably provided with a nipple or pocket 867 that mates against the blunt distal end of the tunneling member 851 to help protect against stretching or tearing of the balloon tip 867 during tunneling. The balloon cover 892 is also provided with slits or perforations 856 that provide a weakened region in the balloon cover 892 to allow it to break open during balloon 855 inflation as previously described.

The tunneling member 851 is conveniently provided with a concentric ring shaped handle 852 for grasping by the surgeon during introduction of the obturator/balloon assembly 850 through an incision in the patient, and during tunneling to the desired location within the body for subsequent balloon tissue dissection as hereinbefore described. An instrument seal 854 is preferably provided in the proximal end of the handle 852 to make a substantially fluid tight seal between the tunneling member 851 and the laparoscope shaft 870 for reasons that will shortly become apparent.

Figure 76:
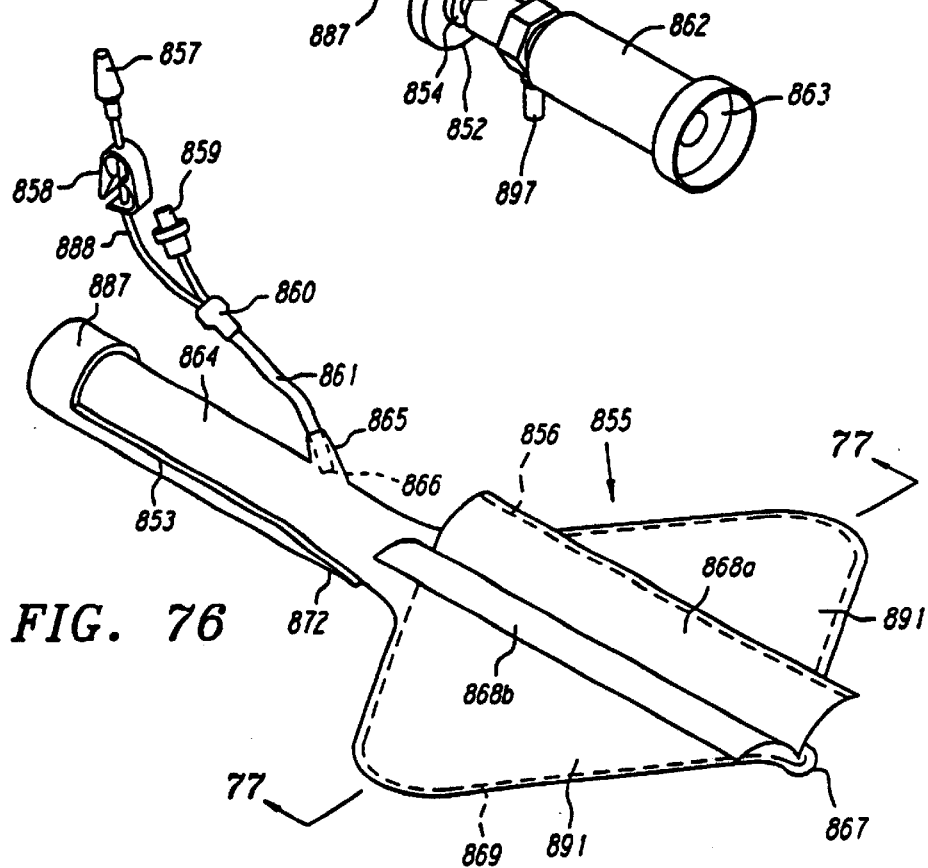
FIG. 76 is an isometric view of the laparoscopic apparatus of FIG. 75 with the laparoscope and tunneling member removed and the balloon opened up to assume a manta ray shape in accordance with one aspect of the present invention.

Turning now to FIG. 76, the balloon 855 which as shown may have a manta ray shape of the type hereinbefore described, is provided with a narrowed neck 864 through which the tunneling member 851 is inserted. The neck 864 of the balloon 855 is preferably disposed between an instrument body 876 (see FIG. 82) and the interior of the outermost ring end 887 of the channel guide 853. The balloon neck 864 is press fit between the instrument body 876 and the channel guide 853 to provide a substantially fluid tight seal with the interior of the balloon 855.

The balloon 855 is also preferably provided with a balloon inflation lumen 865 that is in communication with the interior space of the balloon 855. A flexible hollow inflation tube 861 with an open distal end 866 is inserted into the inflation lumen 865 and secured in a fluid tight manner as previously described. A wye adapter 860 is secured to the inflation tube 861 and carries a male inflation fitting 859 with an integral check valve (not shown) and another tubular member 888 on which is mounted a pinch clamp 858 and a male evacuation fitting 857, all of the type previously described.

Balloon inflation is accomplished by closing the pinch clamp 858 and after connecting the male inflation fitting 859 to a suitable fluid source, such as a syringe (not shown) for example, injecting a suitable inflation medium, such as saline, for example, through the inflation tube 861 into the balloon inflation lumen 865 and into the interior of the balloon. When the balloon 855 is inflated, the integral balloon cover 892 is designed to separate along its weakened region (represented by perforations or slits 856 in FIGS. 75 and 76) to allow the balloon 855 to expand as it unrolls and climbs out of the open distal portion of the channel guide 853 until it is fully expanded. The balloon 855 may be deflated by connecting the evacuation fitting 857 to an evacuation port (not shown) such as an operating room suction system, for example. The pinch clamp 858 is released to open the tube 888 to permit the saline solution which had been introduced into the balloon 855 to be sucked out through the inflation lumen 865 to completely deflate the balloon 855.

With reference to FIGS. 79 and 80, in a preferred embodiment, the hollow tunneling member 851 is provided with an open distal end 893 so that the distal end 895 of the laparoscope shaft 870 may be extended through this open end 893 during balloon 855 inflation as illustrated in FIG. 80. By extending the distal end 895 of the laparoscope 862 outside the tunneling member 851 only a single transparent balloon layer obstructs laparoscopic visualization and increased resolution over previous embodiments is possible. As illustrated in FIG. 79, the tunneling member 851 is provided with spaced apart slits 894 at its distal end. The slits 894 allow the distal open end 893 of the tunneling member 851 to expand slightly outwardly, thus permitting the distal end 895 of the laparoscope 862 to be advanced outside the tunneling member 851. Because the end of the tunneling member 851 is open to the interior of the balloon 851 during inflation, an instrument seal 854 is provided at the proximal end of the tunneling member 851 to minimize leakage of the inflation medium from the proximal handle 852 portion during inflation. Alternately, or in combination with instrument seal 854, the tunneling member 851 may have a necked down portion, as illustrated at 887 in FIG. 82, to form a substantially fluid tight seal between the tunneling member 851 and the scope shaft 870 to protect against leakage out the proximal end of the tunneling member 851.

Figure 82:
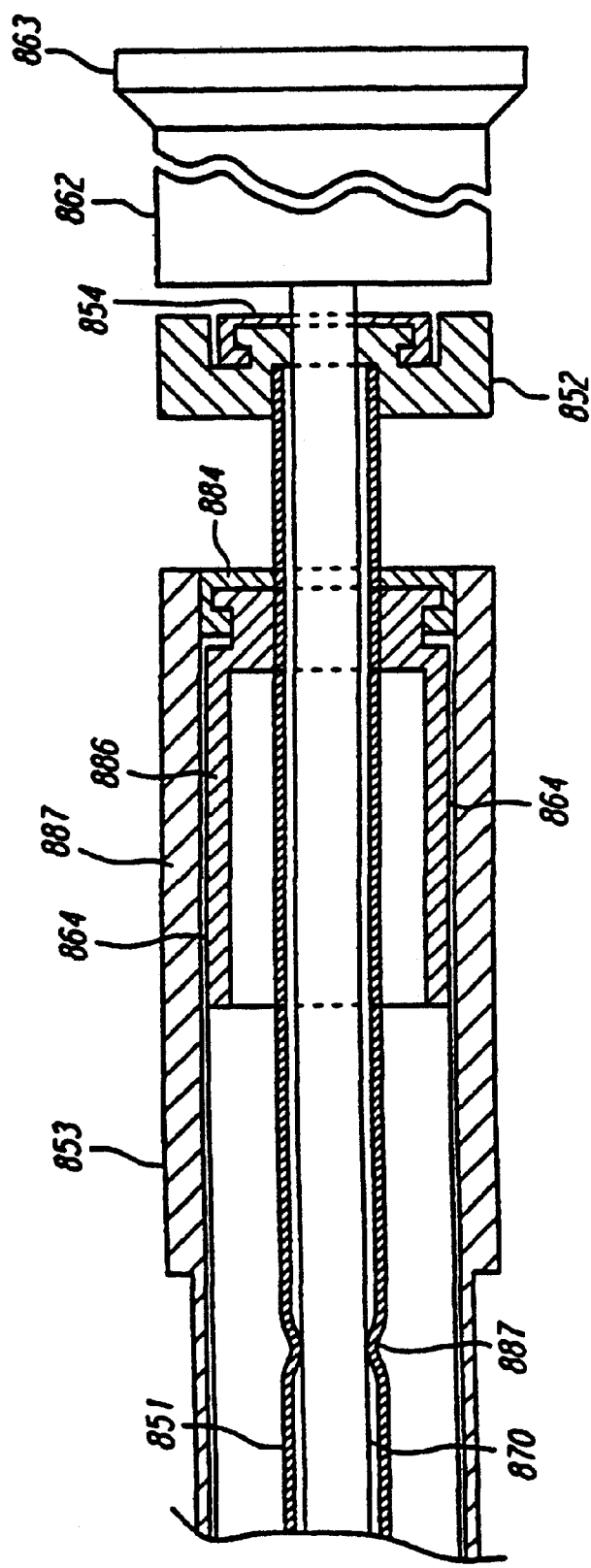
FIG. 82 is a cross-sectional view of the proximal end of the FIG. 75 laparoscopic apparatus.

The cut-away cross section in FIG. 82 shows the proximal portion of the laparoscopic apparatus 849. As previously discussed, the balloon neck 864 is trapped in a fluid tight manner between the proximal ring 887 of the channel guide 853 and the outer periphery of cylindrical instrument body 886. Thus, the interior of the balloon 855 is sealed at the proximal extremity of its elongated neck 864 by means of a press fit between the proximal ring 887, the neck 864, and the instrument body 886. A cylindrical shaped tunneling member seal 884 of the type previously described is preferably inserted over the proximal end of the instrument body 886 to form a substantially fluid tight seal between the tunneling member 851 and the channel guide 853. This seal 884 is used to prevent fluid from coming out the proximal end of the channel guide 853 during balloon 855 inflation.

Figure 83:
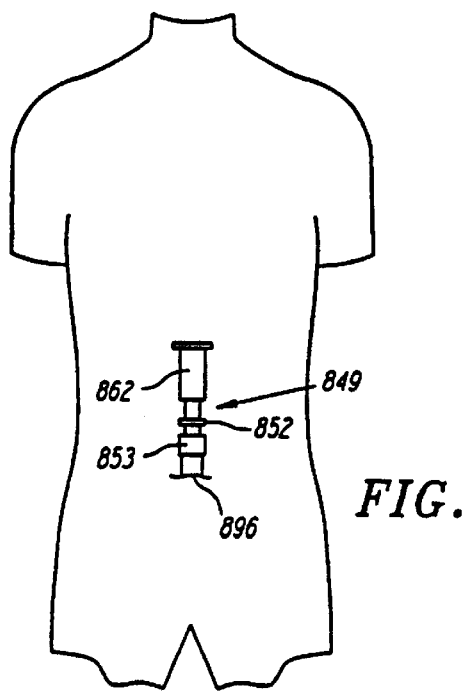
FIG. 83 is a cartoon showing the use of the laparoscopic apparatus shown in FIG. 75 in a laparoscopic hernia repair.

Operation and use of the laparoscopic apparatus 849 may now be briefly described with reference to FIG. 83. After the laparoscopic apparatus 849 has been readied for use, a conventional laparoscope is inserted through the instrument seal 854 and into the hollow lumen of the tunneling member 851 until resistance is felt and the distal extremity 895 of the laparoscope shaft 870 can be assumed to rest against the distal extremity of the tunneling member 851. The surgeon next makes an incision 896 using conventional techniques at the appropriate location in the body of the patient. The incision location, of course, depends on the operation to be performed and is illustrated with regard to hernia repair in FIG. 83 by way of example only. After making the incision 896, the apparatus 849 is oriented so that the open side of channel guide 853 faces away from the patient, and the distal extremity of the apparatus 849 is advanced through the incision. The distal extremity of the apparatus 849 is then used as an obturator to tunnel through the appropriate tissue layers until the location of interest for subsequent balloon inflation and tissue dissection is found. As the distal extremity of the apparatus 849 is being advanced through the tissue layers, the progress of the operation may be observed through the laparoscope 862 to aid the surgeon in locating important anatomical landmarks. As hereinbefore described with regard to previous embodiments, during this tunneling stage, the distal end 895 of the laparoscope 862 looks out through the open end 893 in the distal extremity of the tunneling member 851 and the distal portion of the balloon 867 which covers it. A straight tipped scope 862 will give the greatest field of view out the distal opening 893 during the tunneling process, but an angled scope 862 (as illustrated in FIG. 80) may be used instead.

After the desired location in the body has been found, perhaps with the aid of visual observation and manual palpation in addition to laparoscopic observation, dissection can proceed to create an anatomic working space. It should be noted that the tunneling member 851 should be sized to an appropriate length for the particular operation being performed so that the channel guide 853 is advanced approximately half of its length through the incision when tunneling is completed. After the balloon suction pinch clamp 858 has been closed so as to seal off the suction line, balloon inflation may proceed through the inflation fitting 859 as previously explained.

During inflation the tunneling member 851 and laparoscope 862 may be pulled back slightly from the balloon by grasping the handle 852 and pulling back with one hand while holding the channel guide 853 in position with the free hand. The distal portion of the laparoscope shaft 895 may then be advanced through the open distal end 893 of the tunneling member 851, forcing open slits 894, to permit an unobstructed view from inside the balloon 855 of tissue dissection as the balloon 855 unrolls and inflates as previously described. If an angular laparoscope is employed, the scope may be rotated or otherwise manipulated at the proximal end so as to increase the field of view from within the balloon 855.

After inflation is complete, the balloon may be deflated by opening the suction line pinch clamp 858 and applying suction through male fitting 857 by suitable means such as a syringe or an operating room suction line as previously described. Once deflated, the channel guide 853 may be held in position and the tunneling member 851 and laparoscope 862 completely withdrawn from the channel guide 853 and balloon 855, either together or sequentially, leaving the channel guide 853 and deflated balloon 855 within the incision 896 to provide a path back to the previously dissected space.

Next, the tunneling member 851 is discarded and a trocar with cannula and skin seal assembly of the type hereinbefore described with reference to FIG. 40, may be slid over the distal end 895 of laparoscope 862. While holding the channel guide 853 in place, the distal end 895 of the laparoscope 862 may be inserted back into the incision 896 site and advanced into the previously dissected space using the channel guide 853 to guide the scope shaft 870. While holding the laparoscope 862 together with the trocar, cannula and skin seal assembly, the channel guide 853 and the attached deflated balloon 855 may now be removed from the patient through the incision 896. At this point, the trocar with cannula and skin seal assembly can be advanced over the laparoscope shaft 870 into the incision 896 and the skin seal secured in place as previously described. The operation may now proceed in the manner appropriate for the particular procedure being performed.

Figure 84:
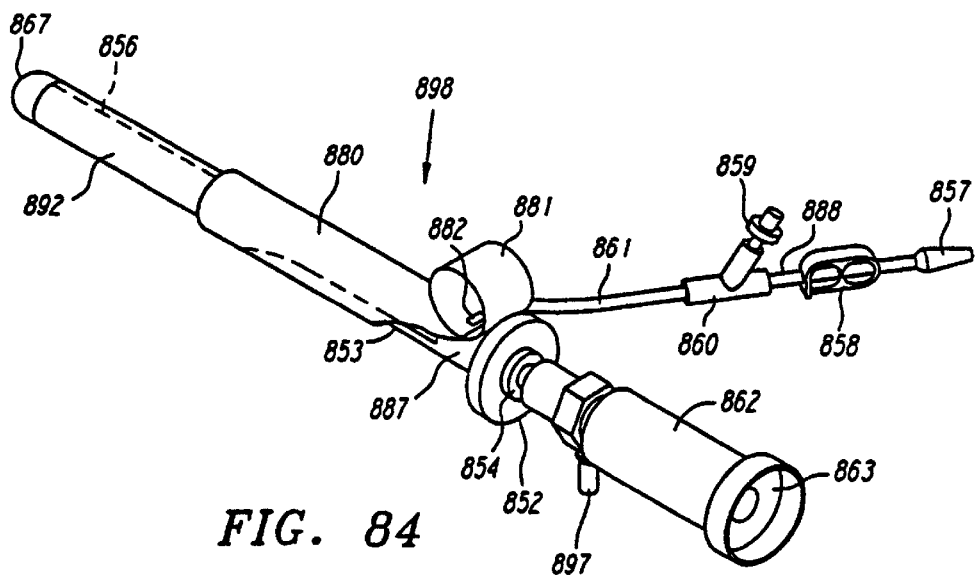
FIG. 84 is an isometric view of another embodiment of a laparoscopic apparatus incorporating the present invention.
Figure 86:
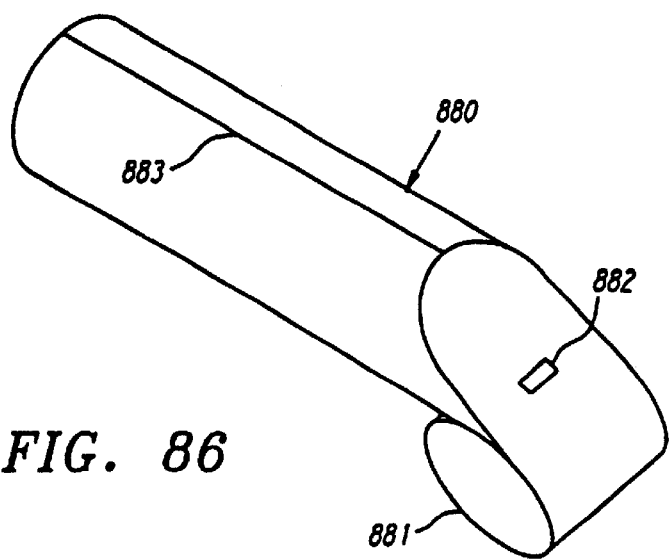
FIG. 86 is an isometric view of the underside of the endoscope guide member utilized in the FIG. 84 and 85 embodiments according to another aspect of the invention illustrating its full length longitudinal slit.

Turning now to FIG. 84, yet another embodiment of the invention is illustrated that adds the use of an endoscope guide member 880 to the laparoscopic apparatus 849 illustrated in FIG. 75. The apparatus 898 is otherwise identical. Guide member 880 consists of a semi-rigid tube with that may be formed of a suitable material such as plastic. As illustrated in FIG. 86, guide member 880 is provided with a longitudinal slit 883 running the length of the tube portion to facilitate its removal from the apparatus 898 in accordance with the laparoscopic procedures described below.

In a preferred embodiment, the endoscope guide 880 may be positioned over the channel guide 853, balloon 855, and tunneling member 851 assembly with its handle 881 oriented in the same direction as the open portion of the U-shaped channel guide 853 which it partially surrounds. As shown in FIG. 86, the endoscope guide 880 is provided with a slit 883 that extends longitudinally along the complete underside of the guide 853. The slit 883 allows the endoscope guide 880 to separate from the balloon 855, channel guide 853, and tunneling member 851 assembly as the balloon 855 is inflated after the tunneling member 851 has been advanced to dispose the balloon 855 within the desired location.

In a preferred embodiment, the endoscope guide 880 is also provided with a rolled over handle 881 secured by appropriate means such as staple 882 to the guide 880 as illustrated in FIG. 84. The handle 881 at all times remains outside the incision where it can be accessed by the surgeon. After balloon deflation, the distal portion of the endoscope guide 880 remains within the incision to preserve access to the previously created space and provide a convenient means for guiding the laparoscope 862 back into the space.

Use of the laparoscopic apparatus 898 is substantially similar to that previously described with regard to the embodiment shown in FIG. 75. As before, a conventional laparoscope 862 is inserted into the bore of the tunneling member 851 until its distal end 895 bottoms against the distal end of the tunneling member 851 bore. After an incision is made in the desired location, the tunneling member 851 together with the rolled up balloon 855 is inserted into the incision and advanced as an obturator to the desired location. Visualization during tunneling dissection is as described before. The apparatus 898 is sized so that approximately half of the channel guide 853 and the proximal handle 881 portion of the endoscope guide 880 remain outside the incision when the desired location has been reached. The tunneling member 851 together with the laparoscope 862 may be retracted from against the distal end 867 of the balloon 855 during inflation so as to provide the necessary clearance from the interior of the balloon to permit the distal end 895 of the laparoscope 862 to be advanced outside the open end 898 of the tunneling member 851. Dissection may then be viewed through a single balloon layer during inflation as before.

The addition of the endoscope guide 880 slightly alters the procedure after deflation of the balloon 855. After balloon deflation, the tunneling member 851 and laparoscope 862 are completely removed from the channel guide 853 and balloon 855, thus leaving the endoscope guide 880, the channel guide 853, and the deflated balloon 855 in place within the incision. The next step in this procedure is while holding the endoscope guide 880 in place, to remove the channel guide 853 and the attached balloon 855 through the incision. After discarding the tunneling member 851 and loading a trocar with cannula and skin seal assembly over the laparoscope 862, the distal end 895 of the scope 862 is inserted back into the incision using the endoscope guide 880 as a path to the dissected space. After the space has been located, the endoscope guide 880 may be removed from the patient and the cannula/skin seal advanced and secured into the incision as before.

Figure 85:
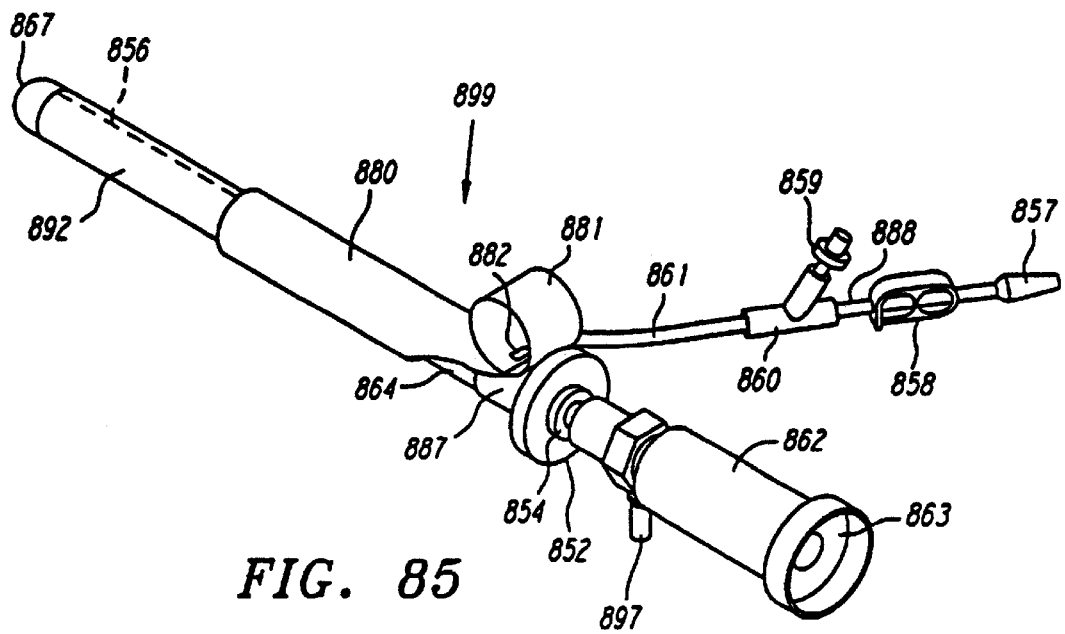
FIG. 85 is an isometric view of still another embodiment of a laparoscopic apparatus incorporating the present invention.

Another embodiment of the laparoscope apparatus incorporating the invention is illustrated in FIG. 85. The laparoscopic apparatus 899 in this embodiment differs from the previous FIG. 84 embodiment in that the longitudinally extending open ended distal portion of the channel guide 853 has been cut away, leaving only the proximal ring 887 portion and the inner press fit instrument body 886 to seal the balloon neck 864 as previously described.

Use of this apparatus 899 is substantially similar to that of the previous two embodiments. The apparatus 899 is introduced into an incision in the body; advanced to the desired location under laparoscopic observation with the blunt tipped tunneling member 851 serving as an obturator; the balloon 855 is then inflated under laparoscopic observation, if desired, to achieve tissue dissection; and the balloon 855 deflated, all as hereinbefore described. The tunneling member 851 and laparoscope 862 are then withdrawn from the incision through the ring 887 leaving the deflated balloon 855 and endoscope guide 880 in place. While holding the endoscope guide 880 in place, the ring 887 and attached balloon neck 864, which at all times remains outside the incision, is grasped and pulled away from the patient to withdraw the deflated balloon 855 from the body through the incision. After the tunneling member 851 has been discarded, and the trocar with cannula and skin seal assembly loaded over the laparoscope 862, the distal tip 895 of the laparoscope 862 is guided into the incision and the previously created space using the endoscope guide 880 as a guide as previously described. The remainder of the procedure is identical to that described with reference to FIG. 84.

Turning now to FIGS. 87–92, yet another laparoscopic apparatus that provides for laparoscopic observation during tunneling and subsequent balloon dissection or retraction is illustrated. In FIG. 87 the laparoscopic apparatus 900 of this embodiment is illustrated in a fully assembled state as it would be prior to insertion through an incision into the human body for the performance of laparoscopic procedures as explained herein.

In a preferred embodiment, laparoscopic apparatus 900 includes a tunneling member 913, handle 902, and balloon sleeve 903 together with a balloon (926 in FIGS. 90 and 91) and integral balloon cover 908. The tunneling member 913 is inserted through the handle 902 and sleeve 903 into the interior of the balloon 926. In FIGS. 87 and 89, the balloon 926 is illustrated after it has been rolled or folded and secured to the distal portion of the tunneling member 913 by means of an integral balloon cover 908 in the manner described with regard to prior integral balloon cover embodiments. The integral balloon cover 908 is provided with slits or perforations 907 that permit the cover to separate and break away during balloon expansion as previously described. As illustrated in FIGS. 88 and 89, a conventional laparoscope 909 may be inserted into the tunneling member 913 if laparoscopic observation is desired. Thus, together with the rolled or folded balloon 926 and the integral balloon cover 908, the tunneling member 913 serves as both a blunt tipped obturator and a laparoscope cover.

The tunneling member 913, which may be formed of a suitable medical grade of plastic, such as polycarbonate, comprises an obturator shaft 915, and an obturator handle 904. Handle 904 facilitates grasping and manipulation by the surgeon during performance of an operation. The obturator shaft 915 is preferably transparent, and sufficiently rigid to permit tunneling through tissue layers within the human body. The tunneling member 913 is provided with a hollow bore extending through its entire longitudinal length from the proximal handle 904 portion to the distal open ended tip 917 to accept the insertion of a conventional laparoscope 909 (see FIG. 88).

Figure 90:
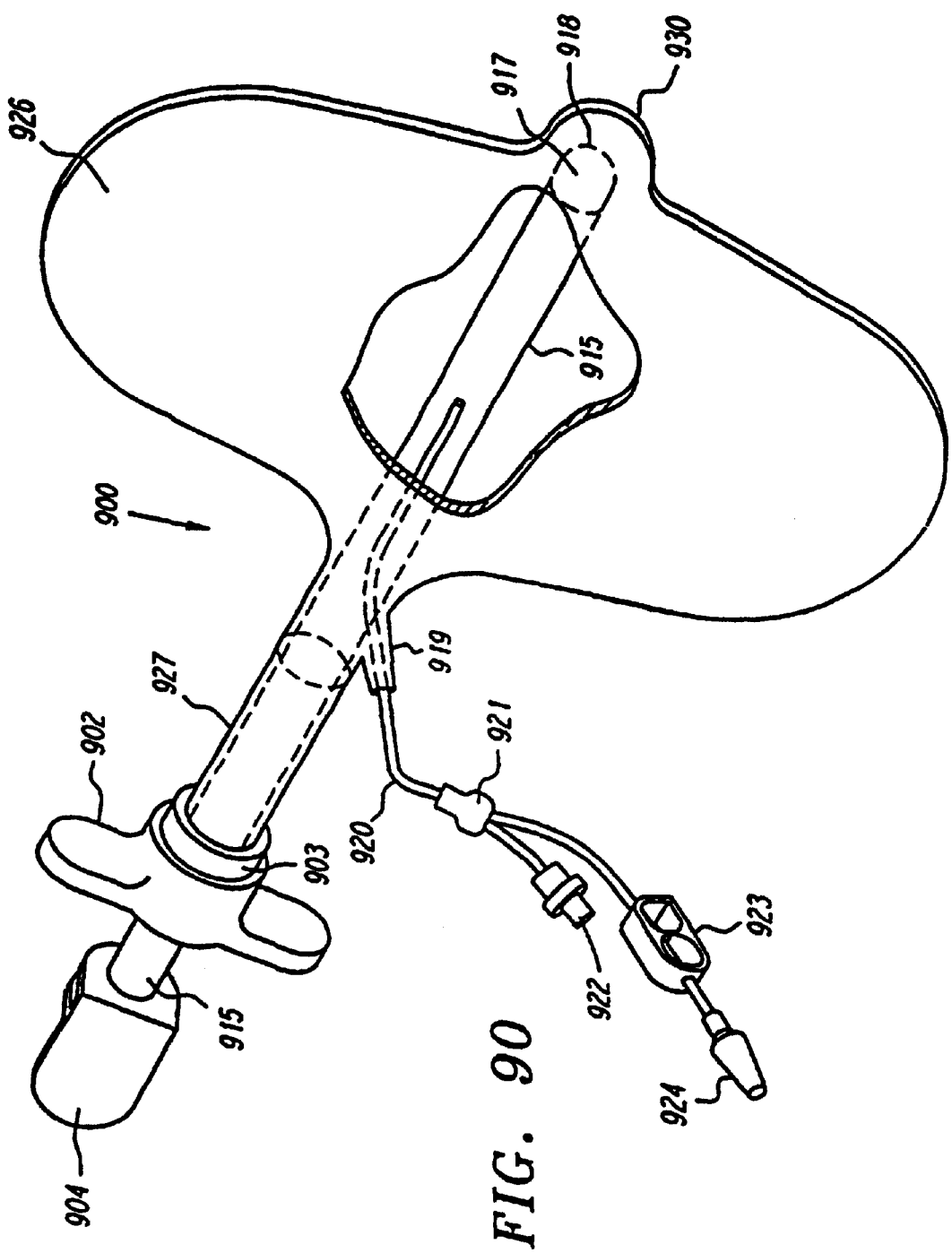
FIG. 90 is an isometric view of the FIG. 87 embodiment of the invention in partial cut-away, with the balloon unrolled and laid flat.
Figure 91:
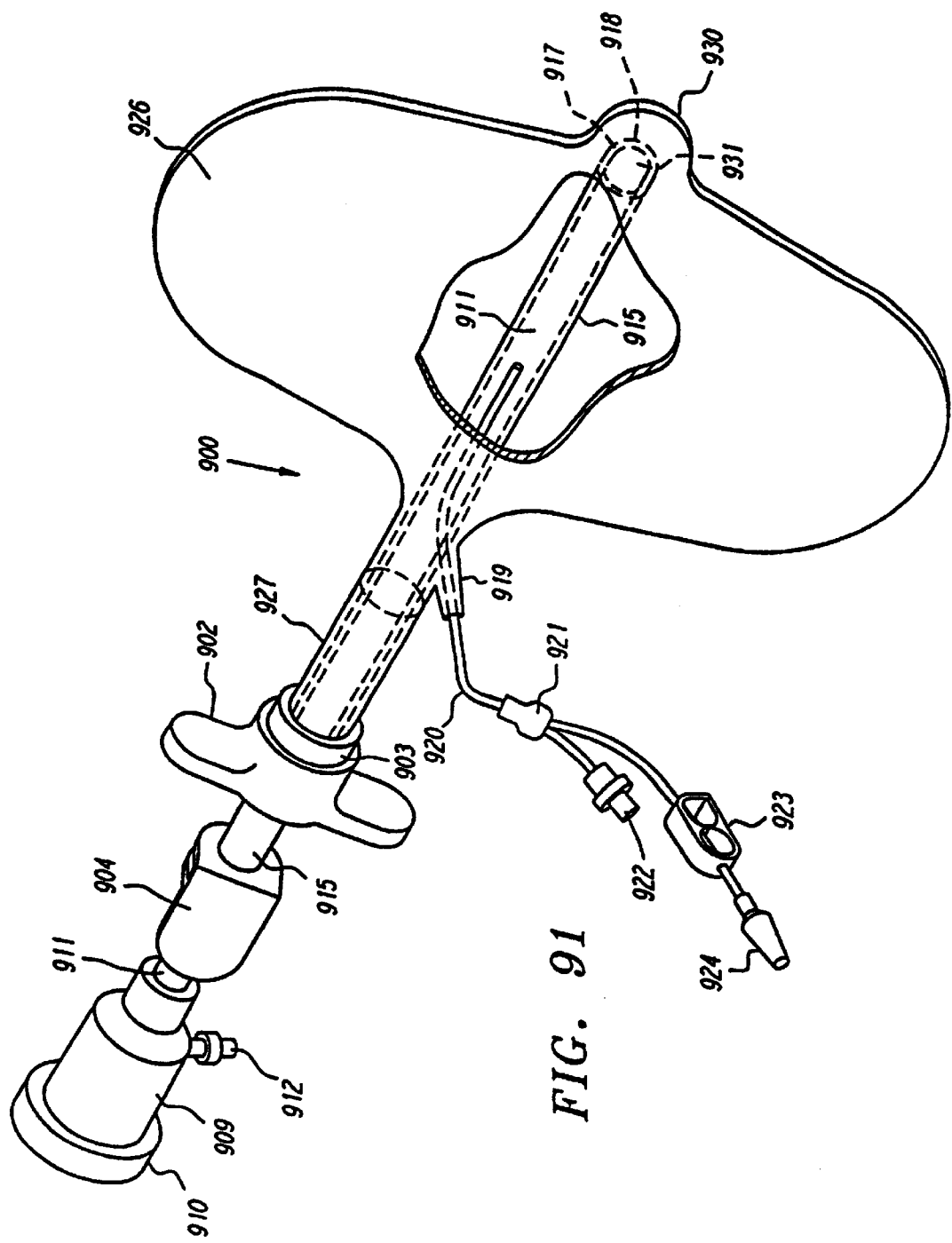
FIG. 91 is an isometric view substantially similar to the FIG. 90 view illustrating the insertion of a laparoscope into the apparatus to permit laparoscopic observation during both tunneling and balloon expansion according to aspects of the present invention.

In a preferred embodiment, the tunneling member 913 is removably inserted through the bore (see cross-sectional view in FIG. 92) provided in handle 902 and balloon sleeve 903, and into the interior of the rolled or folded balloon 926 (FIGS. 90 and 91). Like the tunneling member 913, the handle 902 and balloon sleeve 903 may be formed of a suitable medical grade plastic, such as polycarbonate. As best illustrated in the cross-sectional view in FIG. 92, the proximal end of balloon sleeve 903 mates against the distal portion of the handle 902 and is secured in mating engagement therewith by the elongate balloon neck 927 which surrounds the sleeve and extends into the handle 902. The balloon neck 927 is secured between the interior of the handle 902 and the external periphery of the instrument body 933 by means of a press fit between the handle 902 and the body 933. The press fit between the handle 902 and the body 933 traps the balloon neck 927 therebetween and provides a substantially fluid tight seal for the interior of the balloon 926.

Because the handle 902 is in communication with the interior of the balloon 926, seals 932 are inserted at the proximal and distal ends of the instrument body 933 to provide a substantially fluid tight seal between the interior bore of the handle 902 and the obturator shaft 915 which passes through the handle 902. The seals 932 prevent the balloon inflation medium, typically saline, from flowing out the proximal end of the handle 902. The seals 932 also add stability to the obturator shaft 915 relative to the instrument body 933 in the handle 902 that the shaft 915 passes through.

The balloon 926 is provided with an inflation lumen 919 in communication with the interior space of the balloon 926 for delivering a suitable inflation medium, such as saline solution, to the interior of the balloon 926. A flexible hollow inflation tube 920 with an open distal end is inserted into the balloon inflation lumen 919 and secured in a fluid tight manner as previously described. A wye adapter 921 is secured to the inflation tube 920 and carries a male inflation fitting 922 with an integral check valve (not shown) and another tubular member on which is mounted a pinch clamp 923 and a male evacuation fitting 924, all of the type previously described. The balloon 926 is inflated and deflated in the same manner as described with regard to prior embodiments.

When assembled into a complete assemble (as illustrated in FIG. 87), the obturator shaft 915 of the tunneling member 913 passes through the handle 902 and balloon sleeve 903 bores and extends into the interior of a rolled balloon 926 (illustrated unrolled and flattened out without the flaps that preferably comprise the integral balloon cover 908 in FIGS. 90 and 91) until the open distal end 917 of the obturator shaft 915 presses against a nipple 930 provided in the balloon 926. As best illustrated in FIGS. 90 and 91, showing the apparatus 900 with the balloon 926 unrolled and laid flat, a nipple or pocket 930 is provided in the balloon 926 to accept the open distal end 917 of the obturator shaft 915. Use of the nipple 930 helps to prevent stretching or tearing of the balloon 926 during tunneling when the open distal end 917 of the obturator shaft 915 presses against the balloon material of the nipple 930. The balloon 926 may have a manta ray shape as illustrated in FIGS. 90 and 91, or it may be custom shaped for the particular procedure to be performed.

In FIG. 89, a conventional laparoscope 909 is illustrated after it has been fully inserted into the apparatus 900 to permit observation through its distal end (not shown) during tunneling and dissection. The laparoscope 909 includes a shaft 911 that is inserted through a bore in the tunneling member 913 that extends from the proximal handle 904 portion to the open ended distal tip 917 (FIG. 88). To prepare for tunneling dissection, the laparoscope 909, which may be a conventional 10 mm laparoscope, for example, is inserted through the handle portion 904 of the tunneling member 913 and advanced through the tunneling member bore 914 until the distal extremity 931 of the scope shaft 911 is captured by the lip 918 provided in the obturator shaft 915. The lip 918 in the obturator shaft 915 thus prevents further advancement of the laparoscope shaft 911, and retains the distal end 931 of the shaft 911 within the confines of the obturator shaft 915. The laparoscope 909 is provided with a fiber optic light port 912 to provide illumination to the lens (not shown) located at the distal end of the scope shaft 931. Although an angled scope will provide the best visualization through the cut-away distal end 917 of the obturator shaft 913, a straight scope may also be utilized.

Figure 92:
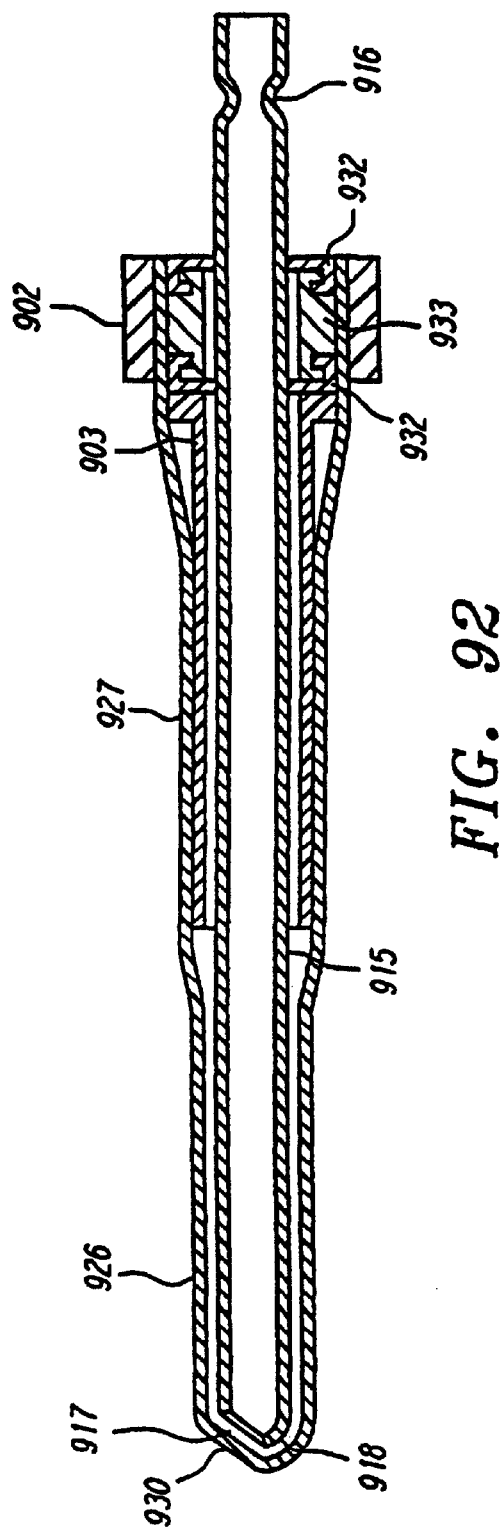
FIG. 92 is a cross-sectional view of the FIG. 87 apparatus, showing the sealing of the elongate balloon neck between the handle and an internal instrument body.

As illustrated in FIG. 92, the distal end 917 of the obturator shaft 915 is cut away at approximately a 45 degree angle to provided an open end for unobstructed vision through the laparoscope 909 during both tunneling and subsequent balloon dissection. An instrument seal 916, which may comprise a pinched down region of the obturator shaft 915 as illustrated in FIG. 92, provides a substantially fluid tight seal between the laparoscope shaft 911 and the interior of the obturator shaft 915 to prevent the balloon inflation medium from escaping out the proximal end of the tunneling member 913 during balloon inflation. As an alternative to the pinch seal 916, or in addition thereto, an instrument seal of the type illustrated between the handle 902 and obturator shaft 915 may be provided in the bore at the proximal end of the obturator handle 904 as previously described and illustrated with regard to the FIG. 75 embodiment.

During surgical use of the apparatus 900 as described herein, important physical structures and anatomical landmarks may be observed at the distal end 931 of the scope shaft 915 through eyepiece 910 (or viewing monitor, not shown) to guide the surgeon in locating the correct dissection plane. As can be appreciated from the construction of the apparatus 900 described above, by providing a cut away distal end 917 in the obturator shaft 915, the surgeon's vision through the laparoscope 909 during both tunneling and subsequent balloon 926 expansion is impeded by only a single balloon 926 layer. After balloon inflation, when the balloon 926 has broken free of its cover 908 and separated from the obturator shaft 91 5, the tunneling member 913 together with the laparoscope 909 may be advanced or retracted relative to the stationary handle 902 and balloon sleeve 903 assembly which remain outside the incision in the patient.

The surgical procedure for use of apparatus 900 may now be briefly described. After the laparoscopic apparatus 900 has been readied for use, a conventional laparoscope 909 is inserted into the tunneling member 913, and advanced through the pinch seal 916 until the distal extremity 931 of the laparoscope shaft 911 is captured by lip 918. The surgeon next makes an incision using conventional techniques at the appropriate location, depending on the operation to be performed, in the body of the patient. After making the incision, the apparatus 900 is advanced through the incision with the distal extremity of the apparatus 900 being used as an obturator to tunnel through the appropriate tissue layers until the location of interest is located. As the distal extremity of the apparatus 900 is being advanced through the tissue layers, the progress of the operation may be observed through the laparoscope 909 to aid the surgeon in locating important anatomical landmarks. As described with reference to previous embodiments, during this tunneling stage the distal end 931 of the laparoscope 909 looks out through the open (preferably cut at a 45 degree angle) distal end 917 of the obturator shaft 915 obstructed by only a single and preferably transparent balloon layer.

After the desired location in the body has been found, dissection or retraction, as appropriate for the procedure, may be performed. It should be noted that the obturator shaft 915 is sized to an appropriate length for the particular operation being performed. After the balloon suction pinch clamp 923 has been closed so as to seal off the suction line, balloon inflation may proceed through the inflation fitting 922 as previously explained.

During inflation the tunneling member 913 and laparoscope 909 may be pulled back slightly from the balloon 926 by grasping the tunneling member handle 904 and pulling back with one hand while holding the handle 902 in position with the free hand. The laparoscope 909 together with the tunneling member 913 may then be manipulated, and rotated as desired for unobstructed viewing from inside the balloon 926 of tissue dissection as the balloon 926 unrolls and inflates as previously described.

After inflation is complete, the balloon 926 may be deflated by opening the suction line pinch clamp 923 and applying suction through male fitting 924 by suitable means such as a syringe or an operating room suction line as previously described. Once deflated, the laparoscope 909, tunneling member 913 and the handle 902, balloon guide 903 and secured balloon 926 may be withdrawn, either together or sequentially through the incision.

If insufflation is required for the procedure or additional trocars are needed, a trocar with cannula and skin seal assembly of the type hereinbefore described with reference to FIG. 40 may be used. In this case, the trocar with cannula and skin seal is first loaded over the distal end 931 of the laparoscope 909. The laparoscope 909 is then inserted back into the incision to access the previously created space, and the trocar with cannula and skin seal assembly may be advanced over the laparoscope shaft 911 into the incision and the skin seal secured in place as previously described.

Figure 93:
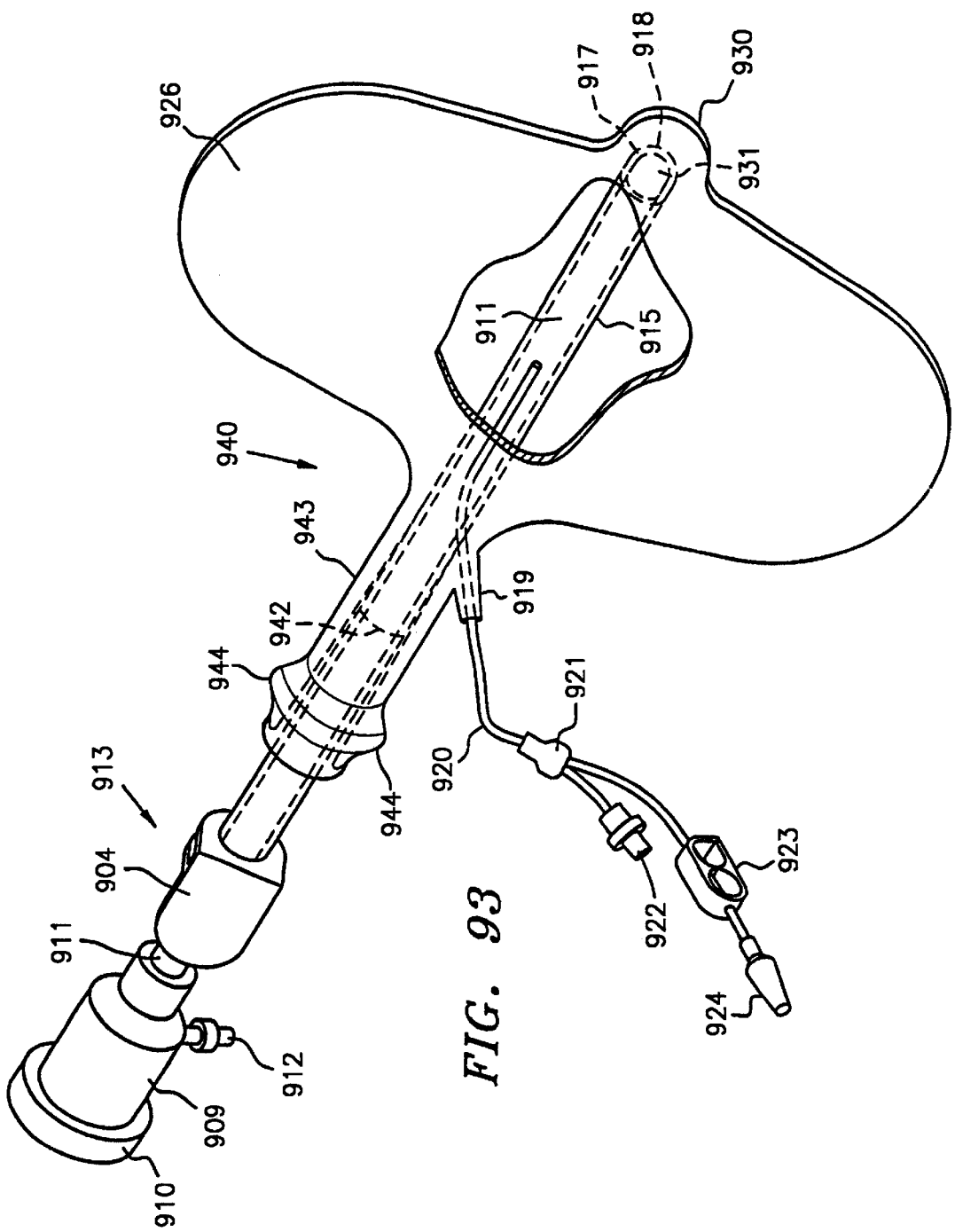
FIG. 93 is yet another embodiment of a laparoscopic apparatus according to the invention that provides for the insertion of a conventional laparoscope to permit viewing of laparoscopic procedures as described herein.

A greatly simplified embodiment that provides for laparoscopic observation both during tunneling and balloon dissection after the desired location has been reached is illustrated in FIG. 93. The laparoscopic apparatus 940 includes a tunneling member 913 of the type previously described with reference to the FIG. 87 embodiment, a balloon 926 with an elongate neck 943, and an inflation lumen 919. The elongate neck 943 may be folded inwardly and secured to the shaft 915 of the tunneling member 913 as illustrated at 942. The neck 943 is preferably secured to the obturator shaft 915 by means of clamping, gluing, heat sealing or welding as previously described. Alternatively, the proximal end of the elongate neck 943 may be sealingly secured to a handle 904 on the shaft 915 or the proximal end of the shaft 915 where it meets the handle 904 (similar to the attachment of the balloon to the handle as shown and described with respect to the embodiments of FIGS. 87–92 above and FIG. 100 below). Additionally, any one of a number of folding arrangements, including a multiplicity of folds, may be employed with regard to the balloon neck 943.

In a further aspect of the present invention, the balloon neck 943 may be provided with one or more handles 944 on the exterior of the neck 943 to facilitate assembly and folding of the balloon neck 943. The handles 944 may simply be formed by a slight enlarging of the neck diameter as shown in FIG. 93. The handles 944 are preferably located at the proximal extremity of the outside layer of the balloon neck 943 in the folded condition. Alternatively, the handles 943 may be formed by attaching one or more tabs, loops or other structure that can be easily grasped onto the balloon neck 943 at the appropriate location. When assembling or preparing for use the laparoscopic apparatus 940, the balloon neck 943 can be folded by grasping the handles 944 and pulling proximally such that the portion of the neck 943 attached to the handles 944 slides over the underlying neck portion causing the neck 943 to fold inwardly. The neck 943 may be folded inwardly until the distal end 930 of the balloon 926 contacts the distal end of the obturator shaft 915.

t is contemplated that any of the balloon embodiments disclosed herein may be provided with an elongated neck that may be folded inwardly and/or handles such as those just described. For example, the embodiment of FIGS. 87–92, described above, may be provided with an elongated neck which in a unfolded state leaves adequate room between the distal tip 930 of the obturator shaft 915 and the distal tip 930 of the balloon 926. This allows inflation of the balloon 926 without being constricted by the distal tip of the obturator shaft 915 as the balloon inflates from its flat uninflated state.

By providing this inward folding of the elongate neck 943, the tunneling member 913 and inserted laparoscope 909 may be retracted from the balloon 926 to obtain a desirable focal length and may then be manipulated to view an area of interest, without moving the position of the balloon 926 relative to the desired location. Viewing may be conducted at any time during the procedure, including during tunneling, prior to inflation, during inflation and after the balloon has been fully inflated. In addition permitting pullback of the tunneling member 913, the folded neck 943 also gives the balloon 926 sufficient slack so that as the balloon 926 inflates and expands, it is not constricted by the distal tip 930 of the balloon bearing against the distal tip of the obturator shaft 915. Because the balloon is flat in its uninflated state, as the balloon is inflated, it expands laterally out of the plane of the flat balloon. As the balloon expands out of the flat plane, the perimeter of the balloon is pulled and moves toward the area of expansion. This shortens the balloon in the longitudinal direction and narrows the balloon in the lateral direction. It should be noted that the hollow obturator shaft 915 may be replaced by a solid obturator where it is not necessary to insert a device into the obturator, for example, where visualization is not desired.

The tunneling member 913 is as previously described with a handle 904 at its proximal end and a hollow obturator shaft 915 extending distally from the handle 904. The obturator shaft 915 is sized to accept a conventional laparoscope and is provided with an open distal end 917 with lip 918 to capture the distal end of the laparoscope when inserted. The distal end 917 is preferably cut-away at a 45 degree angle as before to facilitate observation during tunneling.

In FIG. 93, the balloon 926 is shown unrolled and flattened out to illustrate the open distal end 917 of the obturator shaft 915 and the laparoscope shaft 911 that is inserted therein. The distal end 931 of the laparoscope is captured by the lip 918 provided in the obturator shaft 915. In practice, the balloon 926 would be rolled or folded and secured relative to the distal portion of the obturator shaft 915 by means of an integral balloon cover (not shown) in the manner previously described. Alternatively, the endoscope guide 880 (illustrated in FIG. 86) may be used to secure the rolled or folded balloon in place about the obturator shaft 915. The endoscope guide 880 may be used in place of, or in addition to, an integral balloon cover. One advantage of using the endoscope guide 880 is that it may be left within the incision to preserve access to the dissected space after balloon deflation and removal as described with reference to the FIGS. 84 and 85 embodiments and further described herein. Use of the apparatus 940 offers the advantage of permitting greatly simplified surgical procedures over previous embodiments. As with the FIG. 87 embodiment, a conventional laparoscope 909 is inserted into the tunneling member 913 and is advanced through pinch seal 916 (see FIG. 92) until the distal extremity 931 of the laparoscope shaft 911 is captured by lip 918. After an incision is made in the patient, the apparatus 940 is advanced through the incision with the distal extremity of the apparatus 940 being used to tunnel through the appropriate tissue layers until the location of interest is reached. If the optional endoscope guide 880 is used, the handle 881 of the guide 880 will remain outside the incision to facilitate later removal. As before, the progress of the operation may be observed through the laparoscope 909 during tunneling dissection. During this tunneling stage, the distal end 931 of the laparoscope 909 looks out through the open distal end 917 of the obturator shaft 915 obstructed by only a single and preferably transparent balloon layer.

After the desired location in the body has been reached, dissection or retraction, as appropriate for the procedure, may be performed. The balloon suction pinch clamp 923 is closed to seal off the suction line, and the balloon 926 is inflated through the inflation fitting 922 as previously explained. If the optional endoscope guide 880 is used, the guide 880 separates from the rolled up balloon 926 as the balloon 926 inflates to permit the balloon 926 to freely unroll and expand.

In a preferred method of use, during inflation the tunneling member 913 and laparoscope 909 are pulled back slightly from the nipple 930 of the balloon 926 by grasping the tunneling member handle 904 and retracting the tunneling member 913 and laparoscope 909. The laparoscope 909 and tunneling member 913 may then be manipulated and rotated as desired for viewing tissue dissection or retraction through a single balloon layer from inside the balloon 926.

After inflation is complete, the balloon 926 may be deflated by opening the suction line pinch clamp 923 and applying suction through male fitting 924 by suitable means such as a syringe or an operating room suction line as previously described. Once deflated, the laparoscope 909, and tunneling member 913 with the attached balloon may be withdrawn, either together or sequentially through the incision. If the endoscope guide 880 is used to retain access back to the dissected space, the guide 880 is left in place within the incision.

If insufflation is required for the procedure or additional trocars are needed, a trocar with cannula and skin seal assembly of the type previously described with reference to FIG. 40, for example, may be loaded over the distal end 931 of laparoscope 909. The laparoscope 909 is then inserted back into the incision (using the endoscope guide 880 to find the path back to the space if utilized) and advanced to the previously created space. After the space has been reached, the trocar with cannula and skin seal assembly may be advanced over the laparoscope shaft 911 into the incision and the skin seal secured in place as previously described.

Figure 94:
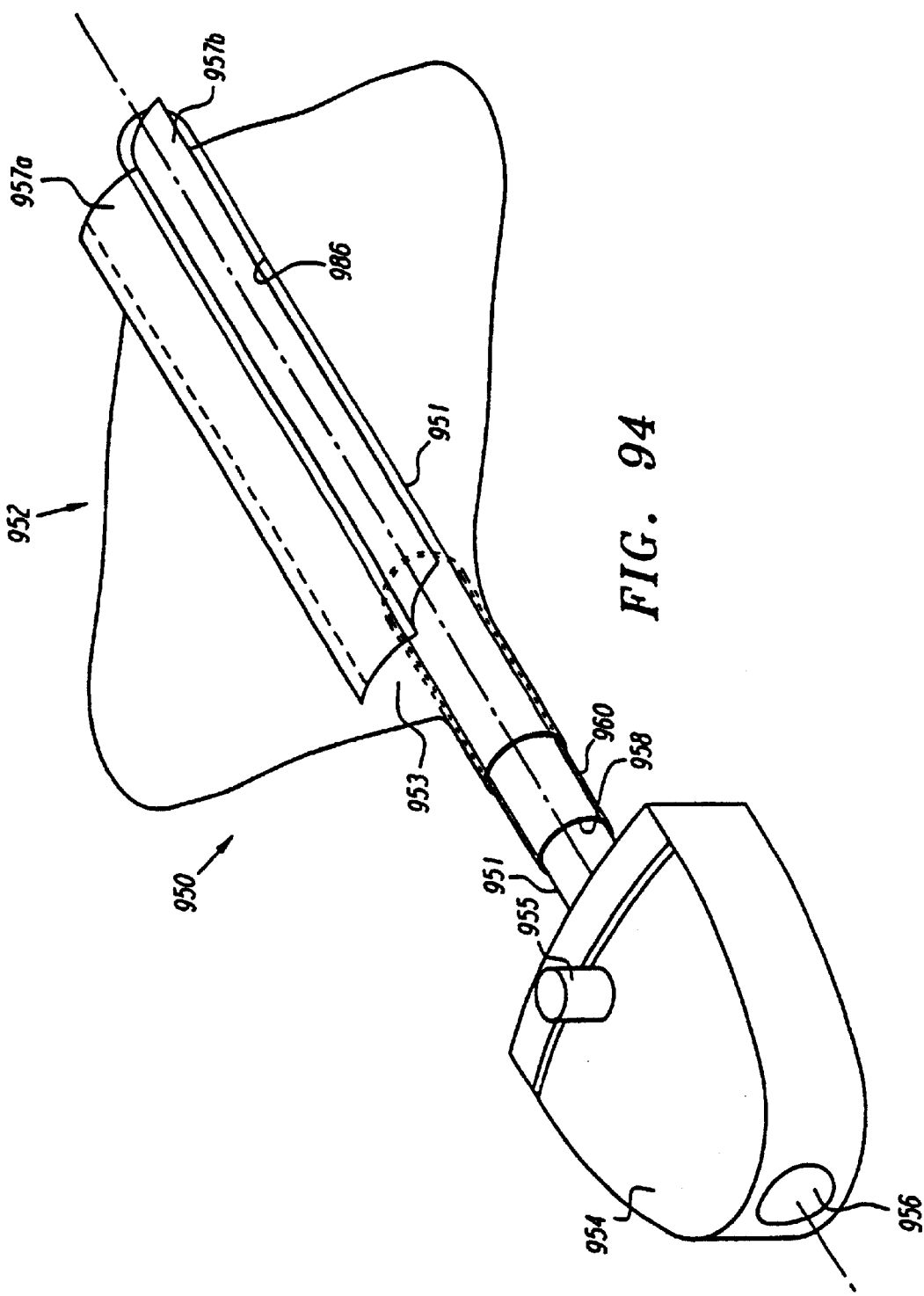
FIG. 94 is an isometric view of a one-piece tunneling apparatus according to the invention.
Figure 95:
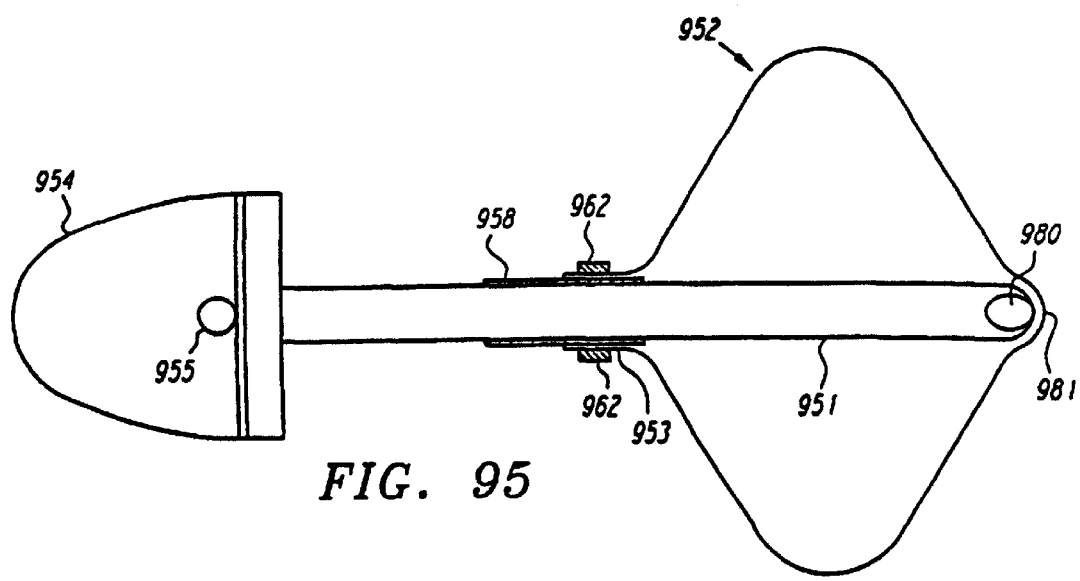
FIG. 95 is an orthogonal projection of the apparatus illustrated in FIG. 94.
Figure 96:
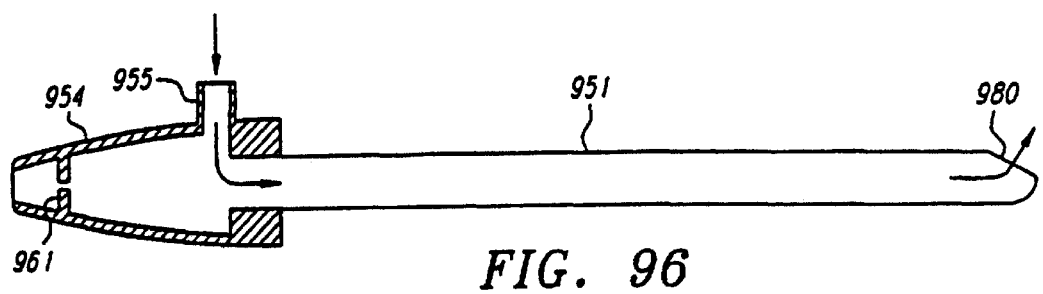
FIG. 96 is an orthogonal projection illustrating the handle and tunneling member portion of the device illustrated in FIGS. 94 and 95.

FIGS. 94 through 96 illustrate another embodiment of the invention that is substantially similar to the embodiment disclosed with reference to FIG. 93. The tunneling apparatus 950 in this particular embodiment is a one-piece design that has an elongate tunneling member 951 having a handle 954 secured thereto by a suitable fastening system such as a press fit or bonding using an appropriate adhesive or solvent, for example. A balloon 952 with an elongate neck 960 is mounted on the tunneling member 951. The tunneling member 951 has an internal bore 986 sized to receive a conventional 10 laparoscope. The bore 986 is in communication with an opening 956 provided in the handle 954 to provide a continuous passageway for the laparoscope. The tunneling member 951 thus serves as a scope cover in addition to serving as a blunt tipped obturator to tunnel bluntly through tissue in the manner previously described.

The tunneling member 951 may be of the same general construction as the tunneling member 913 described with reference to FIG. 93. As before, the tunneling member 951 is preferably fabricated from a suitable medical grade material having sufficient structural rigidity to tunnel bluntly through tissue in the body. A medical grade plastic, such as a polycarbonate, for example, has been found to perform satisfactorily for this purpose. The tunneling member 951 preferably has an open distal end 980 with a lip (see FIG. 95) to capture the distal end of the laparoscope. The open distal end 980 may be cut away at an angle, such as 45 degrees, for example, depending on the type of laparoscope utilized, to permit unobstructed observation by the laparoscope through the open distal end 980.

The elongate neck 960 of the balloon 952 is tucked or folded inwardly and secured to the tunneling member 951 anywhere along the length of the tunneling member 951 as shown at reference numeral 958. The neck 960 may be bonded to the tunneling member 951 by any one of a number of fastening options such as gluing, clamping, or heat sealing. The tuck 953 in the neck 960 permits the tunneling member 951 and laparoscope to be retracted from the distal extremity of the balloon 952 during inflation to provide depth of field and to allow for manipulation around in the balloon 952 during inflation. If the tuck 953 were not provided, the laparoscope could be withdrawn slightly to obtain field depth during inflation, but the tunneling member would remain nested in the nipple 981. This is less than optimal because the laparoscope would have to look out through tunneling member material as well as a balloon layer, rather than through the open distal end 980 of the tunneling member 951. Because the balloon 952 is preferably formed of a non-elastomeric material to permit controlled expansion to a desired shape, as the inelastic balloon 952 inflates the length of the balloon 952 becomes shorter. The inverted tuck 953 thus also provides sufficient material such that the distal end 980 of the tunneling member 951 can remain in a fixed location.

Any of the balloon and cover constructions previously disclosed may be utilized in conjunction with the one piece apparatus 950. In the illustrated integral balloon cover example of FIG. 94, the apparatus 950 is prepared for use by rolling or folded the wings of the balloon 952 about the tunneling member 951 in the manner previously described. Flaps 957a and 957b extend from the balloon 952 and are utilized to form the integral balloon cover to secure the balloon 952 to the tunneling member 951 during blunt tunneling through tissue in the body. One of the flaps is preferably provided with a series of longitudinally spaced apart perforations or slits 959. As previously described, this provides a weakened region so that the flaps 957a and 957b may break apart when inflation is commenced to permit the balloon 952 to expand to dissect tissue and form the desired anatomic working space. The balloon guide 880 illustrated in FIG. 86 or the balloon cover 316 illustrated in FIG. 41 may be used instead of, or in addition to, an integral balloon cover to retain the balloon 952 in position relative to the tunneling member 951.

The handle 954 has an inflation port 955 in communication with the interior space of the tunneling member 951 and is utilized to introduce a suitable inflation fluid, such as saline solution, for example, into the interior space of the balloon 952. The balloon 952 is inflated by introducing the recommended saline solution into the inflation port 955. The inflation port 955 is in communication with the internal bore 986 of the tunneling member 951 which, in turn, is in communication with the interior space of the balloon 952 through its open distal end 980. Because the internal bore 986 of the tunneling member opens into the interior of the balloon 952 through its open distal end 980, one or more seals 961 are mounted in the handle 954 proximal of the inflation port 955 to form a seal between the handle 954 and the laparoscope to prevent the inflation fluid from leaking out the handle 954. The seals may be of the same type disclosed in connection with the previous embodiments.

As illustrated in FIGS. 95, a temporary clamp 962 that remains outside the incision in the patient may be utilized to secure the tuck or inversion in the neck 960 of the balloon 952 to the tunneling member 951 during tunneling dissection when the apparatus 950 is bluntly advanced to the desired location within the body. The clamp 962 prevents the balloon neck 960 from coming unrolled if it is necessary to withdraw the apparatus 950 slightly during tunneling for reorientation. Once the desired location within the body has been reached, the clamp 962 may be removed to permit the tunneling member 951 and laparoscope to be withdrawn slightly for better visualization as previously described.

Figure 97:
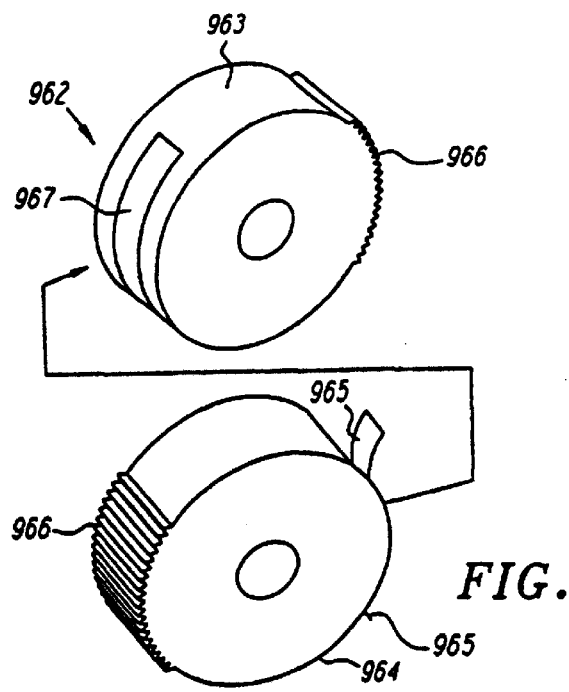
FIG. 97 is an isometric view of a clamp that may be utilized in connection with the device illustrated in FIGS. 94–96.

A suitable releasable clamp 962 for this purpose is illustrated in FIG. 97. Clamp 962 is formed from a pair of concentric mating rings 963 and 964 that are provided with aligning holes that are sized to accommodate the diameter of the inverted tuck 953 in the balloon neck 960 and the tunneling member 951. Inner clamp ring 964 is inserted into the camming slot 967 provided in the outer ring 963 and has two leaf springs 965 that extend outwardly and engage an interior surface of the outer ring 963. The leaf springs 965 urge the inner and outer rings 964 and 963 apart causing the tuck 953 and tunneling member 951 to be frictionally trapped therebetween. A finger grip 966 is provided on each ring to allow the rings to be more easily squeezed together to align the holes and release the clamp 962.

Figure 98:
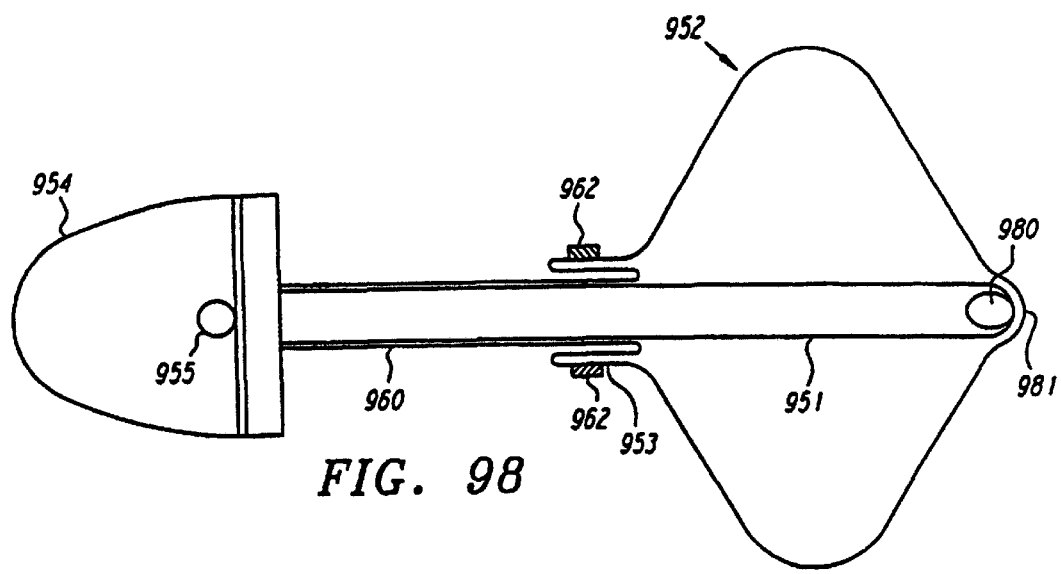
FIG. 98 is a plan view illustrating another embodiment of the apparatus illustrated in FIGS. 94–95 according to aspects of the present invention.
Figure 99:
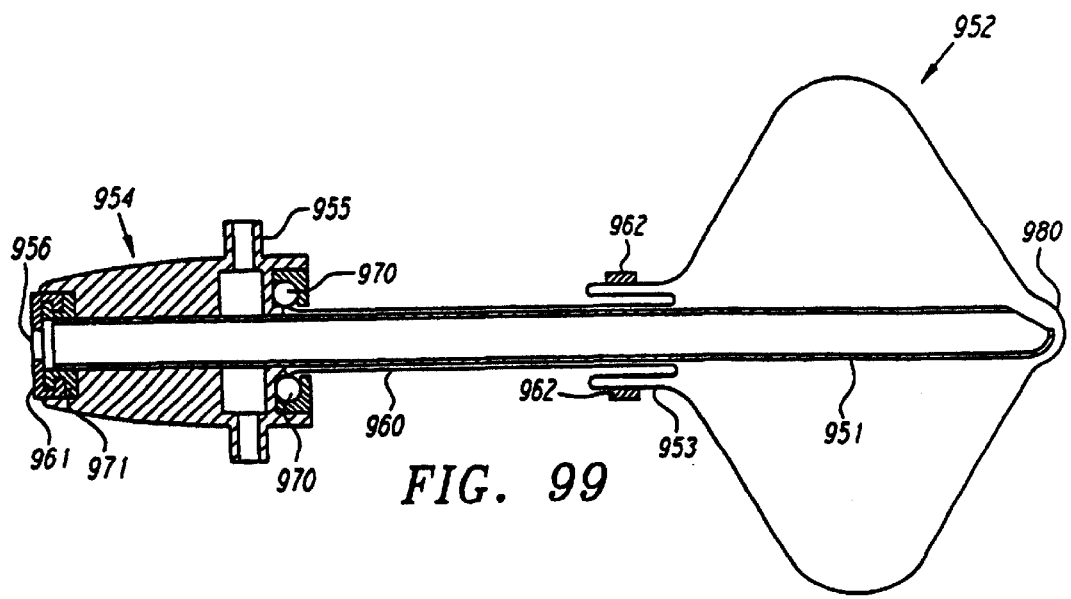
FIG. 99 is a partial cross-section of the apparatus illustrated in FIG. 98.

As shown in FIGS. 98 and 99, the elongate neck 960 of the balloon 952 may also extend into the handle 954. In this particular variation of the embodiments illustrated in FIGS. 93 and 94, the neck 960 is tucked inwardly and secured to the handle 954 in suitable fashion. In FIG. 99, an O-ring 970 is utilized to secure the neck 960 to the handle 954 and provide a fluid tight seal therewith. A suitable adhesive or solvent between similar materials can also be used to secure the balloon neck 960 to the handle 954. An inflation lumen is provided between the inflation port 955 and the annular space between the balloon neck 960 and the tunneling member 951. Inflation fluid delivered through the inflation port 955 passes directly into the interior space of the balloon 952 through the balloon neck 960. Optionally, with the addition of a transverse hole in the tunneling member 951, inflation could proceed through the open distal end 980 of the tunneling member 951 as described above.

A laparoscope seal 961 is mounted in the proximal end of the handle 954 to form a substantially fluid-tight seal between the interior space of the tunneling member 951 and the opening in the handle 956 that the laparoscope is inserted through. This prevents the inflation fluid from leaking out through the opening 956 when the balloon 952 is inflated. A seal retainer 971 may be mounted in the handle 954 to retain the seal 961 in position in the handle 954. Alternatively, the seal retainer 971 may be integrally formed in the handle 954.

Figure 100:
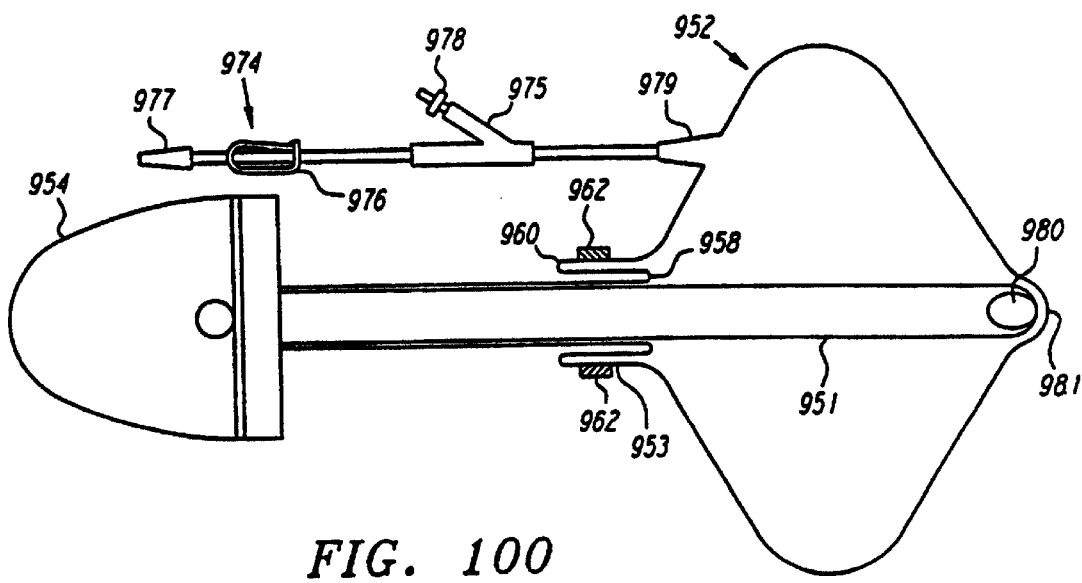
FIG. 100 is a plan view illustrating another embodiment of the device illustrated in FIGS. 94–95.

In FIG. 100, a balloon harness assembly 974, which is substantially similar to the inflation mechanism described with regard to the previous embodiments, may be utilized to inflate the balloon 952. The balloon inflation harness 974 includes a pinch clamp 976, a wye adaptor 975, a luer-type fitting with check valve 978, and an evacuation fitting 977, all of the type previously described. The balloon 952 is inflated by closing the pinch clamp 976, and injecting the inflation fluid through the fitting 978 into the balloon inflation lumen 979 which is in communication with the interior of the balloon 952.

Figure 101:
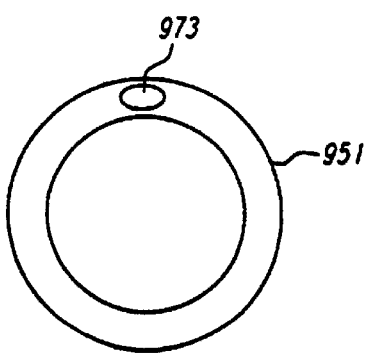
FIG. 101 is a cross-sectional view of a tunneling member having an inflation lumen provided therein according to the invention.

A lumen 973 formed in the tunneling member 951, as shown in FIG. 101, may also be used to inflate the balloon 952. The inflation lumen 973 is in communication with the inflation port 955 and opens into the interior space of the balloon 952 at some point along the length of the tunneling member 951 that resides within the interior space of the balloon 952.

The method of using the device 950 is substantially similar to the method of use previously described with reference to FIG. 93.

The tunneling apparatus embodiments disclosed in FIGS. 87–100 are all configured such that the inflation fluid is in communication with the interior of the tunneling member through the open distal end of the tunneling member. As a result, the laparoscope inserted through the tunneling member is also in contact with the inflation fluid, in other words, the laparoscope is "wetted." This configuration has several drawbacks. For one, it requires that a seal be employed between the scope and the tunneling member to enable pressurization and inflation of the balloon. Also, the shape of the distal tip of the tunneling member preferably accommodates scopes of varying types and viewing angles, while at the same time maintaining a generally rounded design so that it functions effectively as a blunt obturator. Hence, the hole in the distal end of the tunneling member involves a compromise in competing design parameters.

Figure 108:
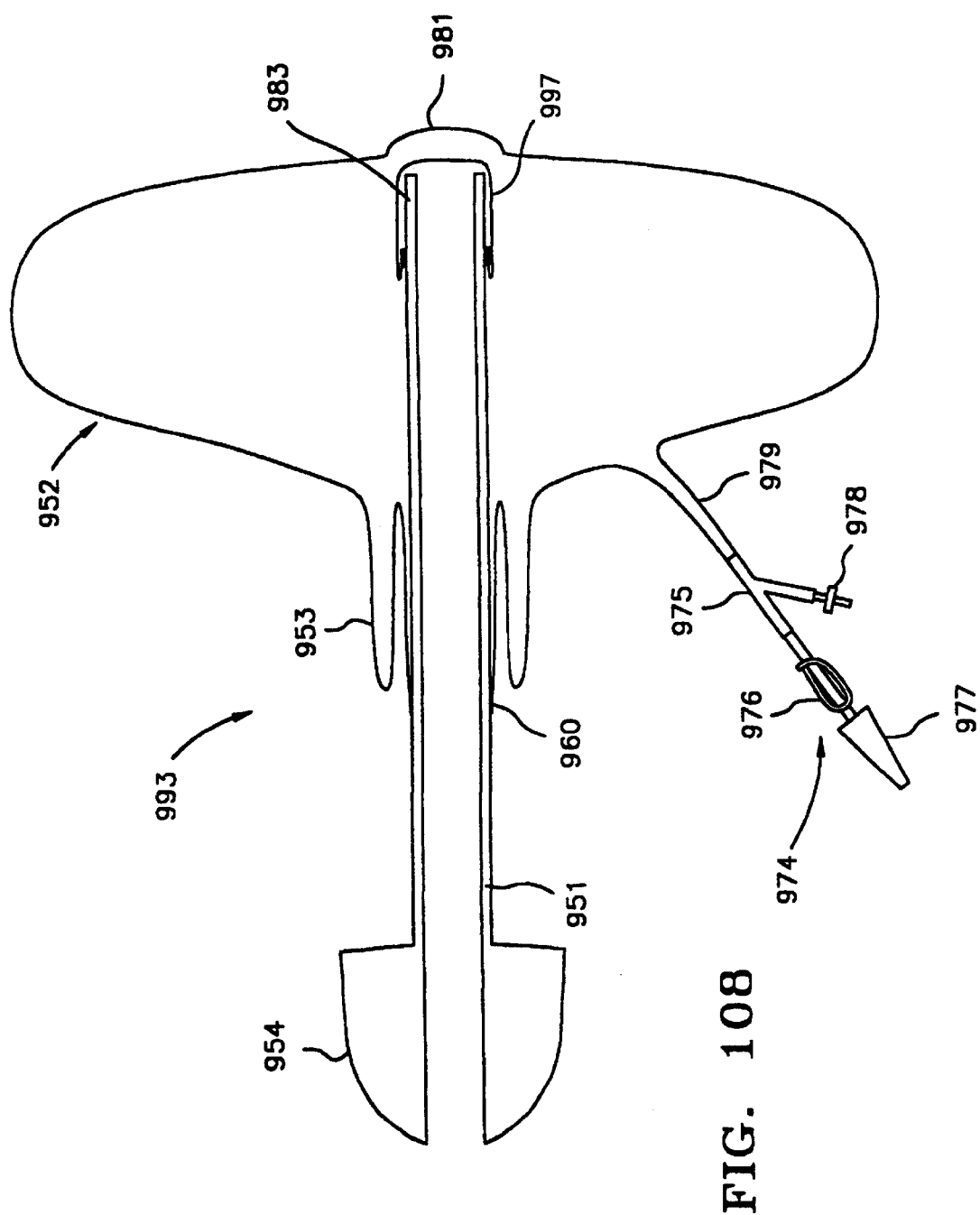
FIG. 108 is a cross-sectional view of another tunneling apparatus in accordance with the present invention.

Turning to FIG. 108, a tunneling apparatus 993 is disclosed which overcomes the aforementioned drawbacks of the previously described embodiments. The tunneling apparatus 993 is substantially similar to the embodiment disclosed with respect to FIG. 100. However, instead of the 45° angle cut and lip at the distal end of the tunneling member 951 of FIG. 100, the tunneling member 951 is open across the entire cross-section of the tube. The open distal end of the tube is fitted with a transparent, stretchable membrane 997 which is formed into a cup shape. The sides of the cup may be bonded to the outside of the tube in a fluid tight manner. Consequently, a laparoscope inserted into the tunneling member 951 is not in the interior of the balloon, i.e., inflation fluid used to inflate the balloon 952 does not contact the laparoscope. As opposed to the previously described wetted scope embodiments, the tunneling apparatus 993 is a non-wetted design with respect to the scope. A suitable membrane material may be, for example, Deerfield urethane #PT 9200U. Although a 0.003" thickness of membrane material is preferred, an increased thickness may provide a more rounded contour at the tip which may prove desirable for accomplishing blunt dissection with the distal tip of the tunneling apparatus 993. If the tip of the tunneling apparatus 993 is found to be too blunt, the tip 981 of the balloon 952 may be fitted with a rounded or streamlined cup into which the tip of the scope inserted into the membrane 997 may be positioned for tunneling. Alternatively, the cup may be disposed inside the balloon 952 in the tip 981. In yet another option, the balloon material may be bonded to the cup such that the balloon tip 981 does not block the cup itself. If visualization during tunneling is desired, the cup may be transparent. It is also contemplated that the tunneling member 951 may simply be provided with a sealed, closed distal tip, so long as the material of the tunneling member 951 is sufficiently transparent to provide adequate visualization with the laparoscope inserted through the closed distal tip. Alternatively, the tunneling member 951 may be sealed with a separate transparent cap (not shown).

The membrane 997 is sufficiently stretchable to conform to the contour of a laparoscope tip, regardless of its viewing angle. In this way, the membrane 997 will stretch smoothly across the viewing end of a laparoscope with minimum visual distortion. The length of the membrane cup walls on the outside of the tube can be chosen to provide sufficient elongation without rupturing the membrane 997 (i.e. for increased elongation capability, increase the length of the walls.)

It should be appreciated that visualization may be obscured if the viewing tip of the laparoscope is retracted away from the membrane 997. A user wishing to retract the scope in order to achieve a desired focal length between the tip of the laparoscope and the object being viewed, might retract the scope alone not realizing that for optimal viewing the laparoscope and tunneling member must be retracted together to keep the membrane 997 stretched across the tip of the laparoscope. In order to eliminate relative movement of the tunneling member 951 and the laparoscope, a locking means may be provided which manually locks the laparoscope to the tunneling member 951. For example, the locking means may comprise a tube extension at the proximal end of the tunneling member. The tube extension is split and a clamp is installed over the split part of the extension tube. To lock the laparoscope within the tunneling member 951, the clamp is tightened which compresses the diameter of the tube extension causing it to grip the outer diameter of the laparoscope to prevent axial movement.

It is important to appreciate that upon inflation of the balloon 952, fluid pressurization applies a force axially to the tunneling member 951 tending to drive the tunneling member 951 proximally out of the balloon 952 and/or everting the folded neck 953 of the balloon 952. To prevent the folded neck 953 from everting before it is desired, a releasable clamp (not shown in FIG. 108), as described above with regard to FIG. 95, may be utilized to secure the folded neck 953.

Figure 102:
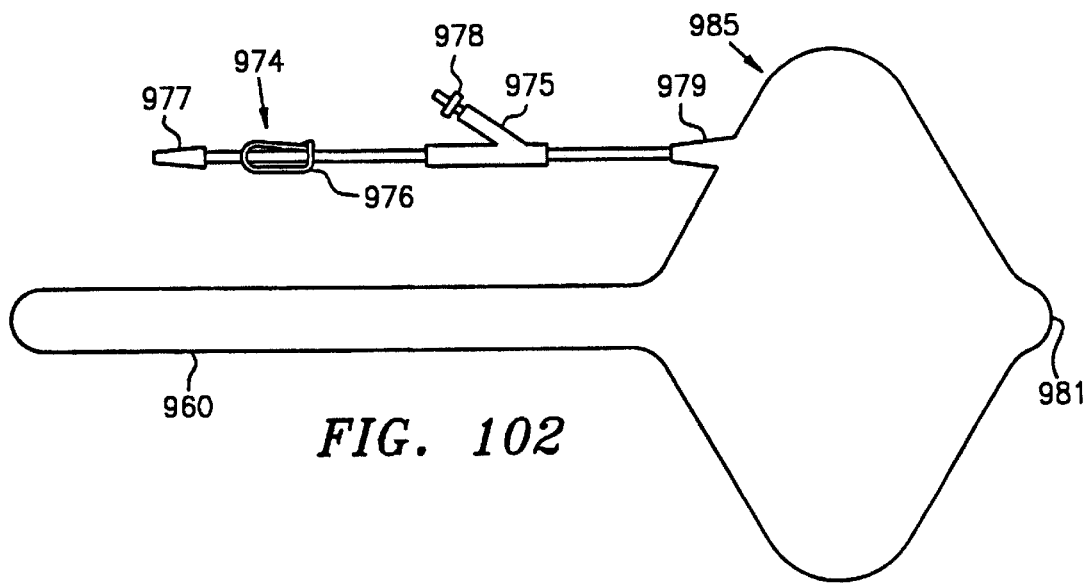
FIG. 102 is a plan view illustrating another balloon construction in accordance with the invention.
Figure 103:
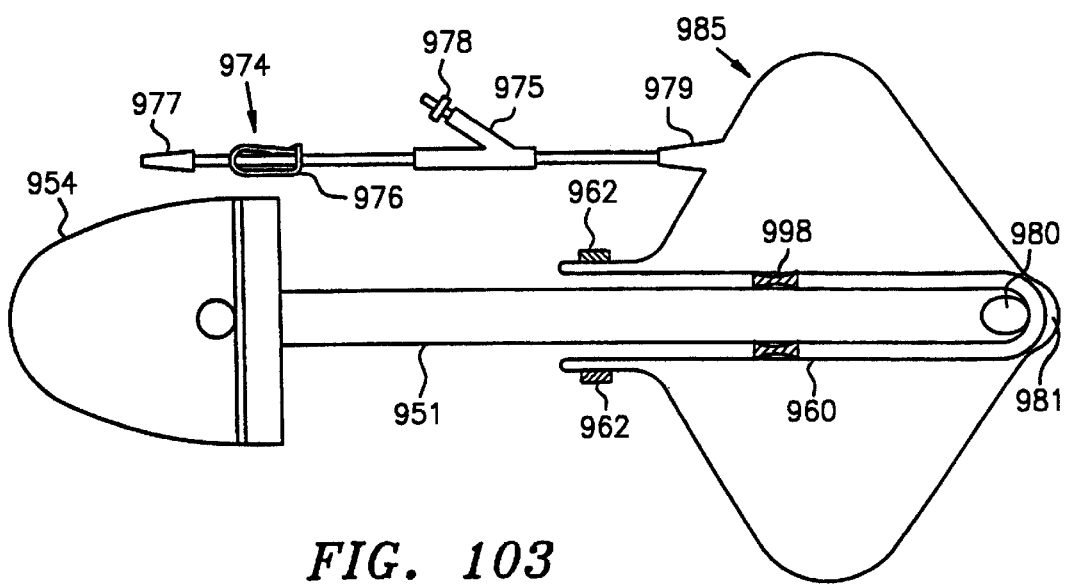
FIG. 103 is a plan view illustrating the balloon illustrated in FIG. 102 mounted on a handle and tunneling member assembly in accordance with the invention.

Another embodiment of tunneling apparatus in accordance with the present invention is illustrated in FIGS. 102 and 103. Like the tunneling apparatus 993 described above, the tunneling apparatus 994 is also a non-wetted scope design wherein the scope is not in the interior of the balloon 985. The elongated neck 960 of the balloon 985 seals both the tunneling member 951 and the laparoscope from the interior of the balloon 985 such that the balloon inflation fluid does not contact the laparoscope. In this embodiment, the balloon 985 has an elongated neck 960 that is completely sealed. The balloon 985 is preferably formed of a highly transparent material. This highly transparent material may be used for the entire balloon 985. Alternatively, the highly transparent material may be used only for the tip area through which the scope views and joined to other balloon material to make up the entire balloon 985. The elongate neck 960 may be sealed by welding the balloon material all the way around, for example. The balloon 985 illustrated in FIG. 102 may be of arbitrary shape and may be utilized in conjunction with the previously described handle 954 and tunneling member 951 shown in FIG. 103. In order to mount the balloon 985 on the tunneling member 951, the balloon neck 960 is inverted over the tunneling member 951, and the tunneling member 951 is inserted into the balloon 985 until it abuts the nipple 981 provided in the distal extremity of the balloon 985. A balloon cover of the types previously described may be provided for this balloon 985 as well.

With this particular embodiment, it may also be necessary or desirable to use a temporary clamp 962, as shown in FIG. 103, to clamp the inverted balloon neck 960 to the tunneling member 951 to prevent the tuck in the neck 960 from unrolling if it is necessary to withdraw or reorient the apparatus during tunneling. The clamp 962 may be of any suitable type, as previously described. Alternatively, the surgeon may grasp the inverted neck in his or her hand to prevent the tuck from unrolling. Because the balloon 985 has a sealed neck 960, an inflation harness 974 of the type previously described is required to inflate the balloon 985. One benefit of utilizing the balloon 985 is that because the balloon 985 is sealed, it is not necessary to utilize seals in the handle 954 to form a seal between the laparoscope and the tunneling member 951.

As explained above with respect to FIG. 108, pressurization of the balloon 985 produces a force tending to push the tunneling member 951 proximally out of the balloon. It is undesirable that the tunneling member 951 be capable of being withdrawn or driven completely from the neck 953. If that were to happen visualization would be lost and it would be difficult to reinsert the tunneling member 951. Therefore, at a point along the balloon neck 960 distal of the clamp 962, the neck may be bonded or clamped to the tunneling member 951 to prevent the tunneling member 951 from being capable of being completely withdrawn from the balloon neck 960. The bond or clamp 998 need not be fluid tight since the tunneling member is non-wetted (not in communication with the interior of the balloon 985), but only need to be sufficiently strong to prevent the neck 960 from peeling away from the tunneling member 951 as the tunneling member 951 moves proximally and the neck 960 everts.

Turning to FIG. 109, another embodiment of tunneling apparatus 985 having a non-wetted scope configuration is illustrated. The tunneling apparatus 985 is substantially similar to the embodiment shown in FIGS. 102–103 except for several additional features. Relative movement of the scope and the tunneling member 951 may be accomplished using the split tube extension and clamp as described above for the embodiment of FIG. 108. An alternative to the manual lock can be easily achieved by providing one or more slots or openings 982 in the tunneling member 951. When the balloon 985 is pressurized with inflation fluid, the neck 960 is forced through the openings 982 and into contact with the scope 909 thereby gripping the scope 909 as shown in FIG. 109A. In this manner, scope locking is automatic with balloon inflation.

The bond or clamp 998 between the balloon neck 960 and the tunneling member 951 is preferably near the proximal end of the openings 982, but may be placed elsewhere so as to allow sufficient withdrawal of the tunneling member 951 and scope 909 to obtain the desired focal length.

To prevent the folded neck 953 from everting before it is desired, a releasable clamp (not shown in FIG. 108), as described above with regard to FIG. 95, may be utilized to secure the folded neck 953. Optionally, an alternative retaining means is shown in FIG. 109 for preventing the folded neck 953 from prematurely everting during inflation. A slot or opening 972 is provided proximal of the folded neck 953. One or more strings or straps 999 are fastened to the folded neck 953 at or near the proximal end the folded neck 953. The straps 999 are then passed through the openings 972 and are fastened to the tunneling member 951. Preferably, the straps 999 are passed out the proximal end of the tunneling member 951 between the tunneling member 951 and the scope shaft, and fastened such that they can be manually released to permit withdrawal of the tunneling member 951 and scope 909 for viewing.

A further benefit of the proximal openings 972 in that, being exposed directly to the body tissue near the incision, bleeding at this point would soon be apparent. Blood at the proximal end of the tunneling member 951 or on the scope 909 when they are withdrawn would indicate bleeding within the tunnel leading to the operative site. This region of tunneled access is otherwise difficult to monitor since it is out of the surgeon's view.

In a preferred method of utilizing any of the one-piece apparatus illustrated as having inverted tucks in the balloon neck, the device is inserted through an incision in the body and advanced bluntly to a desired location where tissue dissection is to occur. As previously mentioned, during blunt tunneling the temporary clamp 962, if utilized, secures the inverted neck 960 to the tunneling member 951 to prevent the neck 960 from unrolling if it is necessary to withdraw the apparatus. During tunneling, the advancement of the apparatus through tissue layers may be observed through the laparoscope through the open distal end 980 of the tunneling member 951.

After the desired location has been reached, the tunneling member 951 and laparoscope may be withdrawn slightly by grasping the handle 954 and withdrawing the handle 954 and laparoscope to gain clearance from the nipple 981 of the balloon 985. Before this is done, however, it is necessary to remove the clamp 962 or remove the straps 999 if utilized. The balloon 985 is then inflated in the manner previously described, and tissue dissection can be observed as in previous embodiments through the laparoscope as the laparoscope again looks out through the open distal end 980 of the tunneling member 951. The device and laparoscope are then withdrawn from the body and additional trocars, as required for the procedure, may be inserted.

Figure 104:
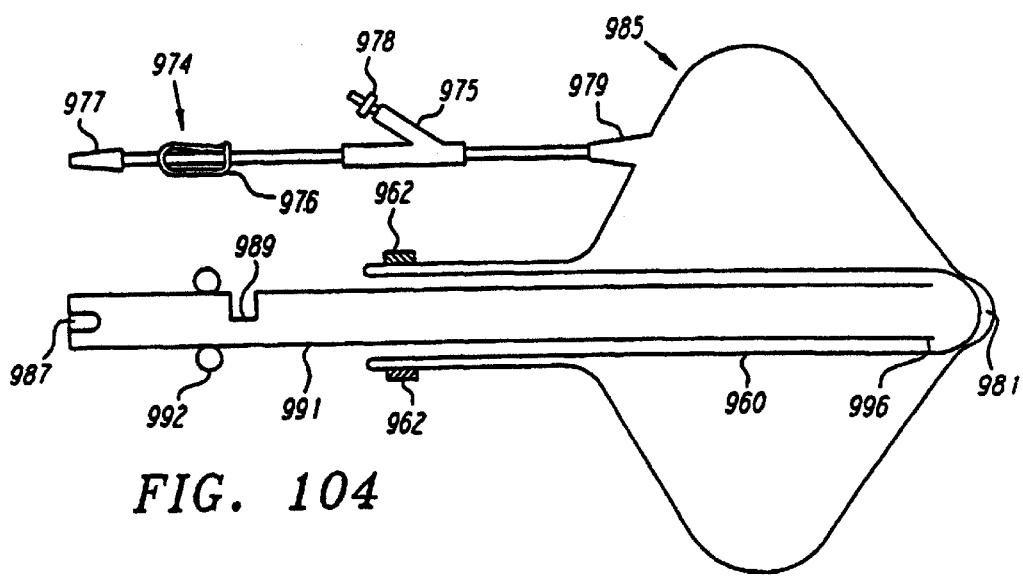
FIG. 104 is a plan view illustrating a disposable balloon cartridge according to the invention.
Figure 105:
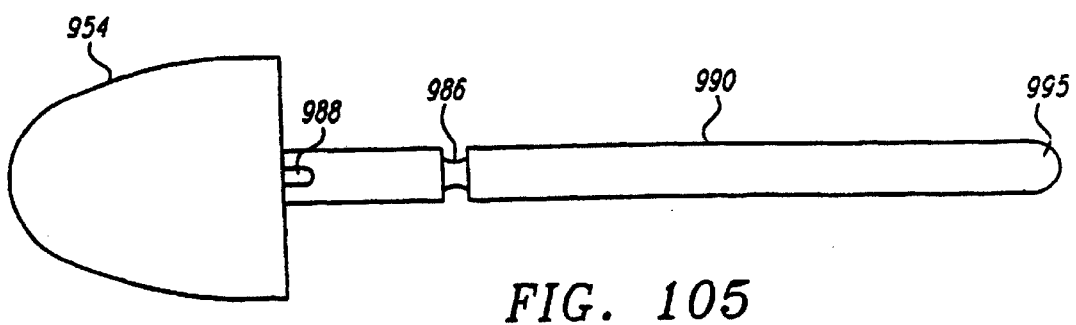
FIG. 105 is a plan view of a reusable combination handle and tunneling member assembly for use with the disposable balloon cartridge illustrated in FIG. 104.

A reusable version of the expansible tunneling apparatus of the present invention is shown in FIGS. 104 and 105. In FIG. 104, the closed neck balloon 985 illustrated in FIGS. 102 and 103 is illustrated mounted on a tubular member 991. The tubular member 991 is sized to accommodate the insertion of the tunneling member 990 illustrated in FIG. 105. The tunneling member 990 in this embodiment is preferably a rod, but a tunneling member 990 with an internal bore sized to receive a laparoscope of the type illustrated in connection with previous embodiments could be utilized if laparoscopic visualization is desired. When the tunneling member 990 is fully inserted into the tubular member 991, the distal end 995 of the tunneling member 990 preferably extends beyond the open distal end 996 of the tubular member 991 and mates with the nipple 981 provided in the balloon 985.

In this reusable embodiment, the handle 954 and tunneling member 990 portion of the apparatus are inserted into the tubular member 991 and removably secured thereto by a suitable fastening system. One example of a suitable mechanism for fastening the handle 954 and tunneling member 990 to the tubular member 991 is illustrated in FIGS. 104 and 105 and comprises a slot 989 in the tubular member 991 which is aligned with a corresponding groove 986 formed in the tunneling member 990. An O-ring 992 may be placed in the slot 989 to secure the tubular member 991 to the tunneling member 990. In this arrangement, the O-ring 992 is placed in shear and provides a particularly effective temporary attachment mechanism. A key or tab 988 formed on the tunneling member 990 or, alternatively, extending from the handle 954, mates with a corresponding notch 987 in the tubular member 991 to prevent the tunneling member 990 from rotating with respect to the tubular member 991 during use of the device. Of course, other suitable anti-rotation mechanisms may be utilized. Furthermore, an open necked balloon of the type illustrated in FIG. 94, for example, may be utilized in conjunction with this reusable embodiment. In this case, the open balloon neck could be bonded anywhere along the length of the tubular member 991.

This reusable embodiment of the tunneling apparatus of the present invention may be utilized in the same manner as previously described. After a surgical procedure has been performed with the device of FIGS. 104 and 105, the handle 954 and the tunneling member 990 attached thereto may be removed from the remainder of the apparatus by removing the O-ring 992. The handle 954 and tunneling member 990 may be reused, after appropriate sterilization, in further procedures to make the apparatus more economical to use. Thus, the combination handle 954 and the tunneling member 990 form a reusable portion, while the balloon 985 and tubular member 991 comprise a disposable cartridge.

Figure 106:
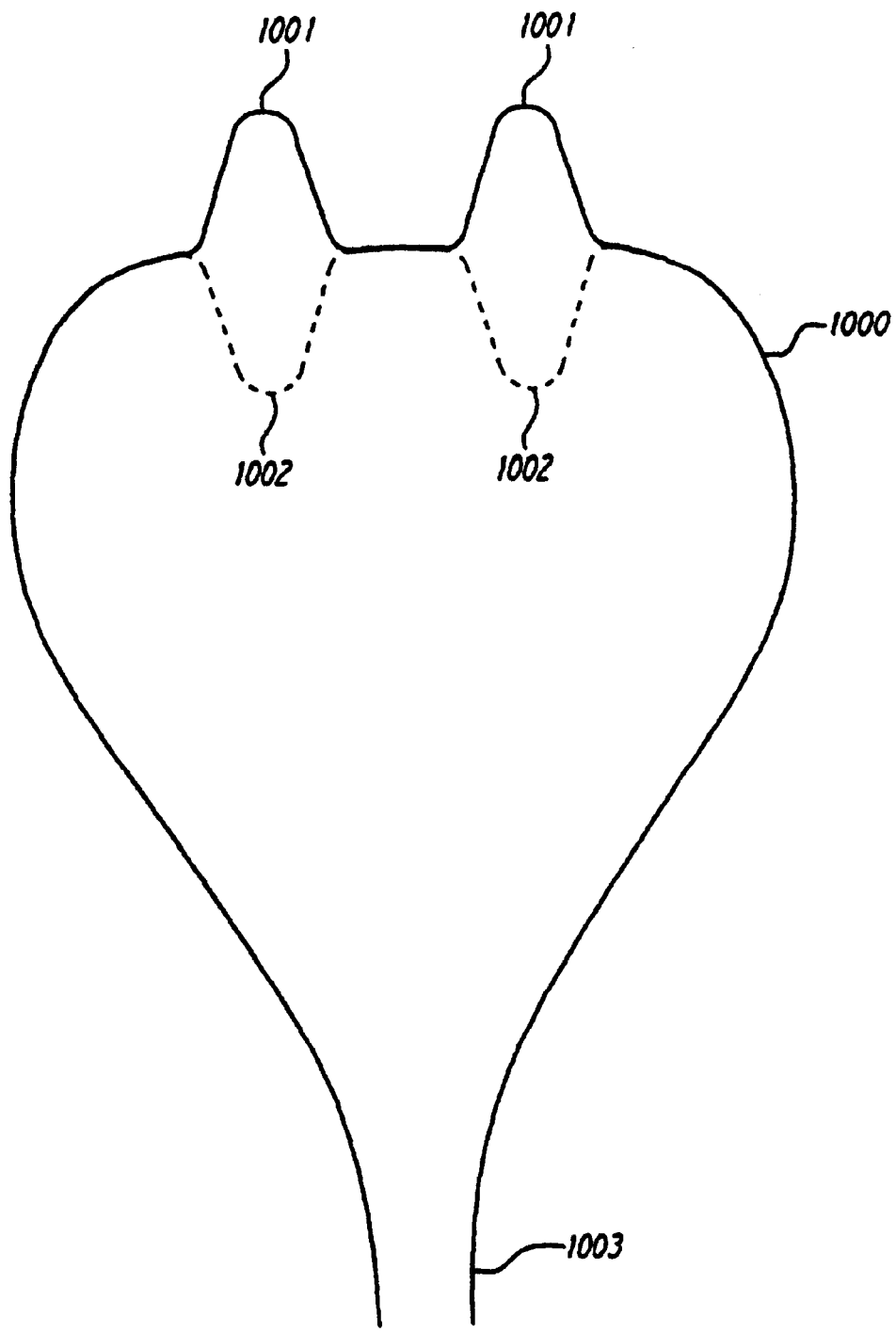
FIG. 106 is a plan view of yet another balloon formed in accordance with the invention.

A balloon 1000 preferably formed from a non-elastomeric material with extending horns 1001 is illustrated in FIG. 106. This particular balloon shape has been found to be particularly efficacious for use in connection with bladder neck suspension procedures. Before inflation, the horns 1001 are everted within the balloon 1000 as shown by the dashed lines indicated by reference numeral 1002. This permits the balloon 1000 to be rolled or folded into a compact arrangement. When the balloon 1000 is inflated, the horns 1001 extend outwardly when the internal balloon inflation pressure rises enough to overcome the fold resistance at reinversion. This fairly reliably happens secondarily to inflation of the main body of the balloon 1000. The balloon 1000 may have an elongate neck 1003 and may be utilized with any of the previously disclosed embodiments of the tunneling apparatus of the present invention.

Figure 107:
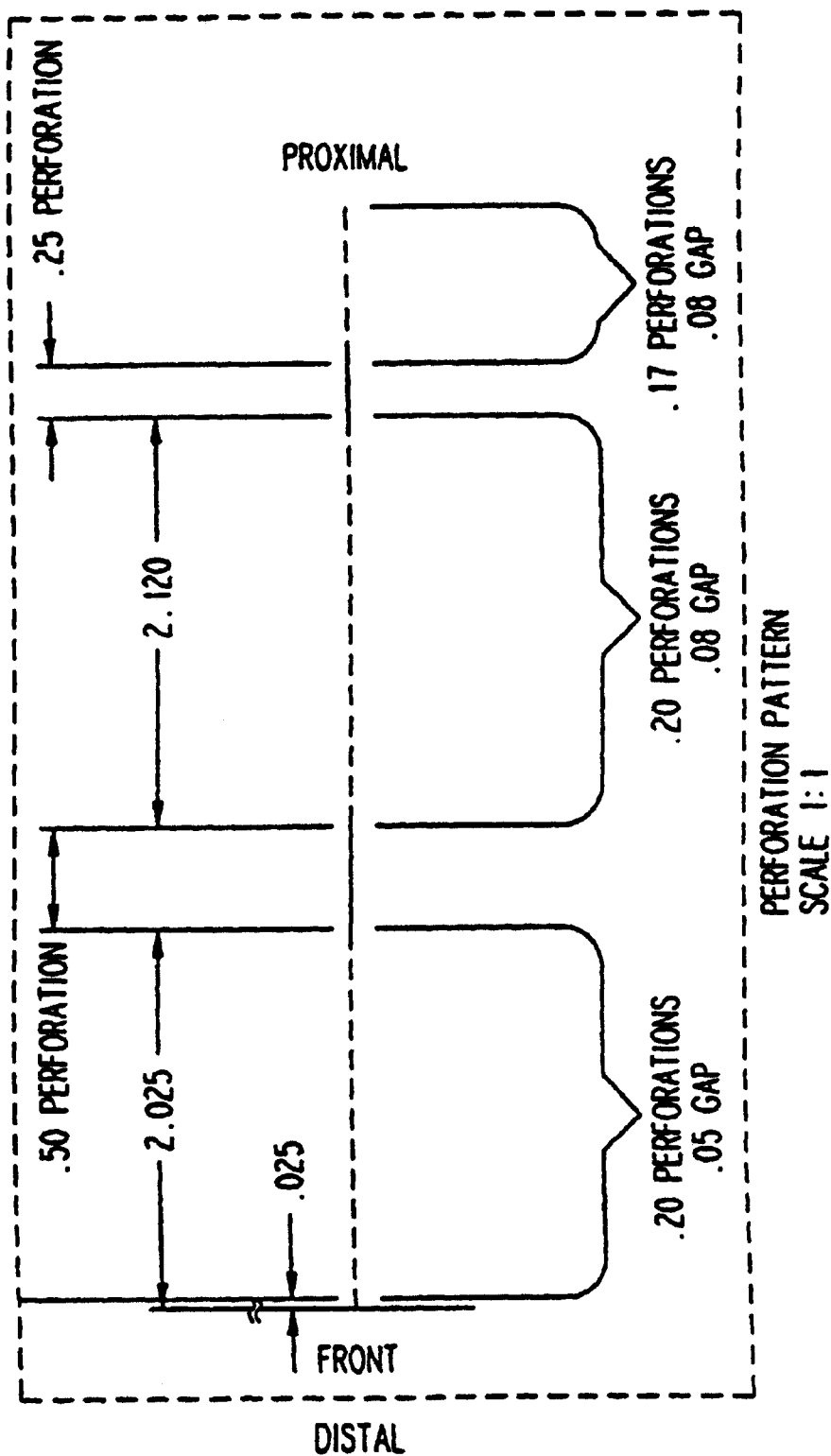
FIG. 107 is schematic of a preferred arrangement for the slits or perforations in a balloon cover in accordance with the parent invention.

FIG. 107 illustrates a presently preferred arrangement for the slits or perforations in any of the integral balloon cover embodiments when it is desirable for the distal opening of the integral cover to separate before proximal separation occurs. When the balloon cover construction disclosed in FIG. 107 is utilized, upon inflation of the balloon, the balloon cover separates at the 0.50 inch perforation shown in FIG. 107 and then the cover breaks apart distally. Thereafter, the cover tears away proximally.

Although the present invention has been principally described in conjunction with hernia repair, it should be appreciated that the various balloon constructions and the methods hereinbefore described can be utilized in other surgical procedures. In connection with such procedures, if specialized or custom-type balloons are required for a specific procedure, it can be seen that such balloon can be readily constructed in accordance with the present invention and utilized as hereinbefore described to perform those procedures. Examples of such procedures which lend themselves to use of the balloon dissectors and methods disclosed herein include extraperitoneal endoscopic pelvic lymph node dissection. Similarly, the balloon dissectors and procedures described herein may be used in connection with bladder neck suspension procedures to cure urinary incontinence. Moreover, the various apparatus and methods can be utilized with little or no modifications to the shape of the balloon for lymphadenectomies. The various apparatus and methods can also be used in retroperitoneal procedures. The horseshoe-shaped balloon described can be utilized for dissecting around obstructions such as ventral hernias and median raphes. In all of these procedures, it is desirable to make them as minimally invasive as possible and, where feasible, to utilize endoscopic techniques.

From the foregoing, it can be seen that the apparatus and methods of the present invention can be utilized in connection with various laparoscopic surgical procedures. While embodiments and applications of the disclosed devices and associated methods have been shown and described, it would be apparent to those skilled in the art that many more modifications are possible without departing from the inventive concepts disclosed herein. The invention therefore is not to be restricted except in the spirit of the following claims.

What is claimed is:

1. A surgical device comprising:
   a tubular member having a bore extending from a proximal end to a distal end of said tubular member;
   a balloon disposed on said tubular member, said balloon having an interior inflation space and an elongate neck, said tubular member extending through said elongate neck;
   said elongate neck folded to reduce its length, and thereby producing a portion of the neck forming an outer layer and a portion of the neck forming an inner layer wherein said inner layer is between said outer layer and said tubular member; and a handle disposed on said outer layer of said neck.

2. The surgical device of claim 1 wherein said handle is formed by enlarging the diameter of a portion of the outer layer.

3. The surgical device of claim 1 wherein said handle comprises a tab attached to said outer layer of said neck.

4. The surgical device of claim 1 wherein said handle comprises a loop attached to said outer layer of said neck.

5. The surgical device of claim 1 wherein said elongate neck extends proximal of said folded neck such that said inner layer is between said outer layer and said elongate neck.

6. The surgical device of claim 1 wherein said elongate neck is sealingly attached to said tubular member distal of said elongate neck.

7. The surgical device of claim 1 further comprising a stretchable membrane disposed over the distal end of said tubular member and attached to said tubular member creating a fluid tight seal over said distal end of said tubular member.

8. The surgical device of claim 1 further comprising a substantially transparent, stretchable membrane disposed over said distal end of said tubular member, said stretchable membrane formed in the shape of a cup having sides, said sides bonded to the tubular member in a fluid tight manner sealing said distal end of said tubular member.

9. The surgical device of claim 8 further comprising a blunt dissecting cup disposed on a distal tip of said balloon adjacent said stretchable membrane.

10. The surgical device of claim 9 wherein said blunt dissecting cup is disposed on the interior of said balloon.

11. The surgical device of claim 9 wherein said blunt dissecting cup is disposed on the exterior of said balloon.

12. The surgical device of claim 1 wherein said bore of said tubular member is adapted to receive a laparoscope.

13. The surgical device of claim 12 further comprising a laparoscope inserted into said bore of said tubular member and said laparoscope is forced into said stretchable membrane stretching said membrane over a distal tip of said laparoscope.

14. The surgical device of claim 13 further comprising a locking means for releasably locking said laparoscope to said tubular membrane to prevent relative axial movement between said laparoscope and said tubular member.

15. The surgical device of claim 13 further comprising a locking device comprising a tube extension attached to said tubular member, at least a portion of said tube extension being split, and a clamp installed over said split portion which can be tightened to compress the diameter of the split portion causing it to grip an outer diameter of said laparoscope.

16. The surgical device of claim 13 further comprising a releasable clamp installed on said folded neck prevent said fold neck from unfolding.

17. The surgical device of claim 1, said balloon having an unfolded state and a folded state, wherein in said unfolded state, said elongate neck has a sealed proximal end, and said sealed proximal end is inverted into said elongate neck over said tubular member such that said sealed proximal end is adjacent said distal end of said tubular member.

18. The surgical device of claim 17 wherein said tubular member has a transverse opening through a wall of said tubular member at a portion of said tubular member inserted into said elongate neck of said balloon such that when said balloon is pressurized, the neck is forced through the opening to grip a laparoscope inserted into said tubular member.

19. A surgical device comprising:

a tubular member having a bore extending from a proximal end to a distal end of said tubular member;

a balloon disposed on said tubular member, said balloon having an interior inflation space and an elongate neck, said balloon having an unfolded state and a folded state, wherein in said unfolded state, said elongate neck has a sealed proximal end, said sealed proximal end inverted into said elongate neck over said tubular member such that said sealed proximal end is adjacent said distal end of said tubular member.

20. The surgical device of claim 19 wherein said elongate neck further comprises an inwardly folded portion thereby producing a portion of the neck forming an outer layer and a portion of the neck forming an inner layer wherein said inner layer is between said outer layer and said tubular member.

21. The surgical device of claim 20 further comprising a handle disposed on said outer layer of said neck.

22. The surgical device of claim 20 further comprising a releasable retaining means for preventing the said folded portion of the neck from unfolding.

23. The surgical device of claim 20 further comprising a strap fastened to said folded portion of said neck and also fastened to said tubular member for preventing said folded portion of the neck from unfolding.

24. The surgical device of claim 20 wherein said elongate neck is fastened to said tubular member at a location distal of said folded neck.

25. The surgical device of claim 19 wherein said elongate neck is fastened to said tubular member.

26. The surgical device of claim 19 wherein said proximal end of said elongate neck in its uninflated state is sealingly attached to a transparent, stretchable membrane.

27. The surgical device of claim 19 wherein said balloon is made of a substantially transparent material.

28. The surgical device of claim 19 wherein said proximal end of said elongate neck is made of a substantially transparent material.

29. A surgical device comprising:

an elongate tunneling member;

a balloon disposed on said tunneling member, said balloon having an interior inflation space and an elongate neck, said tunneling member extending through said elongate neck;

said elongate neck folded to reduce its length, and thereby producing a portion of the neck forming an outer layer and a portion of the neck forming an inner layer wherein said inner layer is between said outer layer and said tubular member; and a handle disposed on said outer layer of said neck.

30. The surgical device of claim 29 wherein said handle is formed by enlarging the diameter of a portion of the outer layer.

31. The surgical device of claim 29 wherein said handle comprises a tab attached to said outer layer of said neck.

32. The surgical device of claim 29 wherein said handle comprises a loop attached to said outer layer of said neck.

33. The surgical device of claim 29 wherein said tunneling member is a solid obturator.

34. The surgical device of claim 29 wherein said tunneling member is a tube having a bore extending from a proximal end to a distal end of said tunneling member.

35. The surgical device of claim 29 wherein said tunneling member comprises an elongate tube having an open proximal end and a sealed, closed distal end.

36. The surgical device of claim 35 wherein said distal end is sealed using a transparent cap.

* * * * *